(12) United States Patent
Diederich et al.

(10) Patent No.: US 7,319,101 B2
(45) Date of Patent: Jan. 15, 2008

(54) COMT INHIBITORS FOR THE TREATMENT OF DEPRESSION AND IMPAIRED COGNITION

(75) Inventors: François Diederich, Dietikon (CH); Roland Jakob-Roetne, Inzlingen (DE); Christian Lerner, Cambridge, MA (US); Ralph Paulini, Zurich (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 483 days.

(21) Appl. No.: 11/011,887

(22) Filed: Dec. 14, 2004

(65) Prior Publication Data

US 2005/0137162 A1      Jun. 23, 2005

(30) Foreign Application Priority Data

Dec. 19, 2003   (EP)   .................................. 03104828

(51) Int. Cl.
   C07D 473/34    (2006.01)
   A61K 31/52     (2006.01)
   A61P 25/16     (2006.01)
   A61P 25/24     (2006.01)
   A61P 25/18     (2006.01)

(52) U.S. Cl. ................. 514/263.4; 544/277; 546/282.4; 549/447

(58) Field of Classification Search ................ 544/277; 514/263.4
   See application file for complete search history.

(56) References Cited

U.S. PATENT DOCUMENTS 5,389,653 A     2/1995  Bernauer et al.

FOREIGN PATENT DOCUMENTS

EP          0 426 468 B1       5/1991

OTHER PUBLICATIONS

"Understanding Parkinson's Disease" http://www.stalevo.com/info/simplystated/parkinsons_disease_treatment.jsp?checked=y downloaded from the Internet Jul. 15, 2004.*
"Parkinson's Treatments: L-dopa" <http://www.macalester.edu/~psych/whathap/UBNRP/parkinsons/ldopa.html> downloaded from the Internet Jul. 15, 2004.*
Mannisto, P.T., et al, Pharmacological Reviews, Williams and Wilkins Inc., pp. 593-628 (1999), XP001203431.
Eric K. Yau, et al, Journal of Organic Chemistry, vol. 55, No. 10, pp. 3147-3158 (1990), XP002343637.
Christian Lerner, et al., Angewandte Chemie. International Edition, vol. 40, No. 21, pp. 4040-4042 (2001), XP002343638.
Christian Lerner, et al., Helvetica Chimica Acta., vol. 86, No. 4, pp. 1045-1061 (2003), XP002343640.
Nishimura, K et al., Angew. Chem. Int. Ed. 2001, vol. 40, No. 2, pp. 440-442.
Lerner, C. et al., Org. Biomol. Chem., 2003, vol. 1, pp. 42-49.
Masjost, B. et al., Chem. Eur. J., 2000, vol. 6, No. 6, pp. 971-982.
Fava, M. et al., J. Clin. Psychopharmacol. vol. 19(4), 1999, pp. 329-335.
Weickert, C. et al., Schizophr. Bull., 1998, vol. 24, pp. 303-316.
Weinberger, D. et al., Biol. Psychiatry, 2001, vol. 50, pp. 825-844.
Egan, M. et al., Proc. Natl. Acad. Sci. USA, 2001, vol. 98, pp. 6917-6922.
Kurth, M. et al., Neurology, 1997, vol. 48, pp. 81-87.
Myllylä, V. et al., European Journal of Neurology, vol. 4, 1997, pp. 333-341 (Handbook of Parkinson's Disease (3$^{rd}$ Ed.)) and Pfeiffer, R., Catechol-O-Methyltransferase in Parkinson's Disease, vol. 20, pp. 437-451.
Gershanik, O. et al., Progress in Neuro-Psychopharmacology & Biological Psychiatry, vol. 27, 2003, pp. 963-971.
Lachman, H. et al., Pharmacogenetics, 1996, vol. 6, pp. 243-250.
Malhorta, A. et al., Am. J. Psychiatry, 2002, vol. 159, pp. 652-654.
Smith, K. et al., Chem. Res. Toxicol., 2003, vol. 16, pp. 123-128.
d'Ischia, M. et al., Bioorganic & Medicinal Chemistry, 1995, vol. 3, pp. 923-927.

* cited by examiner

*Primary Examiner*—Mark L. Berch
(74) *Attorney, Agent, or Firm*—George W. Johnston; Patricia S. Rocha-Tramaloni; Kimberly J. Prior

(57) ABSTRACT

The present invention relates to compounds of formula I

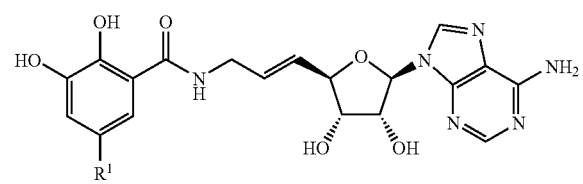

wherein $R^1$ is as defined in the specification
and to esters thereof which are hydrolyzable under physiological conditions and to the pharmaceutically acceptable salts thereof. The compounds of the invention are inhibitors of COMT and, thus, are useful for the treatment of diseases for which COMT inhibition is beneficial. The invention further relates to the treatment, control, or prevention of diseases such as depression, schizophrenia, Parkinson's disease, and to improve cognition.

31 Claims, No Drawings

COMT INHIBITORS FOR THE TREATMENT OF DEPRESSION AND IMPAIRED COGNITION

FIELD OF THE INVENTION

The present invention relates to compounds that inhibit catechol-O-methyltransferase (COMT) and their use for improving cognitions and in the treatment of CNS disorders such as depression, schizophrenia, and Parkinson's disease.

BACKGROUND OF THE INVENTION

Numerous documents describe the current knowledge on COMT—inhibition, for example—in the field of depression:
Fava, M., J. F. Rosenbaum, A. R. Kolsky, J. E. Alpert, A. A. Nierenberg, M. Spillmann, C. Moore, P. Renshaw, T. Bottiglieri, G. Moroz, and G. Magni. Open study of the catechol-O-methyltransferase inhibitor tolcapone in major depressive disorder. J Clin. Psychopharmacol. 1999, 19, 329.
—in the Field of Schizophrenia:
Weickert, C. S., and D. R. Weinberger. A candidate molecule approach to defining developmental pathology in schizophrenia. Schizophr Bull 1998, 24, 303.
Weinberger, D. R., M. F. Egan, A. Bertolino, J. H. Callicott, V. S. Mattay, B. K. Lipska, K. F. Berman, and T. E. Goldberg. Prefrontal neurons and the genetics of schizophrenia. Biol Psychiatry 2001, 50, 825.
Egan, M. F., T. E. Goldberg, B. S. Kolachana, J. H. Callicott, C. M. Mazzanti, R. E. Straub, D. Goldman, and D. R. Weinberger. Effect of COMT Val108/158 Met genotype on frontal lobe function and risk for schizophrenia. Proc. Natl. Acad. Sci. U S A 2001, 98, 6917
—in the Field of Parkinson's Disease
Two COMT inhibitors are marketed for improvement of levodopa therapy, Tasmar/Tolcapone
M. C. Kurth, C. H. Adler, M. St. Hilaire, C. Singer, C. Waters, P. LeWitt, D. A. Chernik, E. E. Dorflinger, K. Yoo,; Tolcapone improves motor function and reduces levodopa requirement in patients with Parkinson's disease experiencing motor fluctuations: A multicenter, double-blind, randomized, placebo-controlled trial. Neurology, 1997, 48, 81-87;
V. V. Myllylä, M. Jackson, J. P. Larsen, H. Baas, Eur. J Neurol., 1997, 4, 333-341);
Pfeiffer, Ronald F Catechol-O-methyltransferase in Parkinson's disease. Neurological Disease and Therapy (2003), 59(Handbook of Parkinson's Disease (3rd Edition)), 437-451; and Entacapone Gershanik, Oscar; Emre, Murat; Bernhard, Gudrun; Sauer, Dirk. Efficacy and safety of levodopa with entacapone in Parkinson's disease patients suboptimally controlled with levodopa alone, in daily clinical practice: an international, multicentre, open-label study. Progress in Neuro-Psychopharmacology & Biological Psychiatry 2003, 27(6), 963-971.
—in the Field of Cognition Improvement
Lachman, H. M., D. F. Papolos, T. Saito, Y. M. Yu, C. L. Szumlanski, and R. M. Weinshilboum. Human catechol-O-methyltransferase pharmacogenetics: description of a functional polymorphism and its potential application to neuropsychiatric disorders. Pharmacogenetics 1996, 6, 243.
Malhotra, A. K., L. J. Kestler, C. Mazzanti, J. A. Bates, T. Goldberg, and D. Goldman. A functional polymorphism in the COMT gene and performance on a test of prefrontal cognition. Am J Psychiatry 2002, 159, 652.

SUMMARY OF THE INVENTION

The invention provides purine derivatives of formula

I wherein
$R^1$ is H, CN, halogen, —$COR^2$, —$S(O)_xR^2$, $C_{1-12}$-alkyl, $C_{2-12}$-alkenyl, $C_{3-8}$-cycloalkyl, a heterocyclyl group, an aryl group, a heteroaryl group, $C_{3-8}$-cycloalkyl-($C_{1-3}$)-alkyl, a heterocyclyl-($C_{1-3}$)-alkyl group, an aryl-($C_{1-3}$)-alkyl group, or a heteroaryl-($C_{1-3}$)-alkyl group; wherein the alkyl, alkenyl, alkoxy, cycloalkyl, heterocyclyl group, aryl group and heteroaryl groups are optionally substituted;
$R^2$ is —$N(R^3)(R^{3'})$, $C_{1-6}$-alkyl, $C_{3-8}$-cycloalkyl, heterocyclyl, aryl, heteroaryl, $C_{3-8}$-cycloalkyl-($C_{1-3}$)-alkyl, a heterocyclyl-($C_{1-3}$)-alkyl group, an aryl-($C_{1-3}$)-alkyl group, or a heteroaryl-($C_{1-3}$)-alkyl group, wherein the $C_{1-6}$-alkyl, $C_{3-8}$-cycloalkyl, heterocyclyl, aryl, heteroaryl are optionally substituted;
$R^3$ and $R^{3'}$ are independently hydrogen or ($C_{1-3}$)-alkyl;
x is 0, 1 or 2;

and to an ester thereof which is hydrolyzable under physiological conditions and to a pharmaceutically acceptable salt thereof.

The invention also provides processes for the manufacture of compounds of the invention and their pharmaceutically acceptable salts. The invention further provides pharmaceutical compositions containing an effective amount of one or more compounds of formula I per se, or pharmaceutically acceptable salts thereof, and a pharmaceutically acceptable carrier and methods for the manufacture of such compositions.

The compounds of the invention possess valuable pharmacological properties. In particular, these compounds inhibit the enzyme catechol-O-methyltransferase (COMT), a magnesium-dependent enzyme which catalyzes the transfer of the methyl group of S-adenosylmethionine to a catechol substrate, whereby the corresponding methyl ethers are formed. Suitable substrates which can be O-methylated by COMT and which can thus be deactivated are, for example, extraneuronal catecholamines and exogeneously-administered therapeutically active substances having a catechol structure.

The invention also provides methods for the treatment, prevention, or control of illnesses in which a deactivation of extraneuronal catecholamines by COMT plays a role, for example, in the prevention or control of depressions. In this case the compounds of the invention can be used as individual compounds or in combination with other therapeutically active substances which favorably influence the course of the illness. The compounds of the invention can, however, also be used as co-medications with other therapeutically active substances. In addition the compounds of the invention are COMT inhibitors that lack the potential toxicity associated with nitrocatechol containing compounds (K. S.

Smith, P. L. Smith, T. N. Heady, J. M. Trugman, W. D. Harman, T. L. Macdonald, Chem. Res. Toxicol. 2003, 16, 123-128; M. d'Ischia, C. Costantini, Bioorganic & Medicinal Chemistry 1995, 3, 923-927).

The compounds of the invention can also be used for the control of illnesses with therapeutically active substances which have a catechol structure. The treatment of Parkinson's disease and of parkinsonism with L-dopa, a therapeutically active substance having the catechol structure, can be mentioned as an example. In such cases the compounds of formula I can be used in the form of a co-medication or as combination preparations. The compounds of the invention can also be used for the treatment of schizophrenia and to improve cognition.

DETAILED DESCRIPTION OF THE INVENTION

The following definitions of the terms used in the present description shall apply irrespective whether these terms are used alone or in combination. It must be noted that, as used in the specification and the appended claims, the singular forms "a," "an," and "the" include plural forms unless the context clearly dictates otherwise.

The term "alkyl" denotes a straight or branched chain hydrocarbon group. The number of carbon atoms in a given alkyl group is indicated by the numbers listed, for example "$C_{1-12}$-alkyl" indicates an alkyl group with 1 to 12 carbon atoms. Preferred alkyl groups are those with 1 to 6 carbon atoms. Examples of such groups are methyl, ethyl, propyl, isopropyl, butyl, isobutyl, sec.-butyl, tert.-butyl, pentyl, isopentyl, neopentyl, tert.-pentyl, hexyl, isohexyl, 1,1-dimethylbutyl, 2,2-dimethylbutyl, 3,3-dimethylbutyl and 2-ethylbutyl. The alkyl groups may optionally be substituted by halogen, hydroxy, or alkoxy, especially by halogen. Examples of such substituted alkyl groups are, fluoromethyl, difluoromethyl, trifluoromethyl, 2,2,2-trifluoroethyl, trichloromethyl, hydroxymethyl, methoxymethyl, 2-methoxyethyl, and the like.

The term "alkoxy" represent an alkyl-O-group, where the alkyl part is as defined above.

The term "cycloalkyl" represents a saturated cyclic hydrocarbon, preferably a saturated cyclic hydrocarbon having from 3 to 8 carbon atoms, "$C_{3-8}$cycloalkyl." Such cycloalkyl groups include cyclopropyl, cyclobutyl, cyclopentyl, cyclohexyl, cycloheptyl and cyclooctyl; the cycloalkyl group may optionally be substituted by an alkyl group as defined above. Examples of such substituted groups are methylcyclopropyl, ethylcyclopropyl, methylcyclobutyl, methylcyclopentyl, methyl-2-cyclopentenyl, methyl-3-cyclopentenyl or methylcyclohexyl.

The term "alkenyl" represents an unsaturated straight- or branched alkyl chain having one or more double bonds. The term "$C_{2-12}$-alkenyl" represents an alkenyl group containing from 2 to 12 carbon atoms, for example, ethylene, propylene, isopropylene, and the like.

The term "heterocyclyl" represents 3- to 7-membered non-aromatic heterocyclic group containing 1 or 2 hetero atoms selected from nitrogen, oxygen and sulfur or sulfur oxidized to sulfones or sulfoxides. Examples of such groups are oxiranyl, azetidinyl, oxetanyl, thietanyl, pyrrolidinyl, tetrahydrofuryl, thiolanyl, piperidyl, tetrahydropyranyl, morpholinyl, thiomorpholinyl and piperazinyl. Preferred heterocycles are piperidyl and morpholinyl. Such heterocyclic groups may optionally be substituted by alkyl or alkoxy.

The term "aryl" represents an mono- or bicyclic aromatic hydrocarbon group having 6 to 10 carbon atoms, examples of such groups are phenyl or naphthyl, a preferred aryl group is phenyl. These aryl groups may optionally be further substituted by one or several substituents chosen from halogen, alkyl or alkoxy groups as defined above. Examples of such substituted aryl groups are, 2,3 or 4-fluorophenyl, 2,3 or 4-bromophenyl, 2,3 or 4-chlorophenyl, 2,3 or 4-methylphenyl, 2,6- or 3,5-difluorophenyl, 2,6- or 3,5-dichlorophenyl, 2,6- or 3,5-dibromophenyl or 2,6- or 3,5-dimethylphenyl, and the like.

The term "heteroaryl group" represents an aromatic mono- or bicyclic group, wherein each ring contains 5 or 6 members, having 1 to 4 heteroatoms chosen from N, O and S. Examples of such monocyclic aromatic heterocyclic groups include pyridyl, pyrimidinyl, pyridazinyl, pyrrolyl, furanyl, thiophenyl, imidazolyl, pyrazolyl, isoxazolyl, isothiazolyl, thiazolyl, oxazolyl, 1,2,4-oxadiazolyl, 1,2,3-oxadiazolyl, 1,3,4-oxadiazolyl, 1,2,3-thiadiazolyl, 1,2,4-thiadiazolyl, 1,3,4-thiadiazolyl, 1,2,4-triazolyl, 1,3,4-triazolyl, 1,2,3-triazolyl and tetrazolyl; examples of bicyclic heteroaryl groups are benzofuranyl, isobenzofuranyl, benzo[b]thienyl, indolyl, isoindolyl, 1H-indazolyl, benzimidazolyl, benzoxazolyl, benzisoxazolyl, benzothiazolyl, benzisothiazolyl, benzodioxolyl, 1H-benzotriazolyl, quinolyl, isoquinolyl, cinnolinyl, quinazolinyl, quinoxalinyl or phthalazinyl. The "heteroaryl groups" may be further substituted by halogen or an alkyl group as defined above.

"Halogen" stands for fluorine, chlorine, bromine or iodine.

"Pharmaceutically acceptable," such as pharmaceutically acceptable carrier, excipient, etc. means pharmacologically acceptable and substantially non-toxic to the subject to which the particular compound is administered.

"Pharmaceutically acceptable salts" of a compound means salts that are pharmaceutically acceptable, which are generally safe, non-toxic, and neither biologically nor otherwise undesirable, and that possess the desired pharmacological activity of the parent compound. These salts are derived from an inorganic or organic acid or base.

"Pharmaceutically acceptable adjuvant" means a subsidiary ingredient or additive in a mixture of a composition which contributes to the effectiveness of the primary ingredient, such as solubilizers, stabilizing agents, wetting agents, emulsifying agents, flavor-improving agents such as sweetening agents and flavoring agents, coloring agents, salts for varying the osmotic pressure, buffers, coating agents and antioxidants.

"Therapeutically effective amount" means an amount that is effective to prevent, alleviate or ameliorate symptoms of disease or prolong the survival of the subject being treated.

The invention provides purine derivatives of formula

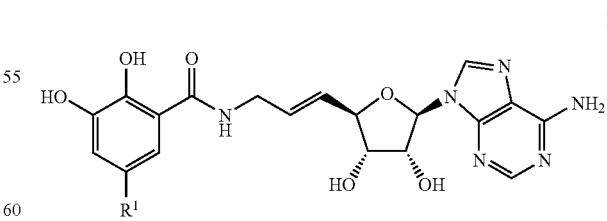

I wherein
$R^1$ is H, CN, halogen, —$COR^2$, —$S(O)_xR^2$, $C_{1-12}$-alkyl, $C_{2-12}$-alkenyl, $C_{3-8}$-cycloalkyl, a heterocyclyl group, an aryl group, a heteroaryl group, $C_{3-8}$-cycloalkyl-($C_{1-3}$)-alkyl, a heterocyclyl-($C_{1-3}$)-alkyl group, an aryl-($C_{1-3}$)- alkyl or a heteroaryl-($C_{1-3}$)-alkyl group; wherein the alkyl, alkenyl, alkoxy, cycloalkyl, heterocyclyl group, aryl and heteroaryl groups are optionally substituted;

$R^2$ is —$N(R^3)(R^{3'})$, $C_{1-6}$-alkyl, $C_{3-8}$-cycloalkyl, heterocyclyl, aryl, heteroaryl, $C_{3-8}$-cycloalkyl-($C_{1-3}$)-alkyl, a heterocyclyl-($C_{1-3}$)-alkyl, an aryl-($C_{1-3}$)-alkyl group, or a heteroaryl-($C_{1-3}$)-alkyl group, wherein the $C_{1-6}$-alkyl, $C_{3-8}$-cycloalkyl, heterocyclyl, aryl, and heteroaryl are optionally substituted;

$R^3$ and $R^{3'}$ are independently hydrogen or ($C_{1-3}$)-alkyl;

x is 0, 1 or 2;

and to an ester thereof which is hydrolyzable under physiological conditions and to a pharmaceutically acceptable salt thereof.

Preferred compounds of formula I are compounds wherein $R^1$ is a hydrogen, cyano, halogen, —$COR^2$, —$S(O)_2R^2$, $C_{1-6}$-alkyl, $C_{1-6}$-alkyl substituted with halogen, $C_{2-6}$-alkenyl substituted with $COR^2$, phenyl, phenyl substituted with $C_{1-6}$-alkyl or halogen, benzyl, benzyl substituted with $C_{1-6}$-alkyl, or heteroaryl. Noninclusive examples of heteroaryl groups are pyridinyl, thiazolyl or benzthiazolyl. Within this group of compounds are preferred compounds wherein $R^2$ is $C_{1-6}$-alkyl, $C_{1-6}$-alkyl substituted with halogen or —$N(R^3)(R^{3'})$ and wherein $R^3$ and $R^{3'}$ are independently $C_{1-3}$-alkyl. Another such group of preferred compounds are those wherein $R^2$ is phenyl, phenyl substituted with $C_{1-6}$-alkyl or halogen, cyclohexyl, or heteroaryl such as pyridinyl, thiazolyl or benzthiazolyl.

Preferred compounds are the compounds of formula I wherein $R^1$ is hydrogen, cyano, or halogen, such as for example N-{3-[5-(6-Amino-purin-9-yl)-3,4-dihydroxy-tetrahydrofuran-2-yl]-allyl}-2,3-dihydroxy-benzamide (Example 1);

N-{3-[5-(6-Amino-purin-9-yl)-3,4-dihydroxy-tetrahydrofuran-2-yl]-allyl}-5-cyano-2,3-dihydroxy-benzamide (Example 3);

N-{3-[5-(6-Amino-purin-9-yl)-3,4-dihydroxy-tetrahydrofuran-2-yl]-allyl}-5-bromo-2,3-dihydroxy-benzamide (Example 2); and N-{3-[5-(6-Amino-purin-9-yl)-3,4-dihydroxy-tetrahydrofuran-2-yl]-allyl}-5-chloro-2,3-dihydroxy-benzamide (Example 7).

Further preferred compounds are the compounds of formula I wherein $R^1$ is $C_{1-6}$-alkyl, $C_{1-6}$-alkyl substituted with halogen, $C_{2-6}$-alkenyl substituted with $COR^2$, wherein $R^2$ is —$N(R^3)(R^{3'})$ and wherein $R^3$ and $R^{3'}$ are independently $C_{1-3}$-alkyl, such as for example N-{3-[5-(6-Amino-purin-9-yl)-3,4-dihydroxy-tetrahydrofuran-2-yl]-allyl}-2,3-dihydroxy-5-isopropyl-benzamide (Example 17);

N-{3-[5-(6-Amino-purin-9-yl)-3,4-dihydroxy-tetrahydrofuran-2-yl]-allyl}-5-(2-dihydroxy-carbamoyl-vinyl)-2,3-dihydroxy-benzamide (Example 15); and N-{3-[5-(6-Amino-purin-9-yl)-3,4-dihydroxy-tetrahydrofuran-2-yl]-allyl}-2,3-dihydroxy-5-trifluoromethyl-benzamide (Example 16).

A further group of preferred compounds are compounds of formula I wherein $R^1$ is —$COR^2$. Within this group of compounds, preferred compounds are those wherein $R^2$ is $C_{1-6}$-alkyl, $C_{1-6}$-alkyl substituted with halogen, —$N(R^3)(R^{3'})$ and wherein $R^3$ and $R^{3'}$ are independently $C_{1-3}$-alkyl, such compounds are for example N-{3-[5-(6-Amino-purin-9-yl)-3,4-dihydroxy-tetrahydrofuran-2-yl]-allyl}-2,3-dihydroxy-5-trifluoroacetyl-benzamide (Example 4) and N3-{3-[5-(6-Amino-purin-9-yl)-3,4-dihydroxy-tetrahydrofuran-2-yl]-allyl}-4,5-dihydroxy-N1,N1-dimethyl-isophthalamide (Example 14).

A further group of preferred compounds of formula I wherein $R^1$ is —$COR^2$ are those wherein $R^2$ is phenyl, phenyl substituted with $C_{1-6}$-alkyl or halogen, $C_{3-8}$-cycloalkyl, or heteroaryl such as pyridinyl, thiazolyl or benzthiazolyl, for example N-{3-[5-(6-Amino-purin-9-yl)-3,4-dihydroxy-tetrahydrofuran-2-yl]-allyl}-2,3-dihydroxy-5-(4-methyl-benzoyl)-benzamide (Example 19);

N-{3-[5-(6-Amino-purin-9-yl)-3,4-dihydroxy-tetrahydrofuran-2-yl]-allyl}-5-cyclohexanecarbonyl-2,3-dihydroxy-benzamide (Example 6); and N-{3-[5-(6-Amino-purin-9-yl)-3,4-dihydroxy-tetrahydrofuran-2-yl]-allyl}-2,3-dihydroxy-5-(pyridine-4-carbonyl)-benzamide (Example 5).

A further preferred group of compounds are the compounds of formula I wherein $R^1$ is —$S(O)_2R^2$. Preferred compounds within this group of compounds are those wherein $R^2$ is $C_{1-6}$-alkyl, $C_{1-6}$-alkyl substituted with halogen, —$N(R^3)(R^{3'})$ and wherein $R^3$ and $R^{3'}$ are independently $C_{1-3}$-alkyl. Also preferred within this group of compounds are those wherein $R^2$ is phenyl, phenyl substituted with $C_{1-6}$-alkyl or halogen, cyclohexyl, or heteroaryl such as pyridinyl, thiazolyl or benzthiazolyl, for example N-{3-[5-(6-Amino-purin-9-yl)-3,4-dihydroxy-tetrahydrofuran-2-yl]-allyl}-2,3-dihydroxy-5-(toluene-4-sulfonyl)-benzamide (Example 18).

A further preferred group of compounds are the compounds of formula I wherein $R^1$ is phenyl, phenyl substituted with $C_{1-6}$-alkyl or halogen, pyridinyl, thiazolyl, benzthiazolyl, benzyl, or benzyl substituted with $C_{1-6}$-alkyl, such as for example 4'-Fluoro-4,5-dihydroxy-biphenyl-3-carboxylic acid {3-[5-(6-amino-purin-9-yl)-3,4-dihydroxy-tetrahydro-furan-2-yl]-allyl}-amide (Example 8);

N-{3-[5-(6-Amino-purin-9-yl)-3,4-dihydroxy-tetrahydrofuran-2-yl]-allyl}-2,3-dihydroxy-5-thiazol-2-yl-benzamide (Example 10);

N-{3-[5-(6-Amino-purin-9-yl)-3,4-dihydroxy-tetrahydrofuran-2-yl]-allyl}-2,3-dihydroxy-5-pyridin-4-yl-benzamide (Example 12);

4,5-Dihydroxy-4'-methyl-biphenyl-3-carboxylic acid {3-[5-(6-amino-purin-9-yl)-3,4-dihydroxy-tetrahydro-furan-2-yl]-allyl}-amide (Example 9);

N-{3-[5-(6-Amino-purin-9-yl)-3,4-dihydroxy-tetrahydrofuran-2-yl]-allyl}-5-benzothiazol-2-yl-2,3-dihydroxy-benzamide (Example 11); and N-{3-[5-(6-Amino-purin-9-yl)-3,4-dihydroxy-tetrahydrofuran-2-yl]-allyl}-2,3-dihydroxy-5-(4-methyl-benzyl)-benzamide (Example 13).

The present compounds of formula I and their pharmaceutically acceptable salts can be prepared by methods known in the art, for example, by process described below, which process comprises a) reacting 9-{(3aR,4R,6R,6aR)-6-[(E)-3-aminoprop-1-enyl]-2,2-dimethylperhydrofuro[3,4-d][1,3] di-oxol-4-yl}-9H-purin-6-amine of formula II

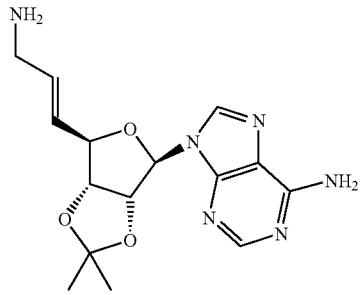

II with an optionally protected 2,3-dihydroxy-benzoic acid derivative substituted by R¹ in position 5

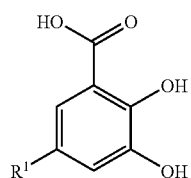

IIIa

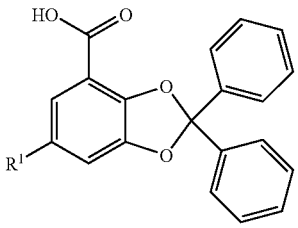

IIIb wherein R¹ is as defined above in the presence of (3-dimethylamino-propyl)-ethyl-carbodiimide (EDC), triethyl amine and N-hydroxy-succinimide (HOSu) in a suitable solvent such as dichloroethylene and b) subsequent deprotection of the hydroxy groups where necessary with trifluoroacetic acid in an aqueous solution to form the compounds of formula I.

The amino-purine derivative of formula II can be prepared according to Scheme 1 starting from 2-(6-Amino-purin-9-yl)-5-hydroxymethyl-tetrahydro-furan-3,4-diol (1) which is protected and subsequently reacted with (triphenyl-phosphanylidene)-acetic acid ethyl ester to the ester (4). The ester group in compound (4) is reduced to the alcohol (5) and transformed into the amide of formula II

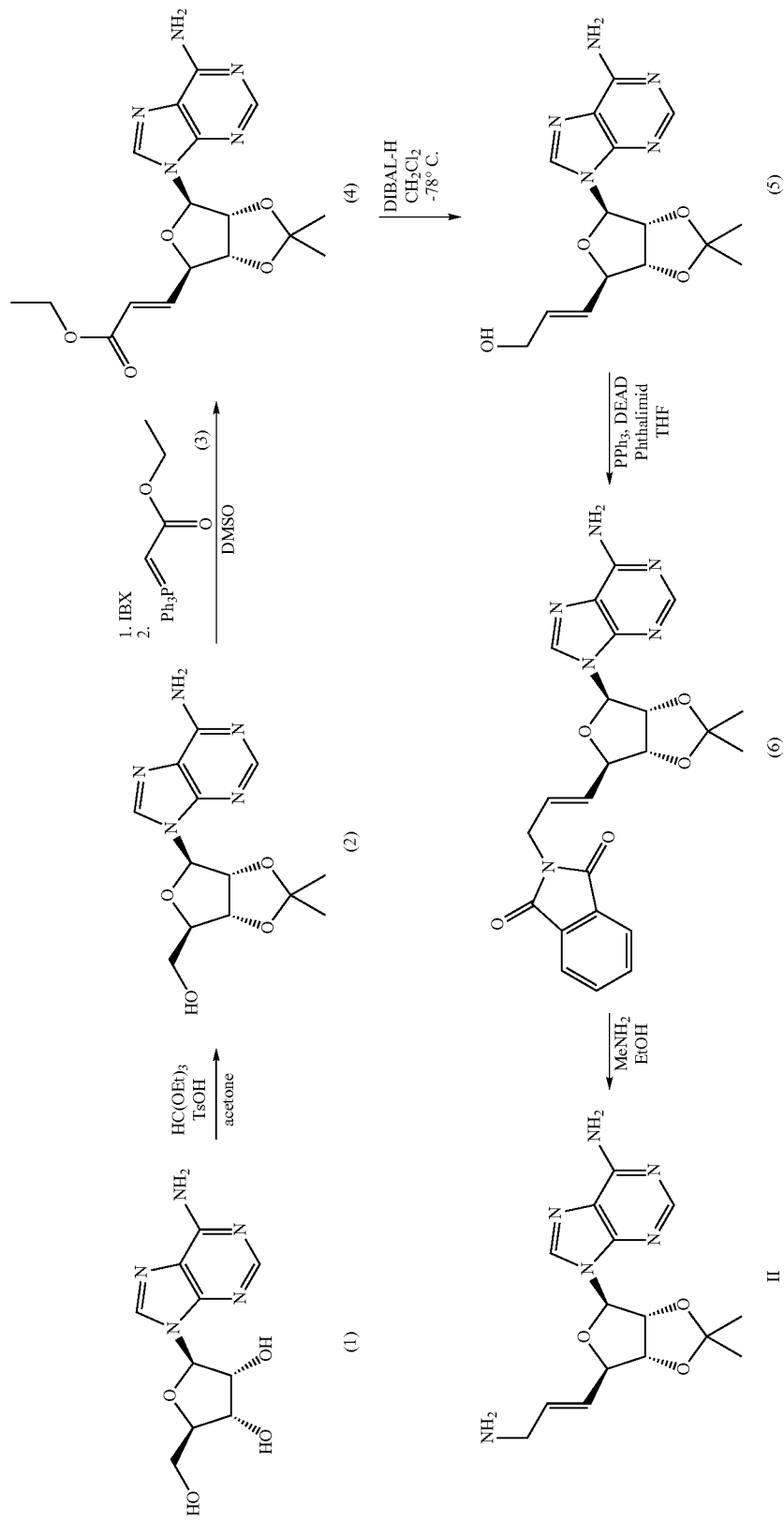

wherein TsOH stand for tosylchloride, IBX for 1-hydroxy-1,2-benziodoxol-3(1H)-1-oxide, DMSO for dimethylsulfoxide, PPh$_3$ for triphenylphosphine, DEAD for diethyl azodicarboxylate and THF for tetrahydrofurane, Angew. Chem. (2001) 113, 4164.

The optionally protected 2,3-dihydroxy-benzoic acid derivatives substituted by R$^1$ in position 5 (IIIa and IIIb) are prepared according to reaction schemes 2 to 6.

A method for the preparation of compounds of formula IIIb, wherein R$^1$ is hydrogen or bromine is given in Scheme 2.

step b) protection of the ester (8) by ketalisation of the two hydroxy groups with a suitable ketone, e.g. with dichlorodiphenylmethane;

step c) hydrolysation of the ester group in the presence of a strong base such a LiOH.

step d) 2,3-dihydroxy-benzoic acid is brominated in acetic acid and in the following steps e) to g) the carboxylic group is esterified to form the ester (11), the two hydroxy groups

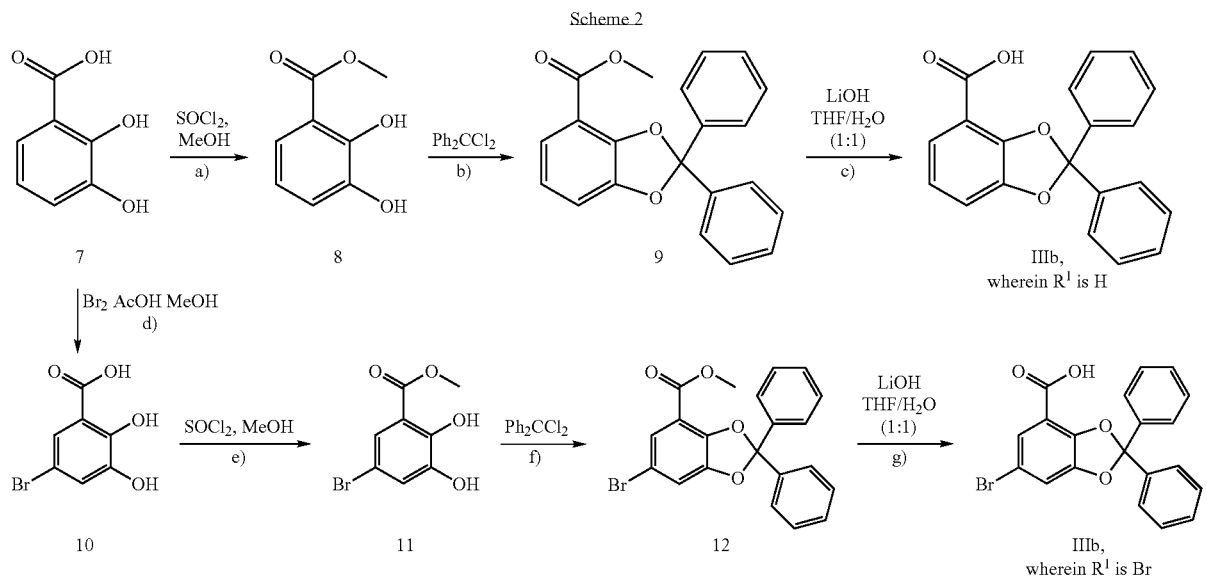

step a) esterification of 2,3-dihydroxy-benzoic acid (7) dissolved in a suitable solvent for example an alcohol such as methanol in the presense of thionylchloride to form the ester (8);

are protected to form the ketal (12) and the ester group is cleaved as described for steps a) to c).

The compounds of formula IIIb wherein R$^1$ is chlorine can be prepared as depicted in Scheme 3.

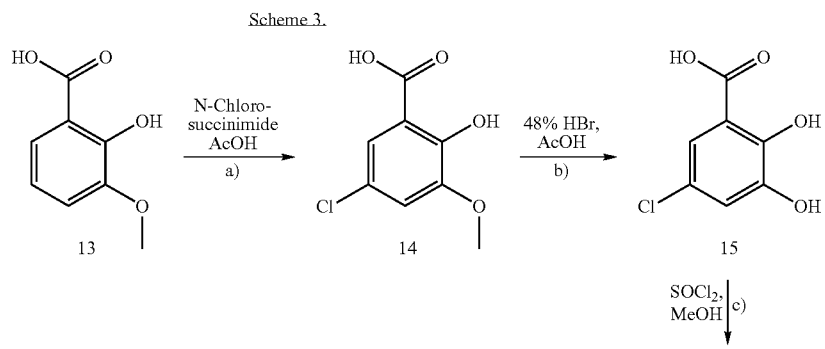

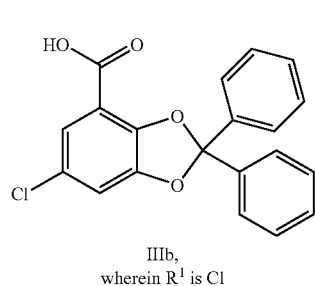

IIIb,
wherein R¹ is Cl

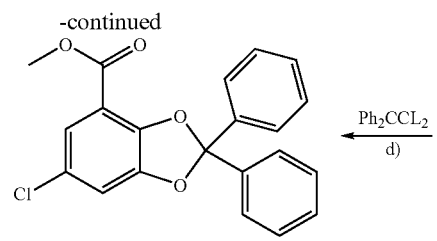

17

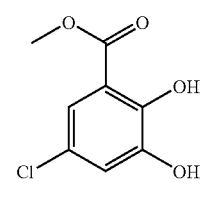

16 step a) 2-hydroxy-3-methoxy-benzoic acid (13) is chlorinated for example with N-chlorosuccinimide in acetic acid to yield 5-chloro-2-hydroxy-3-methoxy benzoic acid (14);

step b) the methoxy group of compound (14) is reacted with hydrobromic acid in acetic acid to yield 5-chloro-2,3-dihydroxybenzoic acid (15);

5-chloro-2,3-dihydroxy benzoic acid is then transformed into the protected compounds IIIb, wherein R¹ is chlorine by esterification of the carboxylic group, ketalisation of the two hydroxy groups and subsequent cleavage of the ester group (steps c) to e)) as described above.

Scheme 4 describes the preparation of derivatives of formula IIIb, wherein R¹ is —COR² and R² is trifluoromethyl, cyclohexyl or pyridin-4-yl. The protected 5-bromobenzoic acid derivative (the compound of formula IIIb, wherein R¹ is bromine) is converted to its lithium salt. Lithium-halogen exchange and reaction with ethyl-trifluoroacetate, cyclohexane carboxylic acid methoxymethylamide, or pyridine-4-carbaldehyde followed by oxidation with IBX yielded the corresponding derivatives of formula IIIb.

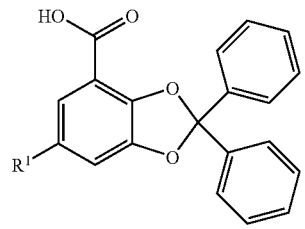

IIIb,
wherein R¹ is for example a group selected from

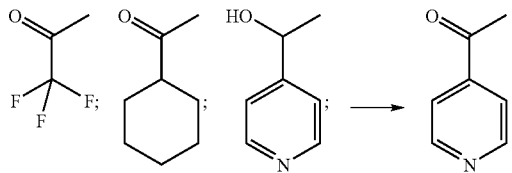

In Scheme 5 the preparation of further derivatives of formula IIIb starting from protected 5-bromo benzoic acid ester (12) is shown. The nitrile is obtained by Pd catalysed cyanation. Arylsubstitutents were introduced using a Pd catalysed Suzuki-coupling with arylboronic acids.

Scheme 4

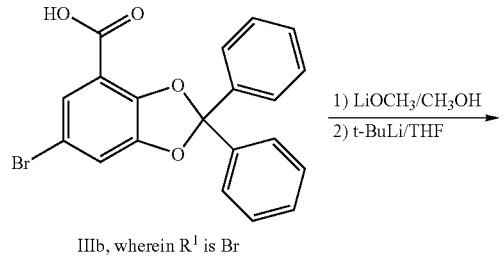

IIIb, wherein R¹ is Br

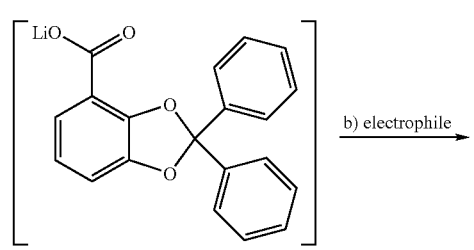

Scheme 5

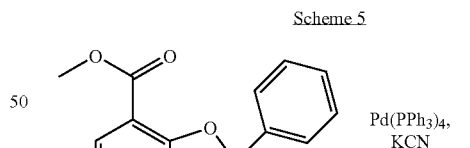

12

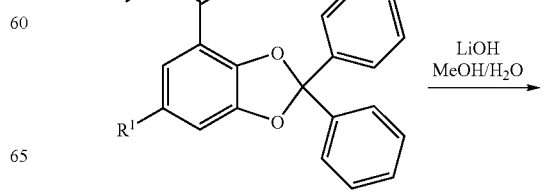

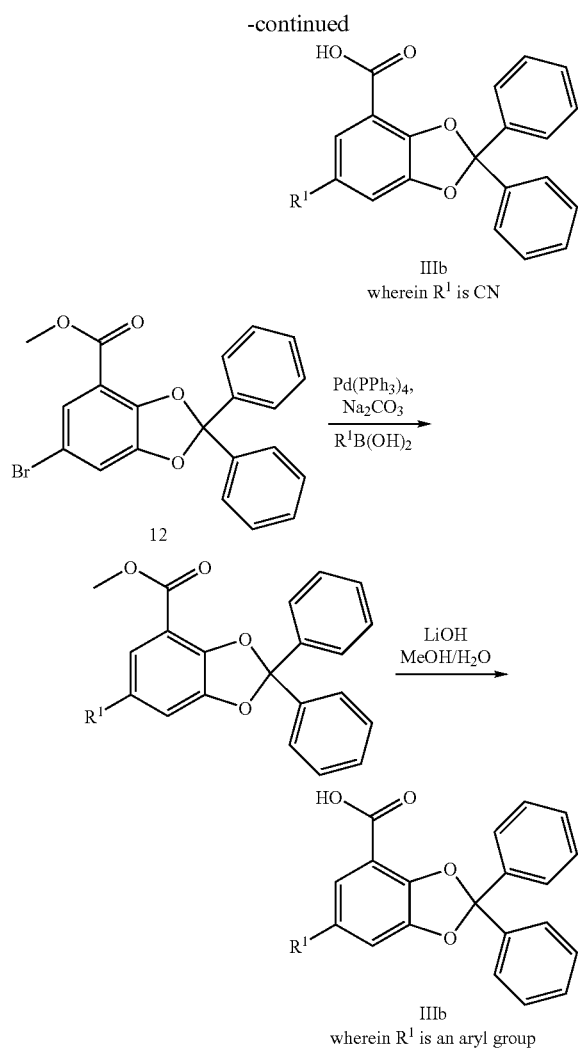
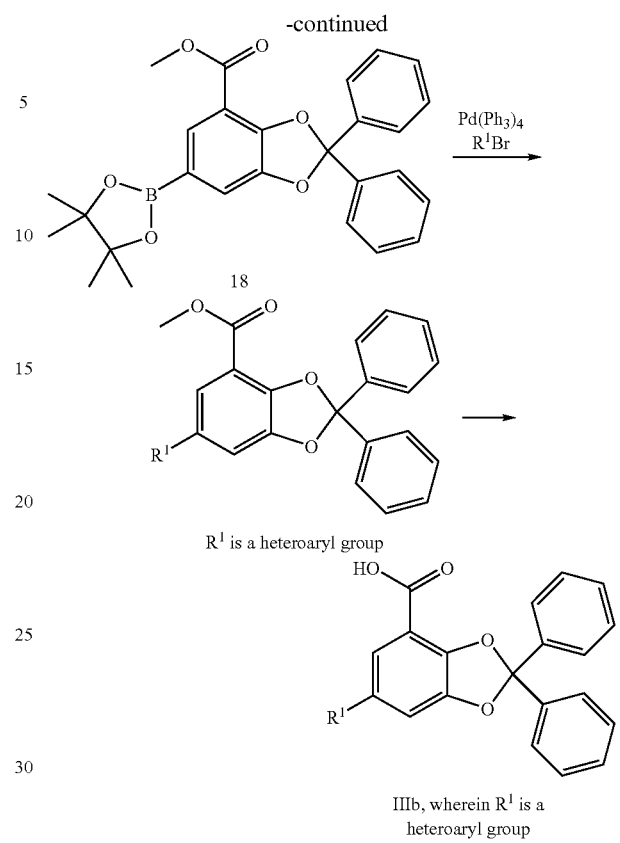

In Scheme 6 the preparation of several derivatives of formula IIIb starting from protected 5-bromo benzoic acid derivative (12) is shown. 5-Bromo benzoic acid ester (12) is first converted to the dioxaborolane (18) which is subsequently reacted with benzylbromides, bromo aryl or bromo heteroaryl compounds in a palladium catalysed Suzuki reaction to yield the corresponding derivatives IIIb.

Scheme 6

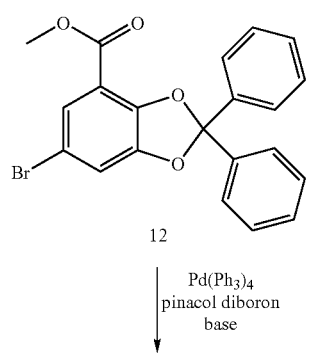

In analogy to schemes 2, 3, 4, 5 and 6, compounds of formula I may be prepared, wherein $R^1$ is other than those as described in the above schemes.

The various compounds which are used as starting materials are known or can be prepared according to known methods.

As mentioned earlier, the compounds of formula I inhibit the enzyme COMT. The inhibitory activity can be determined in vitro with COMT obtained from rat liver. Rat liver homogenate is incubated in the presence of a suitable substrate as described by Zürcher et al. in J. Neurochem. 1982, 38, 191-195 and the COMT activity is measured.

The IC50 values (concentration of the inhibitor at which 50% activity of the enzyme is observed) were determined in a radiochemical assay described by Zürcher et al. (see above) and are listed in Table 1.

$IC_{50}$ values were determined as follows: The inhibitors were dissolved in $Me_2SO$ as 1.2 mM stock solution and further diluted with $Me_2SO$. The reactions were performed in standard polypropylene vials. 25 µl of the inhibitor in varying concentrations from $10^{-4}$ to $10^{-9}$ mol $L^{-1}$ were mixed with 215 µl freshly prepared buffer-substrate mixture consisting of 170 µl potassium phosphate buffer (0.1 mol $L^{-1}$, pH 7.6), 10 µl $MgCl_2$, (0.1 mol $L^{-1}$), 10 µl dithiothreitol (0.065 mol $L^{-1}$) and 25 µl of tissue extract. The enzyme preparations were preincubated for 15 min at 37° C. The reaction was started by adding 30 µl substrate (benzene-1, 2-diol, 0.025 mol $L^{-1}$), 10 µl [$^3$H]SAM (5.5 mmol $L^{-1}$, specific activity: 13.36 Bq mol$^{-1}$ (3.61 Cimol$^{-1}$) and 20 µl deionized $H_2O$, reaching a final substrate concentration of 2.5 mM and a final [$^1$H]/[$^3$H]SAM concentration of 183 µM. The reaction was stopped after incubating the vials in a water-bath at 37° C. for 15 min by addition of 200 μl HOAc (5.7%) containing guaiacol (0.1 g $L^{-1}$). The reaction vessels were transferred into polyethylene scintillation vials and 3 ml of scintillation fluid (5 g butyl-PBD, dissolved in 200 ml toluene, made up to 1 L with n-hexane) was added. The vials were capped and more than 98% [$^3$H]guajacol formed was extracted into the organic phase by vigorous shaking for 3 min.

The samples were counted in a Beckmann LS 6000 TA scintillation counter.

TABLE 1

| Example | | IC50 [nM] |
|---|---|---|
| comparative example | N-{3-[5-(6-Amino-purin-9-yl)-3,4-dihydroxy-tetrahydro-furan-2-yl]-allyl}-2,3-dihydroxy-5-nitro-benzamide | 9 |
| 1 | N-{3-[5-(6-Amino-purin-9-yl)-3,4-dihydroxy-tetrahydro-furan-2-yl]-allyl}-2,3-dihydroxy-benzamide | 2600 |
| 2 | N-{3-[5-(6-Amino-purin-9-yl)-3,4-dihydroxy-tetrahydro-furan-2-yl]-allyl}-5-bromo-2,3-dihydroxy-benzamide | 28 |
| 3 | N-{3-[5-(6-Amino-purin-9-yl)-3,4-dihydroxy-tetrahydro-furan-2-yl]-allyl}-5-cyano-2,3-dihydroxy-benzamide | 29 |
| 4 | N-{3-[5-(6-Amino-purin-9-yl)-3,4-dihydroxy-tetrahydro-furan-2-yl]-allyl}-2,3-dihydroxy-5-trifluoroacetyl-benzamide | 39 |
| 5 | N-{3-[5-(6-Amino-purin-9-yl)-3,4-dihydroxy-tetrahydro-furan-2-yl]-allyl}-2,3-dihydroxy-5-(pyridine-4-carbonyl)-benzamide | 42 |
| 6 | N-{3-[5-(6-Amino-purin-9-yl)-3,4-dihydroxy-tetrahydro-furan-2-yl]-allyl}-5-cyclohexanecarbonyl-2,3-dihydroxy-benzamide | 83 |
| 7 | N-{3-[5-(6-Amino-purin-9-yl)-3,4-dihydroxy-tetrahydro-furan-2-yl]-allyl}-5-chloro-2,3-dihydroxy-benzamide | 44 |
| 8 | 4'-Fluoro-4,5-dihydroxy-biphenyl-3-carboxylic acid {3-[5-(6-amino-purin-9-yl)-3,4-dihydroxy-tetrahydro-furan-2-yl]-allyl}-amide | 21 |
| 9 | 4,5-Dihydroxy-4'-methyl-biphenyl-3-carboxylic acid {3-[5-(6-amino-purin-9-yl)-3,4-dihydroxy-tetrahydro-furan-2-yl]-allyl}-amide | 23 |
| 10 | N-{3-[5-(6-Amino-purin-9-yl)-3,4-dihydroxy-tetrahydro-furan-2-yl]-allyl}-2,3-dihydroxy-5-thiazol-2-yl-benzamide | 27 |
| 11 | N-{3-[5-(6-Amino-purin-9-yl)-3,4-dihydroxy-tetrahydro-furan-2-yl]-allyl}-5-benzothiazol-2-yl-2,3-dihydroxy-benzamide | 29 |
| 12 | N-{3-[5-(6-Amino-purin-9-yl)-3,4-dihydroxy-tetrahydro-furan-2-yl]-allyl}-2,3-dihydroxy-5-pyridin-4-yl-benzamide | 23 |
| 13 | N-{3-[5-(6-Amino-purin-9-yl)-3,4-dihydroxy-tetrahydro-furan-2-yl]-allyl}-2,3-dihydroxy-5-(4-methyl-benzyl)-benzamide | 608 |
| 14 | N3-{3-[5-(6-Amino-purin-9-yl)-3,4-dihydroxy-tetrahydro-furan-2-yl]-allyl}-4,5-dihydroxy-N1,N1-dimethyl-isophthalamide | 2000 |
| 15 | N-{3-[5-(6-Amino-purin-9-yl)-3,4-dihydroxy-tetrahydro-furan-2-yl]-allyl}-5-(2-dimethyl-carbamoyl-vinyl)-2,3-dihydroxy-benzamide | 97 |
| 16 | N-{3-[5-(6-Amino-purin-9-yl)-3,4-dihydroxy-tetrahydro-furan-2-yl]-allyl}-2,3-dihydroxy-5-trifluoromethyl-benzamide | 35 |
| 17 | N-{3-[5-(6-Amino-purin-9-yl)-3,4-dihydroxy-tetrahydro-furan-2-yl]-allyl}-2,3-dihydroxy-5-isopropyl-benzamide | 1370 |
| 18 | N-{3-[5-(6-Amino-purin-9-yl)-3,4-dihydroxy-tetrahydro-furan-2-yl]-allyl}-2,3-dihydroxy-5-(toluene-4-sulfonyl)-benzamide | 213 |
| 19 | N-{3-[5-(6-Amino-purin-9-yl)-3,4-dihydroxy-tetrahydro-furan-2-yl]-allyl}-2,3-dihydroxy-5-(4-methyl-benzoyl)-benzamide | 34 |

The present invention also provides pharmaceutical compositions containing an effective amount of one or more compounds of the invention or esters, ethers, or pharmaceutically acceptable salts thereof and a pharmaceutically acceptable carrier.

Suitable pharmaceutically acceptable carriers include non-toxic, pharmaceutically inert, inorganic or organic carriers. Suitable carriers for tablets, coated tablets, dragees and hard gelatin capsules are, for example, lactose, maize starch or derivatives thereof, talc, stearic acid or its salts. Suitable carriers for soft gelatin capsules are, for example, vegetable oils, waxes, fats and semi-solid and liquid polyols. Depending on the nature of the active substances no carriers are, however, required in the case of soft gelatin capsules. Suitable carrier materials for the preparation of solutions and syrups are, for example, water, polyols, saccharose, invert sugar and glucose. Suitable carrier materials for injection solutions are, for example, water, alcohols, polyols, glycerine and vegetable oils. Suitable carrier materials for suppositories are, for example natural or hardened oils, waxes, fats and semi-liquid or liquid polyols.

The pharmaceutical compositions of the invention also can contain pharmaceutical adjuvants. As pharmaceutical adjuvants there come into consideration the usual preserving agents, solubilizers, stabilizing agents, wetting agents, emulsifying agents, flavor-improving agents such as sweetening agents and flavoring agents, coloring agents, salts for varying the osmotic pressure, buffers, coating agents and antioxidants.

The pharmaceutical compositions of the invention conveniently contain about 25 mg to about 300 mg, preferably about 50 mg to about 150 mg, of a compound of the invention, for example, a compound of formula I or an ester thereof which is hydrolyzable under physiological conditions or of a pharmaceutically acceptable salt thereof.

The present invention also provides a process for the manufacture of pharmaceutical compositions. Such process comprises bringing one or more compounds of the invention and, if desired, one or more therapeutically valuable substances into a galenical administration form with one or more pharmaceutically acceptable carriers and, if desired, one or more pharmaceutical adjuvants.

Compounds of the invention inhibit the enzyme catechol-O-methyltransferase (COMT). Thus, the invention provides methods for the treatment, prevention, or control of illnesses in which a deactivation of extraneuronal catecholamines by COMT plays a role, for example, in the prevention or control of depressions. In this case the compounds of the invention can be used as individual compounds or in combination with other therapeutically active substances which favorably influence the course of the illness. The compounds of the invention can, also be used as co-medications with other therapeutically active substances. In addition the compounds of the invention are COMT inhibitors that lack the potential toxicity associated with nitrocatechol containing compounds (K. S. Smith, P. L. Smith, T. N. Heady, J. M. Trugman, W. D. Harman, T. L. Macdonald, Chem. Res. Toxicol. 2003, 16, 123-128; M. d'Ischia, C. Costantini, Bioorganic & Medicinal Chemistry 1995, 3, 923-927).

The compounds of the invention can also be used for the control of illnesses with therapeutically active substances which have a catechol structure. The treatment of Parkinson's disease and of parkinsonism with L-dopa, a therapeutically active substance having the catechol structure, can be mentioned as an example. In such cases the compounds of formula I can be used in the form of a co-medication or as combination preparations. The compounds of the invention can also be used for the treatment of schizophrenia and to improve cognition.

Therefore, the invention provides a method for the treatment of depression which comprises administering to an individual a therapeutically effective amount of a compound of the invention, for example a compound of formula I. The invention also provides a method for the treatment of Parkinson's disease which comprises administering to an individual a therapeutically effective amount of a compound of the invention, for example a compound of formula I. The invention further provides a method for the treatment of schizophrenia which comprises administering to an individual a therapeutically effective amount of a compound of the invention, for example a compound of formula I. The invention provides a method for improving cognition which comprises administering to an individual an effective amount of a compound of the invention, for example a compound of formula I.

The compound and compositions of the invention can be administered in a conventional manner, for example, orally, rectally, or parenterally. The pharmaceutical compositions of the invention can be administered orally, for example, in the form of tablets, coated tablets, dragees, hard and soft gelatin capsules, solutions, emulsions, or suspensions. The pharmaceutical compositions also can be administered rectally, for example, in the form of suppositories or parenterally, for example, in the form of injectable solutions.

The dosage at which compounds of the invention, or ester derivatives thereof and salts thereof can vary within wide limits depending on the illness to be treated, the age and the individual condition of the patient and on the mode of administration and will, of course, be fitted to the individual requirements in each particular case. For example, in the improvement of the treatment with or without L-dopa a daily dosage of 25 mg to about 1000 mg, especially about 100 mg to about 300 mg, comes into consideration. Depending on the dosage it is convenient to administer the daily dosage in several dosage units.

The Examples which follow will further illustrate the invention and contain detailed information concerning the preparation of compounds of formula I and the used starting materials.

Experimental

Materials and Methods

Solvents for extractions and chromatography were of technical grade and were distilled prior to usage. Reactions were performed using solvents of p.a. grade purchased from Fluka or J. T Baker or solvents of comparable quality. THF (tetrahydrofuran) was distilled from sodium benzophenone ketyl and $CH_2Cl_2$ from $CaH_2$.

Thin layer chromatography was performed on aluminum-backed sheets coated with $SiO_2$ 60 $F_{254}$ from Macherey-Nagel using UV-light (254 nm) for detection. Column chromatography was performed using Fluka $SiO_2$ 60, 40-63 mesh, at r.t. (room temperature) and at a pressure of $1 \cdot 10^6$ to $4 \cdot 10^6$ Pa (0.1-0.4 bar).

Analytical HPLC was performed on a Merck LiChrospher® 100 RP-18 (250×4 mm, 5 µm, 100 Å) column, using a linear gradient of $CH_3CN$ in $H_2O$ with 0.1% TFA (trifluoro acetic acid), 5→55% in 20 min, a flow of 1 mL/min, and UV-detection at 254 nm.

Preparative HPLC was performed on a Merck LiChrosorb® RP-18 (250×25 mm, 7 µm) column, using a linear gradient of $CH_3CN$ in $H_2O$ with 0.1% TFA, a flow of 10 mL/min and UV-detection at 254 nm.

Melting points were determined on a Büchi-510 apparatus and are uncorrected. Infrared spectra were recorded on a Perkin-Elmer 1600-FT spectrometer.

NMR spectra ($^1H$ and $^{13}C$) were recorded at r.t. on Varian-Mercury 300 or Bruker AMX-500 instruments.

Mass Spectra were recorded by the MS service of the Labortorium für Organische Chemie at ETH Zürich using IonSpec Ultima (MALDI, with 2,5-dihydroxybenzoic acid or 2,4,6-trihy-droxyacetophenone/diammonium citrate 2:1 as matrix) and VG-TRIBID (EI) spectrometers.

Elemental analyses were performed by the Mikrolabor of the Laboratorium für Organische Chemie at ETH Zürich.

General Procedures (GP)

General Procedure 1 (GP1) for the Synthesis of methyl 2,3-dihydroxybenzoate Derivatives from the Corresponding 2,3-dihydroxybenzoic acids To a solution of the 2,3-dihydroxy-benzoic acid (1 eq.) in MeOH was slowly added $SOCl_2$ (3 eq.) via a syringe and the reaction mixture was then refluxed overnight. After evaporation of the solvent under reduced pressure the grayish solid was redissolved in EtOAc and washed twice with saturated $K_2CO_3$ solution, then saturated NaCl solution before being dried over $MgSO_4$ and the solvent evaporated in vacuo. Drying under high vacuum yielded the product as a grayish solid.

General Procedure (GP2) for the Protection of Catechols as diarylmethylketals

General Procedure 2.1 (GP2.1) Protection as diphenylmethylketal.

Method A. A suspension of the corresponding methyl 2,3-dihydroxybenzoate (1 eq.) in dichlorodiphenylmethane (1.5 eq.) was stirred at 160° C. for 40 min. After cooling to 50° C., 30 mL MeOH was added to the viscous brown oil leading to the formation of a precipitate. The precipitate was filtered, washed with MeOH (3×20 mL) and dried under high vacuum to yield the desired compound as a colorless solid.

Method B. A suspension of the corresponding methyl 2,3-dihydroxybenzoate (1 eq.) in 3.7 mL dichlorodiphenyl-methane (1.5 eq.) was stirred at 160° C. for 40 min. After cooling, EtOAc was added to the viscous mixture and the solution was washed with saturated NaCl solution, dried over $MgSO_4$ and evaporated under reduced pressure. The crude product was purified using flash chromatography (silica gel, hexane/$Et_2O$ 10:1) to yield the desired compound as a colorless solid.

General Procedure 2.2 (GP2.2) Protection as 4,4'-dimethoxy-diphenylmethylketal.

4,4'-Dimethoxybenzophenone (1.5 eq.) and oxalyl chloride (8 eq.) were stirred at 60° C. for 30 min., then the temperature was raised to 1 10° C. to remove the excess oxalyl chloride and the corresponding methyl 2,3-dihydroxy-benzoate (1 eq.) was added to the reaction mixture. The dark red solution was stirred at 160° C. for 40 min. After cooling, EtOAc was added to the viscous mixture and the solution was washed with saturated NaCl solution, dried over $MgSO_4$ and evaporated under reduced pressure. The crude product was purified using flash chromatography (silica gel, hexane/$Et_2O$ 10:1 or hexane/EtOAc 20:1).

General Procedure 3 (GP3) for the Synthesis of Catechol Carboxylic Acids from the Corresponding Ester Precursors The biphasic mixture of a solution of the methyl catechol carboxylate (1 eq.) in 5 mL THF and a solution of LiOH.H$_2$O (3 eq.) in 5 mL H$_2$O was refluxed for 3 h. After cooling to r.t. the reaction mixture was acidified by addition of 4 mL 10% AcOH—solution and poured into a separatory funnel containing 50 mL H$_2$O and 50 mL EtOAc. The layers were separated and the aqueous layer was extracted twice with 20 mL EtOAc. The pooled organic fractions were washed twice with saturated NaCl-solution before being dried over MgSO$_4$ and evaporated in vacuo to yield the desired compound as a colorless solid.

General Procedure 4 (GP4) for the Synthesis of Functionalized Catechol Carboxylic Acids Starting from 6-bromo-2, 2-diphenyl-1,3-benzodioxole-4-carboxylic acid Method A. To a suspension of 6-bromo-2,2-diphenyl-1, 3-benzodioxole-4-carboxylic acid (1 eq.) in 3 mL MeOH, LiOMe (2 eq.) was added leading to the formation of a clear solution, which was stirred 20 min. at r.t. Following evaporation of the solvent under reduced pressure, the resulting white foam was dried overnight under vacuum. The residue was then redissolved in 10 mL dry THF and cooled to −78° C. To this solution t-BuLi (1.5M solution in pentane, 2.5 eq.) was added dropwise via a syringe and the resulting dark yellow solution was stirred 30 min. at −78° C. The desired electrophile was added to the reaction mixture and the stirring continued 30 min. at low temperature. The cooling bath was removed and the reaction was stirred another 2 h at r.t., followed by acidification with 10% AcOH-solution and extraction with EtOAc (2×30 mL). The organic fractions were pooled, dried over MgSO$_4$ and the solvent evaporated in vacuo. The crude product was purified using flash chromatography (silica gel, hexane/EtOAc/AcOH) to give the title compound as a yellowish to colorless solid.

Method B. To a solution of 6-bromo-2,2-diphenyl-1,3-benzodioxole-4-carboxylic acid (1 eq.) in 8 mL dry THF, LiH (2 eq.) was added. The reaction mixture was stirred 15 min. at r.t., then cooled to −78° C. To this solution t-BuLi (1.5M solution in pentane, 2.5 eq.) was added dropwise via a syringe and the resulting yellow solution was stirred 30 min. at −78° C. The desired electrophile was added to the reaction mixture and the stirring continued 30 min. at low temperature. The cooling bath was removed and the reaction was stirred another 2 h at r.t., followed by acidification with 10% AcOH-solution and extraction with EtOAc (2×30 mL). The organic fractions were pooled, dried over MgSO$_4$ and the solvent evaporated in vacuo. The crude product was purified using flash chromatography (silica gel, hexane/EtOAc/AcOH) to give the desired compound as a colorless solid.

General Procedure 5 (GP5) for the Synthesis of Biaryl Catechol Carboxylic Esters via Suzuki Reaction Between methyl 6-bromo-2,2-diphenyl-1,3-benzodioxole-4-carboxylate and the Corresponding Aryl Boronic Acid To a solution of methyl 6-bromo-2,2-diphenyl-1,3-benzodioxole-4-carboxylate (1 eq.) and Pd(PPh$_3$)$_4$ (0.05 eq.) in 10 mL toluene, a solution of the desired aryl boronic acid (4 eq.) in 1.5 mL EtOH and a solution of K$_2$CO$_3$ (6 eq.) in 1 mL H$_2$O were added. This mixture was refluxed 2 h-4 h. After cooling to r.t. the mixture was partitioned between EtOAc and H$_2$O. The organic layer was washed twice with saturated NaCl solution, dried over MgSO$_4$ and evaporated in vacuo. The crude product was further purified using flash chromatography (silica gel, hexane/EtOAc 20:1→5:1) to yield the desired compound as a colorless solid.

General Procedure 6 (GP6) for the Preparation of Biaryl Catechol Carboxylic Esters via One-Pot Arylboronate—Suzuki Biaryl Synthesis To a solution of methyl 6-bromo-2,2-diphenyl-1,3-benzodioxole-4-carboxylate (1 eq.) in 20 mL dry toluene, Pd(PPh$_3$)$_4$ (0.05 eq.), bis(pinacolato)diboron (1.3 eq.) and KOAc (1.5 eq.) were added and the mixture refluxed for 4 h. After cooling to r.t. the reaction mixture was filtered over Celite, which was washed with an additional 30 mL of toluene. The combined toluene fractions were concentrated in vacuo to ca. 10-15 mL. To this yellowish solution Pd(PPh$_3$)$_4$ (0.05 eq.), 1.2 eq. of the desired arylbromide, e.g. 2-bromo-1,3-benzothiazole and a solution of K$_2$CO$_3$ (5 eq.) in 3 mL H$_2$O were added and the reaction was refluxed for 16 h. After cooling to r.t., the mixture was partitioned between H$_2$O and EtOAc and the organic fraction was washed twice with 20 mL saturated NaCl solution, before being dried over MgSO$_4$ and evaporated under reduced pressure. The crude product was further purified using flash column chromatography (silica gel, hexane/EtOAc 20:1→9: 1) to yield the desired compound as a colorless solid.

General Procedure 7 (GP7) for the Amide Coupling of Catechol Carboxylic Acids and 9-{(3aR,4R,6R,6aR)-6-[(E)-3-aminoprop-1-enyl]-2,2-dimethylperhydrofuro [3,4-d][1,3] di-oxol-4-yl}-9H-purin-6-amine To a solution of the catechol carboxylic acid (1 eq.) in 5 mL CH$_2$Cl$_2$, EDC.HCl (1-(dimethyl-aminopropyl)-3-ethyl-carbodiimide hydrochloride) (1.5 eq.) and N-hydroxy-succinimide (1.3 eq.) were added and the solution was stirred 2 h at r.t. After addition of 9-{(3aR,4R,6R,6aR)-6-[(E)-3-aminoprop-1-enyl]-2,2-dimethylperhydrofuro [1,3]di-oxol-4-yl}-9H-purin-6-amine (0.7 eq.-1 eq.) and Et$_3$N (0.1 mL, 0.68 mmol) stirring was continued another 3 h, then the solution was poured into a separatory funnel containing CH$_2$Cl$_2$ and H$_2$O and the phases were separated. The aqueous phase was extracted with CH$_2$Cl$_2$ (3×15 mL), then the combined organic fractions were washed with saturated aqueous NaCl solution, dried over MgSO$_4$, and evaporated under reduced pressure. The crude product was purified by flash chromatography on silica gel (CH$_2$Cl$_2$→CH$_2$Cl$_2$/ MeOH=20:1) to yield the desired compound as a colorless foam.

General Procedure 8 (GP8) for the Synthesis of Target Molecules by Deprotection of the Acetonide and the Diarylmethylketal Protecting Groups The protected precusor was treated with 3 mL of a mixture of TFA and H$_2$O (1:1) at r.t. for 20-60 min. The reaction mixture was then lyophilized. The crude product was redissolved in 3 mL DMSO and purified using preparative HPLC chromatography. The product fractions were subsequently lyophilized to yield the desired compound as a fluffy solid.

EXAMPLE 1

Preparation of N1-{(E)-3-[(3aR,4R,6R,6aR)-5-(6-amino-9H-purin-9-yl)-3,4-dihydroxytetrahydrofuran-2-yl]prop-2-enyl}-2,3-dihydroxy-benzamide a) 2,2-Diphenyl-benzo[1,3]dioxole-4-carboxylic acid {3-[(3aR,4R,6R,6aR)-6-amino-9H-purin-9-yl)-2,2-dimethyl-tetrahydro-furo[3,4-d][1,3]dioxol-4-yl]-prop-2-enyl}-amide

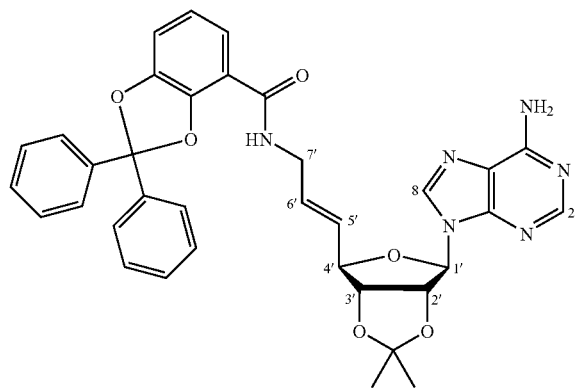

2,2-Diphenyl-1,3-benzodioxole-4-carboxylic acid (150 mg, 0.471 mmol, 1 eq.), EDC.HCl (136 mg, 0.71 mmol, 1.5 eq.), N-hydroxy-succinimide (65 mg, 0.565 mmol, 1.2 eq.), 9-{(3aR,4R,6R,6aR)-6-[(E)-3-aminoprop-1-enyl]-2,2-dimethylperhydrfuro[3,4-d][1,3]di-oxol-4-yl}-9H-purin-6-amine (150 mg, 0.451 mmol, 1 eq.) and Et$_3$N (0.1 mL, 0.68 mmol) were reacted according to GP7.

Yield: 189 mg (67%). Colorless foam. Mp.: 105° C. $[\alpha]_D^{20}$: −14.3 (c=1.0, MeOH). IR (KBr): 3424m; 3175m; 2987w; 1651s; 1532s; 1455s; 1373m; 1246s; 1082s; 867m; 748m. $^1$H-NMR (300 MHz, CDCl$_3$): 1.37 (s, 3 H, CH$_{3\text{-}exo}$); 1.62 (s, 3 H, CH$_{3\text{-}endo}$); 4.05 (m, 2 H, H—C(7'), H—C(7")); 4.69 (m, 1 H, H—C(4')); 4.95 (dd; J=6.5, 3.7, 1 H, H—C(3')); 5.46 (dd, J=6.5, 2.2, 1 H, H—C(2')); 5.61 (bs, 2 H, NH$_2$); 5.86 (m, 2 H, H—C(5'), H—C(6')); 6.08 (d, J=2.2, 1 H, H—C(1')); 6.95 (t, J=8.1, 1 H, H$_{arom, Cat.}$); 7.02 (dd, J=8.1, 1.2, 1 H, H$_{arom, Cat.}$); 7.14 (t, J=5.6, 1 H, NHCO); 7.35-7.39 (m, 6 H, H$_{arom, Ketal}$), 7.48-7.53 (m, 4 H, H$_{arom, Ketal}$); 7.58 (dd, J=8.7, 1.2, H$_{arom, Cat.}$); 7.84 (s, 1 H, H—C(8)); 8.20 (s, 1 H, H—C(2)). $^{13}$C-NMR (75 MHz, CDCl$_3$): 25.5; 27.2; 40.7; 84.0; 84.5; 87.1; 90.2; 111.8; 114.6; 115.5; 118.1; 120.1; 122.0; 122.4; 126.3; 128.2; 128.3; 129.5; 130.6; 138.8; 139.6; 144.5; 147.0; 149.3; 153.0; 155.3; 163.2. HR-MS (MALDI): calcd. for C$_{35}$H$_{33}$N$_6$O$_6$ ([M+H]$^+$): 633.2461, found 633.2442.

b) N1-{(E)-3-[(3aR,4R,6R,6aR)-5-(6-amino-9H-purin-9-yl)-3,4-dihydroxytetrahydro-furan-2-yl]prop-2-enyl}-2,3-dihydroxy-benzamide

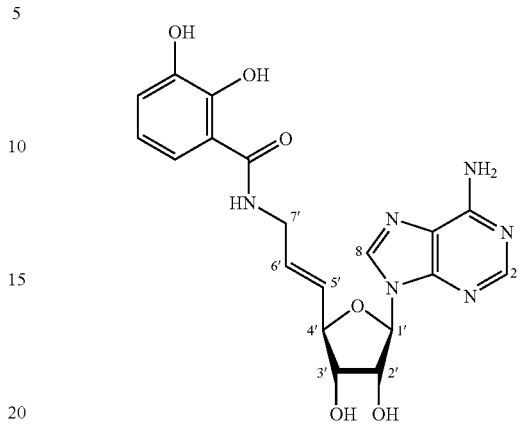

The protected precursor (120 mg, 0.19 mmol) was treated with 3.5 mL of a mixture of TFA and H$_2$O (5:2) at 0° C. for 60 min. The solvents were evaporated under reduced pressure, then the residue was dissolved in 5% NH$_4$OH in H$_2$O and extracted with CHCl$_3$ (3×15 mL). The aqueous phase was then evaporated under reduced pressure and coevaporated with H$_2$O (3×10 mL). The crude product was redissolved in 8 mL DMF and purified using HPLC chromatography to yield the title compound as a colorless solid.

Yield: 60 mg (74%). Mp.: 134° C. (dec.). $t_{R, analyt.}$: 10.9 min. IR (KBr): 3424 br, s; 1641s; 1604s; 1460w; 1420w; 1340w; 1278m; 1129w; 1050w. $^1$H-NMR (500 MHz, (CD$_3$)$_2$SO): 3.95 (m, 2 H, H—C(7'), H—C(7")); 4.11 (t, J=4.8, 1 H, H—C(4')); 4.37 (m; 1 H, H—C(3')); 4.65 (t, J=H, H—C(2')); 5.82-5.93 (m, 2 H, H—C(5'), H—C(6')); 5.93 (d, J=5.1, 1 H, H—C(1')); 6.69 (t, J=7.9, 1 H, H$_{arom, Cat.}$); 6.92 (dd, J=7.9, 1.1, 1 H, H$_{arom, Cat.}$); 7.31 (dd, J=7.9, 1 H, H$_{arom, Cat.}$); 8.23 (s, 1 H, H—C(8)); 8.49 (s, 1 H, H—C(2)); 8.97 (t, J=5.4, 1 H, H—NHCO); 12.64 (bs, 1 H, OH). $^{13}$C-NMR (125 MHz, (CD$_3$)$_2$SO): 40.1; 73.1; 73.9; 84.3; 87.8; 115.0; 117.2; 118.0; 118.9; 119.1; 129.2; 129.6; 141.3; 146.2; 148.9; 149.0; 149.6; 153.2; 169.5. HR-MS (MALDI): calcd. for C$_{19}$H$_{21}$N$_6$O$_6$ ([M+H]$^+$): 429.1522, found 429.1513.

EXAMPLE 2

Preparation of N1-{(E)-3-[(3aR,4R,6R,6aR)-5-(6-amino-9H-purin-9-yl)-3,4-dihydroxytetrahydrofuran-2-yl]prop-2-enyl}-5-bromo-2,3-dihydroxy-benzamide a) Methyl 6-bromo-2,2-diphenyl-1,3-benzodioxole-4-carboxylate

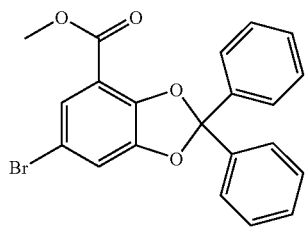

Methyl 5-bromo-2,3-dihydroxybenzoate (3 g, 12.87 mmol, 1 eq.) was reacted with dichlorodiphenylmethane (3.7 mL, 4.58 g, 19.31 mmol, 1.5 eq.) according to GP2, Method A.

Yield: 4 g (76%). Colorless powder. Mp.: 146-148° C. IR (KBr): 3079w; 2950w; 1718s (CO); 1467s; 1355s; 1238s; 1204s; 1043s; 1013s; 944m; 867m; 780s. $^1$H-NMR (300 MHz, CDCl$_3$): 3.94 (s, 3 H, CH$_3$), 7.14 (d, J=1.9, 1 H, H$_{arom, Cat.}$); 7.38-7.41 (m, 6 H, H$_{arom, Ketal}$); 7.55-7.59 (m, 5 H, H$_{arom, Cat.}$, H$_{arom, Ketal}$). $^{13}$C-NMR (75 MHz, CDCl$_3$): 52.4; 112.6; 113.7; 115.6; 119.1; 125.0; 126.2; 128.3; 129.4; 139.0; 147.5; 149.1; 163.7. HR-MS (MALDI): calcd. for C$_{21}$H$_{16}$BrO$_4$ ([M+H]$^+$): 411.0231, found 411.0220.

b)
6-Bromo-2,2-diphenyl-1,3-benzodioxole-4-carboxylic acid

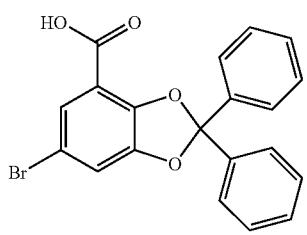

Methyl 6-bromo-2,2-diphenyl-1,3-benzodioxole-4-carboxylate (0.5 g, 1.216 mmol, 1 eq.) and LiOH.H$_2$O (204 mg, 4.86 mmol, 4 eq.) were reacted according to GP3.

Yield: 437 mg (91%). Colorless solid. Mp.: 215° C. IR (KBr): 3063m; 2873 br, m; 2538m; 1695s (CO); 1598w; 1468s; 1406m; 1350m; 1287s; 1234s; 1202s; 1045s; 1023s; 949m; 858m; 784m; 698s. $^1$H-NMR (300 MHz, CDCl$_3$): 7.19 (d, J=2.1, 1 H, H$_{arom, Cat.}$); 7.40-7.42 (m, 6 H, H$_{arom, Ketal}$); 7.58-7.62 (m, 5 H, H$_{arom, Cat.}$, H$_{arom, Ketal}$). $^{13}$C-NMR (75 MHz, CDCl$_3$): 112.7; 112.8; 116.4; 119.5; 125.4; 126.3; 128.4; 129.5; 138.9; 148.3; 149.3; 167.9. HR-MS (MALDI): calcd. for C$_{20}$H$_{14}$BrO$_4$ ([M+H]$^+$): 397.0075, found 397.0078. Anal. calcd. for C$_{20}$H$_{13}$BrO$_4$: C 60.47, H 3.30. found C 60.40; H 3.35.

c) 6-Bromo-2,2-diphenyl-benzo[1,3]dioxole-4-carboxylic acid {3-[(3aR,4R,6R,6aR)-6-(6-amino-9H-purin-9-yl)-2,2-dimethyl-tetrahydro-furo[3,4-d][1,3]dioxol-4-yl]-prop-2-enyl}-amide

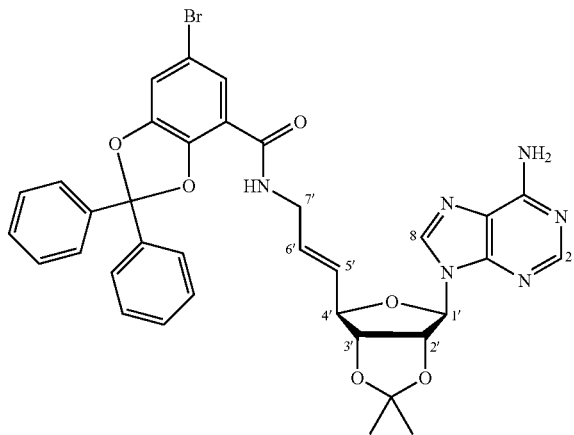

6-Bromo-2,2-diphenyl-1,3-benzodioxole-4-carboxylic acid (200 mg, 0.503 mmol, 1.4 eq.), EDC.HCl (145 mg, 0.755 mmol, 2.1 eq.), N-hydroxy-succinimide (76 mg, 0.654 mmol, 1.8 eq.), 9-{(3aR,4R,6R,6aR)-6-[(E)-3-aminoprop-1-enyl]-2,2-dimethylperhydrofuro[3,4-d][1,3]di-oxol-4-yl}-9H-purin-6-amine (120 mg, 0.361 mmol, 1 eq.) and Et$_3$N (0.1 mL, 0.68 mmol) were reacted according to GP7.

Yield: 166 mg (65%). Colorless foam. Mp.: 116° C. IR (KBr): 3424m; 3170 br, w; 2985w; 1636s; 1594s; 1531m; 1495s; 1423w; 1373w; 1236s; 1207s; 1156w; 1082s; 1016m; 867w; 778w; 698m. $^1$H-NMR (300 MHz, CDCl$_3$): 1.38 (s, 3 H, CH$_{3-exo}$); 1.62 (s, 3 H, CH$_{3-endo}$); 4.04 (m, 2 H, H—C(7'), H—C(7")); 4.69 (m, 1 H, H—C(4')); 4.95 (dd, J=6.3, 3.6, 1 H, H—C(3')); 5.45 (dd, J=6.3, 2.3, 1 H, H—C(2')); 5.84 (m, 2 H, H—C(5'), H—C(6')); 5.96 (bs, 2 H, NH$_2$); 6.09 (d, J=2.3, 1 H, H—C(1')); 7.05 (t, J=5.6, 1 H, NHCO); 7.15 (d, J=2.0, 1 H, H$_{arom, Cat.}$); 7.35-7.40 (m, 6 H, H$_{arom, Ketal}$); 7.44-7.50 (m, 4 H, H—C(6), H$_{arom, Ketal}$); 7.72 (d, J=2.0, 1 H, H$_{arom, Cat.}$); 7.87 (s, 1 H, H—C(8)); 8.20 (s, 1 H, H—C(2)). $^{13}$C-NMR (75 MHz, CDCl$_3$): 25.5; 27.3; 40.9; 84.1; 84.5; 87.1; 90.3; 114.0; 114.7; 115.2; 116.3; 119.5; 120.1; 125.0; 126.3; 128.4; 129.8; 130.5; 138.3; 140.1; 144.1; 148.1; 149.2; 151.7; 154.7; 162.0. HR-MS (MALDI): calcd. for C$_{35}$H$_{32}$BrN$_6$O$_6$ ([M+H]$^+$): 711.1567, found 711.1553. Anal. calcd. for C$_{35}$H$_{31}$BrN$_6$O$_6$: C 59.08, H 4.39, N 11.81. found C 59.06, H 4.54, N 11.62.

d) N1-{(E)-3-[(3aR,4R,6R,6aR)-5-(6-amino-9H-purin-9-yl)-3,4-dihydroxytetrahydrofuran-2-yl]prop-2-enyl}-5-bromo-2,3-dihydroxy-benzamide

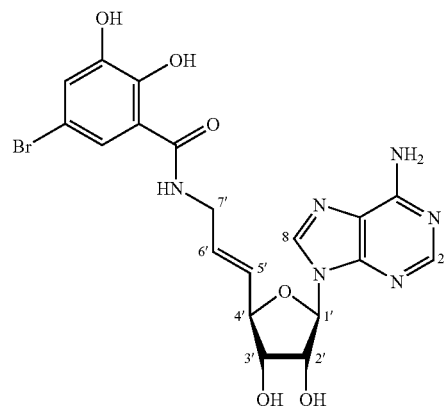

The protected precusor (50 mg, 0.07 mmol) was deprotected according to GP8.

Yield: 18 mg (52%). Colorless solid. $t_{R, analyt.}$: 13.4 min. Mp.: 123° C. (dec.). IR (KBr): 3396 br, m; 1699s; 1637m; 1467w; 1426w; 1325w; 1203s; 1135m; 1050w. $^1$H-NMR (500 MHz, CD$_3$OD): 4.03 (m, 2 H, H—C(7'), H—C(7")); 4.23 (t, J=5.0, 1 H, H—C(4')); 4.52 (m; 1 H, H—C(3')); 4.72 (t, J=4.8, 1 H, H—C(2')); 5.92-5.94 (m, 2 H, H—C(5'); H—C(6')); 6.06 (d, J=4.8, 1 H, H—C(1')); 7.05 (d, J=2.3, 1 H, H$_{arom, Cat.}$); 7.43 (d, J=2.3, 1 H, H—C$_{arom, Cat.}$); 8.27 (s, 1 H, H—C(8)); 8.39 (s, 1 H, H—C(2)). $^{13}$C-NMR (125 MHz, CD$_3$OD): 41.6; 75.2; 75.6; 86.1; 90.6; 111.2; 118.2; 120.7; 121.3; 122.3; 130.3; 130.9; 143.4; 147.8; 148.8; 149.6; 150.2; 153.5; 169.9. HR-MS (MALDI): calcd. for C$_{19}$H$_{20}$BrN$_6$O$_6$ ([M+H]$^+$): 507.0628, found 507.0627.

EXAMPLE 3

Preparation of N1-{(E)-3-[(3aR,4R,6R,6aR)-5-(6-amino-9H-purin-9-yl)-3,4-dihydroxytetrahydrofuran-2-yl]prop-2-enyl}-5-cyano-2,3-dihydroxy-benzamide a) Methyl 6-cyano-2,2-diphenyl-1,3-benzodioxole-4-carboxylate

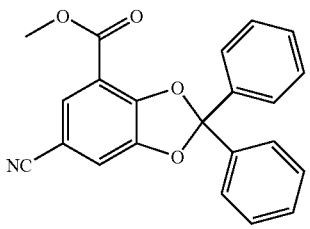

To a solution of methyl 6-bromo-2,2-diphenyl-1,3-benzodioxole-4-carboxylate (800 mg, 1.95 mmol, 1 eq.) in a mixture of 15 mL benzene and 5 mL DMF, Pd(PPh$_3$)$_4$ (225 mg, 0.195 mmol, 0.1 eq.), KCN (127 mg, 1.95 mmol, 1 eq.) and 18-crown-6 (415 mg, 1.56 mmol, 0.8 eq.) was added and the reaction mixture was stirred at 100° C. overnight. Then the reaction mixture was poured into a separatory funnel containing EtOAc and H$_2$O and the aqueous phase was extracted with EtOAc (2×20 mL). The combined organic phases were washed with H$_2$O, then saturated aqueous NaCl solution, dried over MgSO$_4$, and evaporated under reduced pressure. Flash chromatography on silica gel (hexane/EtOAc=20:1→9:1) afforded the desired compound as a colorless solid.

Yield: 530 mg (76%). Mp.: 141° C. IR (KBr): 3051w; 2951w; 2228m (CN); 1713s (CO); 1470s; 1375m; 1264s; 1225s; 1045s; 917m; 786s. $^1$H-NMR (300 MHz, CDCl$_3$): 3.97 (s, 3 H, CH$_3$); 7.20 (d, J=1.9, 1 H, H$_{arom, Cat.}$); 7.39-7.43 (m, 6 H, H$_{arom, Ketal}$); 7.55-7.58 (m, 4 H, H$_{arom, Ketal}$); 7.82 (d, J=1.9, 1 H, H$_{arom, Cat.}$). $^{13}$C-NMR (75 MHz, CDCl$_3$): 52.67; 104.8; 113.4; 113.9; 118.0; 120.4; 126.2; 128.4; 129.2; 129.7; 138.4; 148.9; 151.5; 163.1. HR-MS (MALDI): calcd. for C$_{22}$H$_{16}$NO$_4$ ([M+H]$^+$): 358.1079, found 358.1071.

b) 6-Cyano-2,2-diphenyl-1,3-benzodioxole-4-carboxylic acid

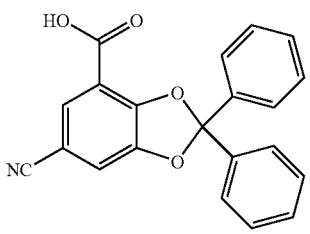

To a solution of methyl 6-cyano-2,2-diphenyl-1,3-benzodioxole-4-carboxylate (60 mg, 0.168 mmol, 1 eq.) in a mixture of 3 mL MeOH and 0.5 mL CH$_2$Cl$_2$, a solution of LiOH.H$_2$O (21 mg, 0.5 mmol, 3 eq.) in 3 mL H$_2$O was added. The reaction mixture was vigorously stirred 16 h at r.t., then acidified with 10% AcOH in H$_2$O and extracted with EtOAc (3×20 mL). The combined organic phases were washed with saturated aqueous NaCl solution, dried over MgSO$_4$, and the solvents evaporated under reduced pressure to yield the desired compound as a colorless solid.

Yield: 53 mg (92%). Mp.: 221° C. IR (KBr): 2925m; 2229m; 1696s; 1449s; 1267s; 1213s; 1048s; 949m; 922m; 756m; 694s; 641m; 617w. $^1$H-NMR (300 MHz, CDCl$_3$): 7.25 (d, J=1.7, 1 H, H$_{arom, Cat.}$); 7.41 (m, 6 H, H$_{arom, Ketal}$); 7.58 (m, 4 H, H$_{arom, Ketal}$); 7.87 (d, J=1.7, 1 H, H$_{arom, Cat.}$). $^{13}$C-NMR (75MHz, CDCl$_3$): 105.0; 112.6; 114.4; 117.8; 120.7; 126.1; 128.5; 129.6; 129.8; 138.2; 149.0; 152.1; 167.1. HR-MS (MALDI): calcd. for C$_{21}$H$_{14}$NO$_4$ ([M+H]$^+$): 344.0923, found 344.0910.

c) 6-Cyano-2,2-diphenyl-benzo[1,3]dioxole-4-carboxylic acid {3-[(3aR,4R,6R,6aR)-6-(6-amino-9H-purin-9-yl)-2,2-dimethyl-tetrahydro-furo[3,4-d][1,3]dioxol-4-yl]-prop-2-enyl}-amide

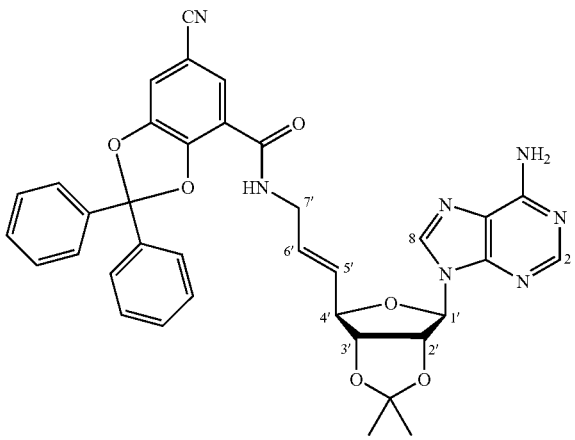

6-Cyano-2,2-diphenyl-1,3-benzodioxole-4-carboxylic acid (80 mg, 0.23 mmol, 1.5 eq.), EDC.HCl (73 mg, 0.38 mmol, 2.5 eq.), 9-{(3aR,4R,6R,6aR)-6-[(E)-3-aminoprop-1-anyl]-2,2-dimethylperhydrofuro[3,4-d][1,3]di-oxol-4-yl}-9H-purin-6-amine (50 mg, 0.15 mmol, 1 eq.) and Et$_3$N (0.05 mL, 0.34 mmol) were reacted according to GP7.

Yield: 67 mg (68%). Colorless foam. Mp.: 125° C. IR (KBr): 3428s; 3171w; 2986w; 2227w; 1635s; 1597m; 1528m; 1466s; 1374m; 1262s; 1209s; 1082m; 1017m; 867w; 762w; 699m; 641w. $^1$H-NMR (300 MHz, CDCl$_3$): 1.38 (s, 3 H, CH$_{3\text{-}exo}$); 1.62 (s, 3 H, CH$_{3\text{-}endo}$); 4.05 (m, 2 H, H—C(7'), H—C(7")); 4.70 (m, 1 H, H—C(4')); 4.96 (dd; J=6.3, 3.9, 1 H, H—C(3')); 5.46 (dd, J=6.3, 2.0, 1 H, H—C(2')); 5.79 (bs, 2 H, NH$_2$); 5.83 (m, 2 H, H—C(5'), H—C(6')); 6.08 (d, J=2.0, 1 H, H—C(1')); 7.00 (t, J=5.7, 1 H, NHCO); 7.22 (d, J=1.7, 1 H, H$_{arom, Cat.}$); 7.38-7.49 (m, 10 H, H$_{arom, Ketal}$); 7.86 (s, 1 H, H—C(8)); 7.99 (d, J=1.7, H$_{arom, Cat.}$); 8.19 (s, 1 H, H—C(2)). $^{13}$C-NMR (75 MHz, CDCl$_3$): 25.5; 27.3; 41.0; 84.1; 84.5; 87.2; 90.3; 105.9; 113.7; 114.7; 116.1; 118.0; 120.2; 120.7; 126.3; 128.6; 128.8; 129.1; 130.1; 130.2; 137.6; 140.0; 147.8; 148.0; 149.2; 152.3; 155.0; 161.2. HR-MS (MALDI): calcd. for C$_{36}$H$_{32}$N$_7$O$_6$ ([M+H]$^+$): 658.2414, found 658.2403.

d) N1-{(E)-3-[(3aR,4R,6R,6aR)-5-(6-amino-9H-purin-9-yl)-3,4-dihydroxytetrahydro-furan-2-yl]prop-2-enyl}-5-cyano-2,3-dihydroxy-benzamide

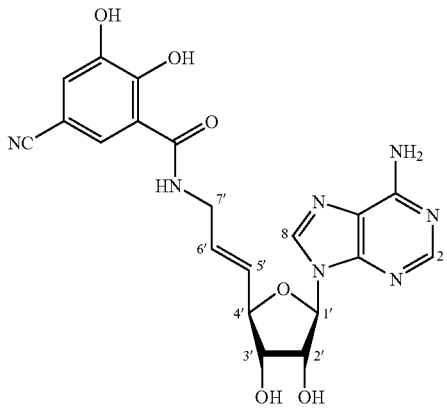

The protected precursor (70 mg, 0.11 mmol) was deprotected according to GP8.

Yield: 20 mg (42%). $t_{R, analyt.}$: 9.0 min. IR (KBr): 3396 br, s; 2233w; 1703s; 1639s; 1477w; 1441w; 1303m; 1195s; 1137m; 1050w. $^1$H-NMR (500 MHz, CD$_3$OD): 4.06 (d, J=3.7, 2 H, H—C(7'), H—C(7")); 4.24 (t, J=4.9, 1 H, H—C(4')); 4.51 (t, J=4.9, 1 H, H—C(3')); 4.73 (t, J=4.6, 1 H, H—C(2')); 5.94 (m, 2 H, H—C(5'), H—C(6')); 6.04 (d, J=4.6, 1 H, H—C(1')); 7.17 (d, J=1.8, 1 H, $H_{arom, Cat.}$); 7.70 (d, J=1.8, 1 H, $H_{arom, Cat.}$); 8.23 (s, 1 H, H—C(8)); 8.33 (s, 1 H, H—C(2)). $^{13}$C-NMR (75 MHz, (CD$_3$OD+2 drops of DMSO-d$_6$): 41.7; 75.2; 75.4; 85.9; 90.2; 102.6; 117.3; 119.8; 120.5; 121.1; 124.2; 130.5; 130.6; 143.6; 146.3; 148.4; 149.9; 154.6; 169.3 (1 peak missing). HR-MS (MALDI): calcd. for $C_{20}H_{20}N_7O_6$ ([M+H]$^+$): 454.1475, found 454.1466.

EXAMPLE 4

Preparation of N1-{(E)-3-[(3aR,4R,6R,6aR)-5-(6-amino-9H-purin-9-yl)-3,4-dihydroxytetrahydrofuran-2-yl]prop-2-enyl}-5-(2,2,2-trifluoro-acetyl)-2,3-dihydroxy-benzamide a) 2,2-Diphenyl-6-(trifluoroacetyl)-1,3-benzodioxole-4-carboxylic acid

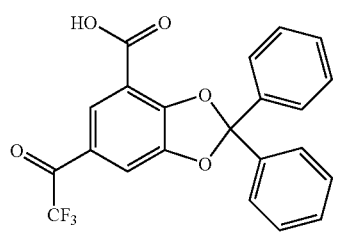

6-Bromo-2,2-diphenyl-1,3-benzodioxole-4-carboxylic acid (200 mg, 0.503 mmol, 1 eq.), LiOMe (40 mg, 1 mmol, 2 eq.) and ethyl trifluoroacetate (0.6 mL, 5.03 mmol, 10 eq.) as the electrophile were reacted according to GP4, Method A. The crude product was purified using flash chromatography (silica gel, hexane/EtOAc/AcOH 77:20:3) to give the title compound as a yellowish solid.

Yield: 79 mg (38%). Mp.: 187° C. IR (KBr): 2925m; 2555m; 1692s; 1635m; 1482s; 1254s; 1213s; 1131s; 1048m; 1013m; 987m; 945m; 802m; 760s; 699s. $^1$H-NMR (300 MHz, CDCl$_3$): 7.40-7.44 (m, 6 H, $H_{arom, Ketal}$); 7.59-7.62 (m, 4 H, $H_{arom, Ketal}$); 7.74 (d, J=1.2, 1 H, $H_{arom, Cat.}$); 8.35 (m, 1 H, $H_{arom, Cat.}$). 13C-NMR (75 MHz, CDCl$_3$): 111.7; 112.4; 116.5 (q, J=289); 121.0; 124.0; 126.2; 128.5; 128.9; 129.8; 138.3; 149.6; 154.3; 167.7; 178.1 (q, J=35.2). $^{19}$F-NMR (282 MHz, CDCl$_3$): −70.72 (s). HR-MS (MALDI): calcd. for $C_{22}H_{14}F_3O_5$ ([M+H]$^+$): 415.0793, found 415.0784. Anal. calcd. for $C_{22}H_{13}F_3O_5$: C 63.77, H 3.16; found C 63.81, H 3.29.

b) 2,2-Diphenyl-6-(2,2,2-trofluoro-acetyl)-benzo[1,3]dioxole-4-carboxylic acid {3-[(3aR,4R,6R,6aR)-6-(6-amino-9H-purin-9-yl)-2,2-dimethyl-tetrahydro-furo[3,4-d][1,3]dioxol-4-yl]-prop-2-enyl}-amide

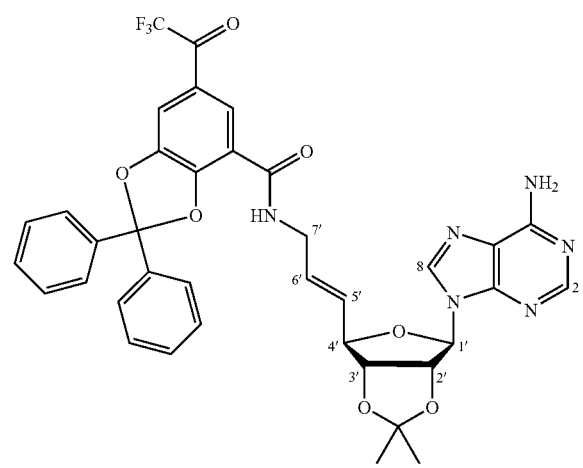

GP7, starting from 2,2-diphenyl-6-(trifluoroacetyl)-1,3-benzodioxole-4-carboxylic acid (250 mg, 0.603 mmol, 1 eq.), EDC.HCl (175 mg, 0.91 mmol, 1.5 eq.), N-hydroxysuccinimide (90 mg, 0.784 mmol, 1.3 eq.) and 9-{(3aR,4R,6R,6aR)-6-[(E)-3-aminoprop-1-enyl]-2,2-dimethyl-perhydrofuro [3,4-d][1,3]di-oxol-4-yl}-9H-purin-6-amine (120 mg, 0.361 mmol, 0.6 eq.) provided the title compound as a colorless foam.

Yield: 174 mg (66%). Mp.: 108-110° C. IR (KBr): 3426m; 3199m; 2986m; 2227w; 1644s; 1599m; 1534m; 1476m; 1442m; 1378w; 1253s; 1207s; 1151m; 1082m; 1017w; 866w; 761w; 699m; 642w. $^1$H-NMR (300 MHz, CDCl$_3$): 1.38 (s, 3 H, CH$_{3-exo}$); 1.62 (s, 3 H, CH$_{3-endo}$); 4.07 (m, 2 H, H—C(7'), H—C(7")); 4.68 (m, 1 H, H—C(4')); 4.97 (dd; J=6.3, 3.6, 1 H, H—C(3')); 5.47 (dd, J=6.3, 2.1, 1 H, H—C(2')); 5.85 (m, 4 H, H—C(5'), H—C(6'), NH$_2$); 6.08 (d, J=2.1, 1 H, H—C(1')); 7.03 (t, J=5.7, 1 H, NHCO); 7.38-7.45 (m, 6 H, $H_{arom, Ketal}$); 7.47-7.52 (m, 4 H, $H_{arom, Ketal}$); 7.69 (d, J=1.7, 1 H, $H_{arom, Cat.}$); 7.86 (s, 1 H, H—C(8)); 8.21 (s, 1 H, H—C(2)); 8.43 (d, J=1.7, $H_{arom, Cat.}$). $^{13}$C-NMR (75 MHz, CDCl$_3$): 25.5; 27.3; 41.1; 84.1; 84.5; 87.1; 90.2; 111.5; 114.7; 115.5; 116.6 (q, J=281); 120.1; 120.9; 124.8; 126.3; 128.2; 128.6; 128.8; 130.2; 137.6; 137.7; 139.9; 148.4; 149.2; 150.2; 152.3; 155.0; 161.6; 178.5 (q, J=35.5). $^{19}$F-NMR (282 MHz, CDCl$_3$): −71.24 (s). HR-MS (MALDI): calcd. for $C_{37}H_{32}F_3N_6O_7$ ([M+H]$^+$): 729.2285, found 729.2291.

c) N1-{(E)-3-[(3aR,4R,6R,6aR)-5-(6-amino-9H-purin-9-yl)-3,4-dihydroxytetrahydro-furan-2-yl]prop-2-enyl}-5-(2,2,2-trifluoro-acetyl)-2,3-dihydroxy-benzamide

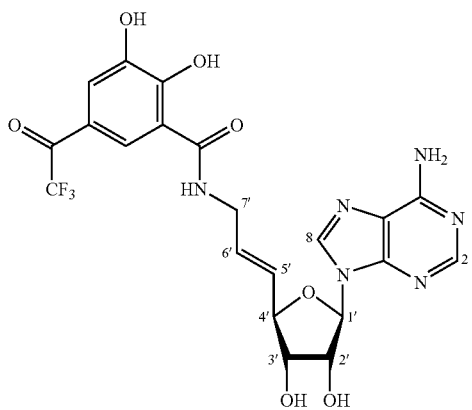

GP8, starting from the protected precursor (100 mg, 0.137 mmol) gave the desired product as a colorless solid.

Yield: 40 mg (56%). $t_{R, \, analyt.}$: 11.1 min. IR (KBr): 3370 br, s; 1699s; 1640s; 1545w; 1439w; 1326m; 1283m; 1202s; 1142s; 1052w; 724w. $^1$H-NMR (500 MHz, CD$_3$OD): 4.05 (d, J=2.2, 2 H, H—C(7'), H—C(7")); 4.23 (t, J=5.0, 1 H, H—C(4')); 4.52 (m, 1 H, H—C(3')); 4.72 (t, J=4.9, 1 H, H—C(2')); 5.94 (m, 2 H, H—C(5'), H—C(6')); 6.05 (d, J=4.9, 1 H, H—C(1')); 7.18 (s, 1 H, H—C(8)); 7.57 (m, 1 H, H$_{arom, \, Cat.}$); 8.26 (d, J=4.2, 1 H, H$_{arom, \, Cat.}$); 8.38 (s, 1 H, H—C(2)). $^{13}$C-NMR (125 MHz, (CD$_3$OD): 41.6; 75.2; 75.6; 86.1; 90.5; 116.4; 119.2; 119.3; 120.7; 124.4 (q, J=286); 126.4; 130.2; 131.1; 143.1; 147.2; 148.6; 150.3; 151.0; 154.0; 170.9 (1 peak missing). HR-MS (MALDI): calcd. for C$_{21}$H$_{20}$F$_3$N$_6$O$_7$ ([M+H]$^+$): 525.1346, found 525.1345.

EXAMPLE 5

Preparation of N1-{(E)-3-[(3aR,4R,6R,6aR)-5-(6-amino-9H-purin-9-yl)-3,4-dihydroxytetrahydrofuran-2-yl]prop-2-enyl}-5-(pyridine-4-carbonyl)-2,3-dihydroxy-benzamide a) 6-(Hydroxy-pyridin-4-yl-methyl)-2,2-diphenyl-1,3-benzodioxole-4-carboxylic acid

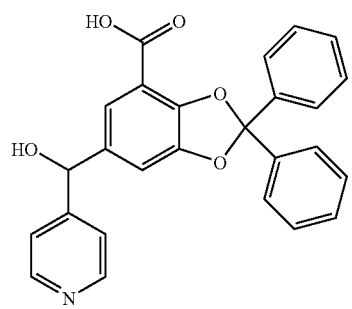

6-Bromo-2,2-diphenyl-1,3-benzodioxole-4-carboxylic acid (1 g, 2.52 mmol, 1 eq.), LiOMe (192 mg, 5.04 mmol, 2 eq.) and pyridine-4-carbaldehyde (0.48 mL, 5.03 mmol, 2 eq.) as the electrophile were reacted according to GP4, Method A. The crude product was purified using flash chromatography (silica gel, CH$_2$Cl$_2$/MeOH 92:8→80:20) to give the title compound as a yellow solid.

Yield 350 mg (33%). Mp.: 213-217° C. (dec.). IR (KBr): 3381 br, s; 1565s; 1473m; 1410s; 1257s; 1205s; 1047s; 1026m; 948w; 806w; 777m; 698m; 642m. $^1$H-NMR (300 MHz, (CD$_3$)$_2$SO): 5.63 (s, 1 H, H$_{benz.}$); 6.11 (bs, 1 H, OH); 7.04 (s, 1 H, H$_{arom, \, Cat.}$); 7.36 (d, J=5.7, 2 H, H$_{arom, \, Pyr.}$); 7.40-7.42 (m, 7 H, H$_{arom, \, Cat}$, H$_{arom, \, Ketal}$); 7.50-7.54 (m, 4 H, H$_{arom, \, Ketal}$); 8.46 (d, J=5.7, 1 H, H$_{arom, \, Pry.}$). $^{13}$C-NMR (75 MHz, (CD$_3$)$_2$SO): 62.6; 108.2; 116.1; 120.9; 121.4; 125.7; 128.2; 129.1; 137.3; 139.5; 139.6; 145.3; 147.0; 149.2; 153.6; 189.8. HR-MS (MALDI): calcd. for C$_{26}$H$_{20}$NO$_5$ ([M+H]$^+$): 426.1341, found 426.1332.

b) 2,2-Diphenyl-6-(pyridine-4-carbonyl)-1,3-benzodioxole-4-carboxylic acid

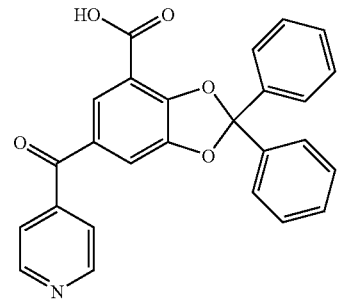

To a solution of 6-(hydroxy-pyridin-4-yl-methyl)-2,2-diphenyl-1,3-benzodioxole-4-carboxylic acid (128 mg, 0.324 mmol, 1 eq.) in a mixture of 10 mL acetone and 3 mL DMSO, IBX (273 mg, 0.973 mmol, 3 eq.) was added and the reaction mixture was stirred 3 h at 50° C. The mixture was partitioned between H$_2$O and EtOAc, and the organic layer was washed with saturated NaCl solution before being dried over MgSO$_4$ and evaporated under reduced pressure to yield the title compound as a yellowish solid.

Yield: 130 mg (95%). Mp.: 256-257° C. IR (KBr): 3447 br, w; 3062w; 2426w; 1709m; 1669m; 1624m; 1475m; 1440s; 1408w; 1323w; 1270s; 1211s; 1048s; 1017m; 910w; 801w; 759m; 698m; 642m. $^1$H-NMR (300 MHz, (CD$_3$)$_2$SO): 7.45-7.48 (m, 7 H, H$_{arom, \, Cat.}$, H$_{arom, \, Ketal}$); 7.54-7.58 (m, 6 H, H$_{arom, \, Ketal}$, H$_{arom, \, Pyr.}$); 7.73 (s, 1 H, H$_{arom, \, Cat.}$); 8.77 (d, J=4.5, 2 H, H$_{arom, \, Pyr.}$). $^{13}$C-NMR (75 MHz, (CD$_3$)$_2$SO): 111.8; 112.9; 118.9; 122.4; 125.8; 127.9; 128.6; 129.5; 129.8; 138.2; 144.2; 148.4; 149.8; 151.1; 163.9; 192.1. HR-MS (MALDI): calcd. for C$_{26}$H$_{19}$NO$_5$ ([M+2H]$^+$): 425.1263, found 425.1254.

c) 2,2-Diphenyl-6-(pyridine-4-carbonyl)-benzo[1,3]dioxole-4-carboxylic acid {3-[(3aR,4R,6R,6aR)-6-(6-amino-9H-purin-9-yl)-2,2-dimethyl-tetrahydrofuro [3,4-d][1,3]dioxol-4-yl]-prop-2-enyl}-amide

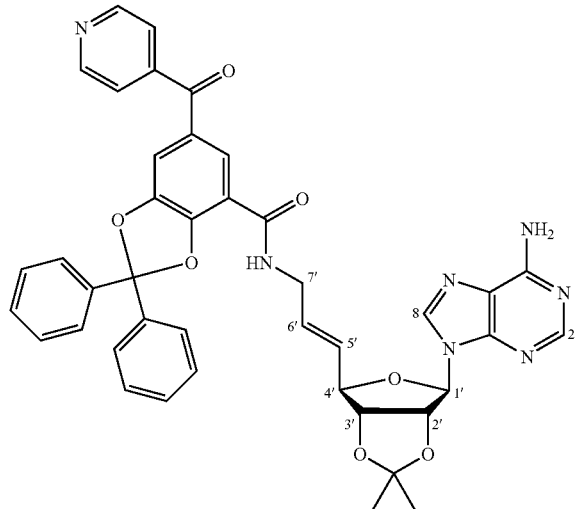

2,2-Diphenyl-6-(pyridine-4-carbonyl)-1,3-benzodioxole-4-carboxylic acid (100 mg, 0.236 mmol, 1 eq.), EDC.HCl (68 mg, 0.354 mmol, 1.5 eq.), N-hydroxy-succinimid (36 mg, 0.307 mmol, 1.3 eq.), 9-{(3aR,4R,6R,6aR)-6-[(E)-3-aminoprop-1-enyl]-2,2-dimethylperhydrofuro[3,4-d][1,3]di-oxol-4-yl}-9H-purin-6-amine (72 mg, 0.215 mmol 0.9 eq.) and Et$_3$N (0.1 mL, 0.68 mmol) were reacted according to GP7.

Yield: 98 mg (62%). Colorless foam. Mp.: 122-126° C. IR (KBr): 3427m; 1661s; 1596m; 1528m; 1472m; 1435m; 1374w; 1266s; 1208s; 1019w; 867w; 780w; 759w; 700w; 647w. $^1$H-NMR (300 MHz, CDCl$_3$): 1.38 (s, 3 H, CH$_{3\text{-}exo}$); 1.62 (s, 3 H, CH$_{3\text{-}endo}$); 4.07 (m, 2 H, H—C(7'), H—C(7")); 4.72 (m, 1 H, H—C(4')); 4.93 (dd; J=6.3, 3.6, 1 H, H—C(3')); 5.40 (dd, J=6.3, 2.0, 1 H, H—C(2')); 5.83 (m, 2 H, H—C(5'), H—C(6')); 6.10 (d, J=2.0, 1 H, H—C(1')); 6.55 (bs, 2 H, NH$_2$); 7.10 (t, J=5.4, 1 H, NHCO); 7.39-7.45 (m, 6 H, H$_{arom, Ketal}$); 7.51-7.55 (m, 6 H, H—C$_{arom, Ketal}$, H$_{arom, pyridyl}$); 7.65 (d, J=1.8, 1 H, H$_{arom, Cat.}$); 7.92 (s, 1 H, H—C(8)); 8.03 (d, J=1.8, H$_{arom, Cat.}$); 8.29 (s, 1 H, H—C(2)); 8.79 (dd, J=4.5, 1.8, 2 H, H$_{arom, pyridyl}$). $^{13}$C-NMR (75 MHz, CDCl$_3$): 25.5; 27.2; 41.0; 84.2; 84.4; 87.2; 90.4; 111.8; 114.6; 114.7; 120.0; 120.4; 122.6; 126.3; 128.0; 128.6; 130.1; 130.3; 130.8; 137.9; 138.0; 140.2; 144.3; 148.4; 148.9; 149.1; 150.3; 151.0; 154.4; 162.1; 193.0. HR-MS (MALDI): calcd. for C$_{41}$H$_{36}$N$_7$O$_7$ ([M+H]$^+$): 738.2676, found 738.2677.

d) N1-{(E)-3-[(3aR,4R,6R,6aR)-5-(6-amino-9H-purin-9-yl)-3,4-dihydroxytetrahydrofuran-2-yl]prop-2-enyl}-5-(pyridine-4-carbonyl)-2,3-dihydroxy-benzamide

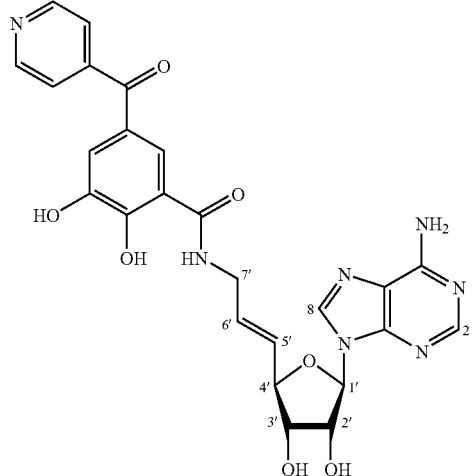

GP8, starting from the protected precursor (50 mg, 0.068 mmol) afforded the desired product as a yellowish solid.

Yield: 18 mg (50%). t$_{R, analyt.}$: 10.9 min. IR (KBr): 3385 br, s; 1678s; 1637s; 1432w; 1307m; 1201s; 1132m; 1051w; 835w; 723w. $^1$H-NMR (500 MHz, CD$_3$OD): 3.94 (d, J=3.7, 2 H, H—C(7'), H—C(7")); 4.13 (t, J=5.3, 1 H, H—C(4')); 4.39 (t, J=5.3, 1 H, H—C(3')); 4.64 (t, J=4.8, 1 H, H—C(2')); 5.82 (m, 2 H, H—C(5'), H—C(6')); 5.93 (d, J=4.8, 1 H, H—C(1')); 7.37 (d, J=2.1, 1 H, H$_{arom, Cat.}$); 7.57 (dd, J=4.6, 1.6, 2 H, H$_{arom, Pyr.}$); 7.71 (d, J=2.1, 1 H, H$_{arom, Cat.}$); 8.12 (s, 1 H, H—C(8)); 8.22 (s, 1 H, H—C(2)); 8.65 (dd, J=4.6, 1.6, 2 H, H$_{arom, Pyr.}$). $^{13}$C-NMR (125 MHz, CD$_3$OD): 41.7; 75.1; 75.6; 85.9; 90.5; 116.7; 119.6; 120.7; 123.5; 124.5; 127.9; 130.5; 130.7; 142.5; 147.7; 148.1; 150.3; 150.4; 150.5; 155.1; 155.7; 170.2; 194.7. HR-MS (MALDI): calcd. for C$_{25}$H$_{24}$N$_7$O$_7$ ([M+H]$^+$): 534.1737, found 534.1729.

EXAMPLE 6

Preparation of N1-{(E)-3-[(3aR,4R,6R,6aR)-5-(6-amino-9H-purin-9-yl)-3,4-dihydroxytetrahydrofuran-2-yl]prop-2-enyl}-5-cyclohexanecarbonyl-2,3-dihydroxy-benzamide a) 6-Cyclohexanecarbonyl-2,2-diphenyl-1,3-benzodioxole-4-carboxylic acid

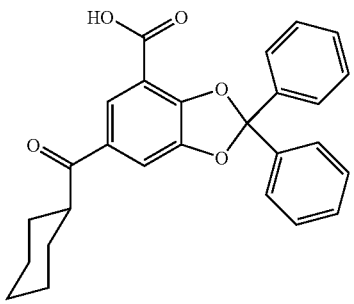

6-Bromo-2,2-diphenyl-1,3-benzodioxole-4-carboxylic acid (1.26 g, 3.16 mmol, 1 eq.), LiOMe (240 mg, 6.32 mmol, 2 eq.) and cyclohexanecarboxylic acid methoxy-methyl-amide (650 mg, 3.8 mmol, 1.2 eq.) as the electrophile were reacted according to GP4, Method A. The crude product was purified using flash chromatography (silica gel, hexane/ Et2O/AcOH 5:1:0.1) and subsequent recrystallization from $CH_2Cl_2$/hexane to give the title compound as a yellowish solid.

Yield: 338 mg (25%). Mp.: 212–214° C. IR (KBr): 3062w; 2932m; 2854w; 1693s; 1628w; 1448s; 1250s; 1205s; 1155m; 1042m; 1020m; 988m; 948m; 875w; 752m; 695s. $^1$H-NMR (300 MHz, $CDCl_3$): 1.26–1.52 (m, 6 H, $CH_{2,cyclohexl}$); 1.72–1.86 (m, 4H, $CH_{2,cyclohexyl}$); 3.24 (m, 1 H, CHCO); 7.38–7.45 (m, 6 H, $H_{arom, Ketal}$); 7.59–7.65 (m, 4 H, $H_{arom, Ketal}$); 7.70 (d, J=1.7, 1 H, $H_{arom, Cat.}$); 8.16 (d, J=1.7, 1 H, $H_{arom, Cat.}$) $^{13}$C-NMR (75 MHz, $CDCl_3$): 25.9; 26.0; 29.7; 45.4; 110.9; 112.1; 119.8; 125.4; 126.3; 128.4; 129.6; 130.7; 138.8; 149.3; 152.4; 168.8; 201.2. HR-MS (MALDI): calcd. for $C_{27}H_{25}O_5$ ([M+H]$^+$): 429.1702, found 429.1693.

b) 6-Cyclohexanecarbonyl-2,2-diphenyl-benzo[1,3]dioxole-4-carboxylic acid {3-[(3aR,4R,6R,6aR)-6-(6-amino-9H-purin-9-yl)-2,2-dimethyl-tetrahydro-furo[3,4-d][1,3]dioxol-4-yl]-prop-2-enyl}-amide

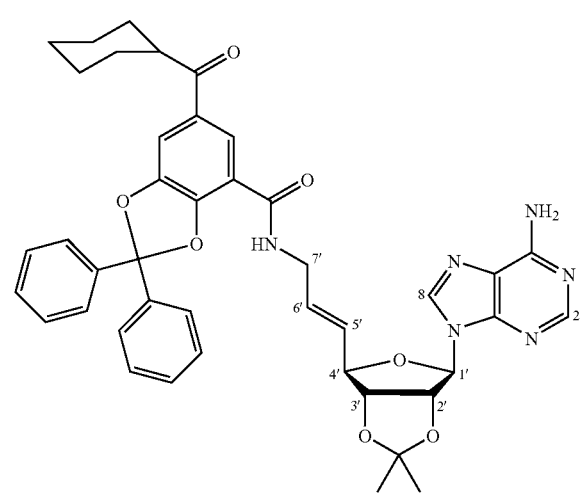

2,2-Diphenyl-6-cyclohexanecarbonyl-1,3-benzodioxole-4-carboxylic acid (197 mg, 0.46 mmol, 1 eq.), EDC.HCl (133 mg, 0.69 mmol, 1.5 eq.), N-hydroxy-succinimide (70 mg, 0.6 mmol, 1.3 eq.), 9-{(3aR,4R,6R,6aR)-6-[(E)-3-aminoprop-1-enyl]-2,2-dimethylperhydrofuro[3,4-d][1,3]dioxol-4-yl}-9H-purin-6-amine (130 mg, 0.391 mmol, 0.85 eq.) and Et$_3$N (0.1 mL, 0.68 mmol) were reacted according to GP7.

Yield: 145 mg (50%). Colorless foam. Mp.: 120–122° C. IR (KBr): 3428 br, m; 2931m; 2853w; 1667s; 1636s; 1596m; 1529m; 1473m; 1433m; 1376m; 1252s; 1209s; 1154w; 1082m; 1049m; 1018w; 867w; 777w; 699w. $^1$H-NMR (300 MHz, $CDCl_3$): 1.24–1.52 (m, 9 H, $CH_{3-exo}$, $CH_{2,cyclohexyl}$); 1.62 (s, 3 H, $CH_{3-endo}$); 1.70–1.86 (m, 4 H, $CH_{2,cyclohexyl}$); 3.70 (m, 1 H, CHCO); 4.07 (m, 2 H, H—C(7'), H—C(7'')); 4.70 (m, 1 H, H—C(4')); 4.96 (dd; J=6.5, 3.9, 1 H, H—C(3')); 5.45 (dd, J=6.5, 2.1, 1 H, H—C(2')); 5.86 (m, 2 H, H—C(5'), H—C(6')); 5.92 (bs, 2 H, NH$_2$); 6.09 (d, J=2.1, 1 H, H—C(1')); 7.11 (t, J=5.4, 1 H, NHCO); 7.36–7.41 (m, 6 H, $H_{arom, Ketal}$); 7.48–7.52 (m, 4 H, H—$C_{arom, Ketal}$); 7.65 (d, J=1.5, 1 H, H—$C_{arom, Cat.}$); 7.87 (s, 1 H, H—C(8)); 8.22 (s, 1 H, H—C(2)); 8.24 (d, J=1.5, H—$C_{arom, Cat.}$). $^{13}$C-NMR (75 MHz, $CDCl_3$): 25.4; 25.8; 26.0; 27.2; 29.6; 40.9; 45.3; 84.1; 84.4; 87.1; 90.2; 110.9; 114.4; 114.7; 119.7; 120.1; 124.6; 126.3; 128.4; 129.8; 130.4; 131.5; 138.1; 138.2; 139.9; 148.0; 148.1; 149.2; 152.0; 154.8; 162.5; 201.8. HR-MS (MALDI): calcd. for $C_{42}H_{43}N_6O_7$ ([M+H]$^+$): 743.3193, found 743.3195. Anal. calcd. for $C_{42}H_{42}N_6O_5$: C 67.91, H 5.70, N 11.31. found C 67.77, H 5.85, N 11.05.

c) N1-{(E)-3-[(3aR,4R,6R,6aR)-5-(6-amino-9H-purin-9-yl)-3,4-dihydroxytetrahydro-furan-2-yl]prop-2-enyl}-5-cyclohexanecarbonyl-2,3-dihydroxy-benzamide

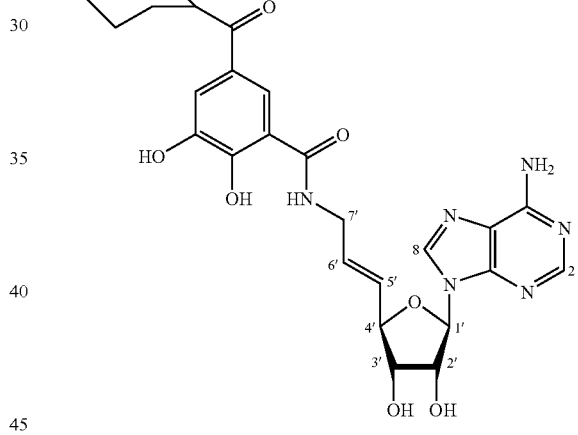

GP8, starting from the protected precursor (60 mg, 0.081 mmol) afforded the desired product as a colorless solid.

Yield: 25 mg (59%). $t_{R, analyt.}$: 14.5 min (linear gradient of $CH_3CN$ in $H_2O$ with 0.1% TFA 15→55% in 20 min.) IR (KBr): 3388 br, s; 2933m; 1700s; 1638s; 1543w; 1430w; 1326m; 1295m; 1202s; 1130m; 1048w; 837w; 801w; 724w. $^1$H-NMR (500 MHz, $CD_3OD$): 1.23–1.29 (m, 1 H, 3.94 $CH_{2,cyclohexyl}$); 1.38–1.50 (m, 4 H, $CH_{2,cyclohexyl}$); 1.72–1.83 (m, 5 H, $CH_{2,cyclohexyl}$); 3.35 (t, J=1.6, 1 H, CHCO); 4.08 (d, J=3.3, 2 H, H—C(7'), H—C(7'')); 4.25 (t, J=5.0, 1 H, H—C(4')); 4.52 (t, J=5.0, 1 H, H—C(3')); 4.74 (t, J=4.7, 1 H, H—C(2')); 5.96 (m, 2 H, H—C(5'), H—C(6')); 6.04 (d, J=4.7, 1 H, H—C(1')); 7.53 (d, J=2.0, 1 H, H—$C_{arom, Cat.}$); 8.02 (d, J=2.0, 1 H, $H_{arom, Cat.}$); 8.23 (s, 1 H, H—C(8)); 8.34 (s, 1 H, H—C(2)). $^{13}$C-NMR (125 MHz, $CD_3OD$): 26.8; 27.1; 30.8; 41.7; 46.0; 75.1; 75.6; 86.0; 90.5; 116.4; 118.5; 120.7; 128.6; 130.5; 130.9; 142.8; 147.8; 149.7; 150.3; 154.7; 154.9; 170.7; 204.6. HR-MS (MALDI): calcd. for $C_{26}H_{31}N_6O_7$ ([M+H]$^+$): 539.2254, found 539.2244.

EXAMPLE 7

Preparation of N1-{(E)-3-[(3aR,4R,6R,6aR)-5-(6-amino-9H-purin-9-yl)-3,4-dihydroxytetrahydrofuran-2-yl]prop-2-enyl}-5-chloro-2,3-dihydroxy-benzamide a) Methyl 5-chloro-2,3-dihydroxy-benzoate

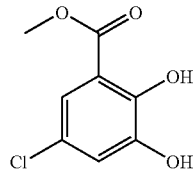

5-Chloro-2,3-dihydroxybenzoic acid (290 mg, 1.54 mmol, 1 eq.) and $SOCl_2$ (550 mg, 4.61 mmol, 3 eq.) were reacted according to GP1.

Yield: 250 mg (80%). Gray powder. IR (KBr): 3453s; 3096m; 2960m; 1700s; 1673s; 1471s; 1437s; 1316s; 1233s; 1202s; 1152s; 1013m; 932m; 863m; 788m; 723m. $^1$H-NMR (300 MHz, $CDCl_3$): 3.96 (s, 3 H, $OCH_3$); 5.73 (bs, 1 H, OH); 7.10 (d, J=2.1, 1 H, $H_{arom, Cat.}$); 7.35 (d, J=2.1, 1 H, $H_{arom, Cat.}$); 10.84 (s, 1 H, OH). $^{13}$C-NMR (75 MHz, $CDCl_3$): 52.8; 112.7; 119.7; 120.0; 124.1; 145.7; 147.6; 169.7. HR-MS (EI): calcd. for $C_8H_7ClO_4$ ([M+H]$^+$): 202.0033, found 201.9774.

b) Methyl 6-chloro-2,2-diphenyl-1,3-benzodioxole-4-carboxylate

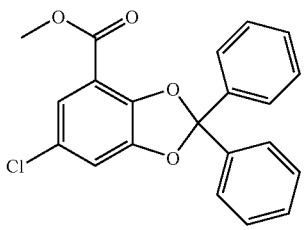

Methyl 5-chloro-2,3-dihydroxy-benzoate (330 mg, 1.63 mmol, 1 eq.) and dichlorodiphenyl-methane (470 mg, 1.96 mmol, 1.2 eq.) were reacted according to GP2, Method B.

Yield: 310 mg (52%). Colorless solid. Mp.: 151-152° C. IR (KBr): 3086w; 2947w; 1719s (CO); 1595w; 1468s; 1445m; 1360m; 1277m; 1245s; 1202s; 1166m; 1042m; 1014m; 905w; 866w; 806w; 781m; 762m; 696m. $^1$H-NMR (300 MHz, $CDCl_3$): 3.94 (s, 3 H, $CH_3$); 7.00 (d, J=2.1, 1 H, $H_{arom, Cat.}$); 7.38-7.40 (m, 6 H, $H_{arom, Ketal}$, $H_{arom, Cat.}$); 7.56-7.59 (m, 4 H, $H_{arom, Ketal}$). $^{13}$C-NMR (75 MHz, $CDCl_3$): 52.6; 111.1; 113.3; 119.4; 122.3; 126.3; 126.6; 128.6; 129.7; 139.4; 147.4; 149.3; 164.2. HR-MS (MALDI): calcd. for $C_{21}H_{16}ClO_4$ ([M+H]$^+$): 367.0737, found 367.0731. Anal. calcd. for $C_{21}H_{15}ClO_4$: C 68.77, H 4.12. found C 68.64, H 4.29.

c) 6-Chloro-2,2-diphenyl-1,3-benzodioxole-4-carboxylic acid

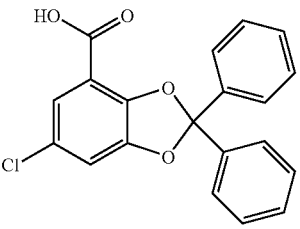

Methyl 6-chloro-2,2-diphenyl-1,3-benzodioxole-4-carboxylate (150 mg, 0.408 mmol, 1 eq.) and $LiOH.H_2O$ (52 mg, 1.23 mmol, 3 eq.) were reacted according to GP3.

Yield: 117 mg (82%). Colorless solid. Mp.: 206-207° C. IR (KBr):. 3071m; 2868m; 2616w; 1704s (CO); 1599w; 1469s; 1450m; 1407w; 1350w; 1284m; 1267m; 1238s; 1200s; 1044m; 1022m; 949w; 908w; 859w; 799m; 761m; 698m; 642w. $^1$H-NMR (300 MHz, $CDCl_3$): 7.05 (d, J=2.1, 1 H, $H_{arom, Cat.}$); 7.39-7.42 (m, 6 H, $H_{arom, Ketal}$); 7.46 (d, J=2.1, 1 H, $H_{arom, Cat.}$); 7.58-7.61 (m, 4 H, $H_{arom, Ketal}$). $^{13}$C-NMR (75 MHz, $CDCl_3$): 112.3; 114.1; 119.9; 122.6; 126.5; 126.6; 128.7; 129.8; 139.2; 148.1; 149.5; 168.5. HR-MS (MALDI): calcd. for $C_{20}H_{14}ClO_4$ ([M+H]$^+$): 353.0581, found 353.0576.

d) 6-Chloro-2,2-diphenyl-benzo[1,3]dioxole-4-carboxylic acid {3-[(3aR,4R,6R, 6aR)-6-(6-amino-9H-purin-9-yl)-2,2-dimethyl-tetrahydro-furo[3,4-d][1,3]dioxol-4-yl]-prop-2-enyl}-amide

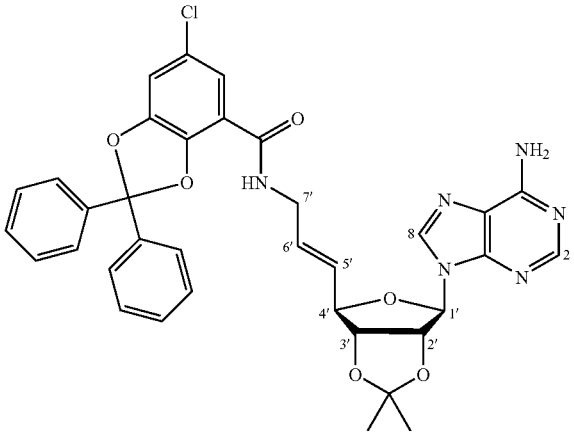

6-Cloro-2,2-diphenyl-1,3-benzodioxole-4-carboxylic acid (90 mg, 0.255 mmol, 1 eq.), EDC.HCl (75 mg, 0.383 mmol, 1.5 eq.), N-hydroxy-succinimide (40 mg, 0.332 mmol, 1.3 eq.), 9-{(3aR,4R,6R,6aR)-6-[(E)-3-aminoprop-1-enyl]-2,2-dimethylperhydrofuro[3,4-d][1,3]di-oxol-4-yl}-9H-purin-6-amine (85 mg, 0.255 mmol, 1 eq.) and $Et_3N$ (0.68 mmol) were reacted according to GP7.

Yield: 123 mg (73%). Colorless foam. Mp.: 111-113° C. IR (KBr):. 3424m; 3176m; 2986m; 1638s; 1595s; 1530m; 1462s; 1374m; 1329m; 1240s; 1208s; 1156w; 1083m; 1047m; 1017m; 971w; 867w; 778w; 698m. $^1$H-NMR (300 MHz, $CDCl_3$): 1.37 (s, 3 H, $CH_{3-exo}$); 1.61 (s, 3 H, $CH_{3-endo}$); 4.04 (m, 2 H, H—C(7'), H—C(7'')); 4.69 (m, 1 H, H—C(4')); 4.94 (dd; J=6.3, 3.6, 1 H, H—C(3')); 5.44 (dd, J=6.3, 2.1, 1 H, H—C(2')); 5.83 (m, 2 H, H—C(5'), H—C(6')); 6.06 (bs, 2 H, $NH_2$); 6.08 (d, J=2.1, 1 H, H—C(1')); 7.00 (d, J=2.1, 1 H, $H_{arom, Cat.}$); 7.06 (t, J=5.7, 1 H, NHCO); 7.35-7.40 (m, 6 H, $H_{arom, Ketal}$); 7.44-7.50 (m, 4 H, H—C(6, H$_{arom, Ketal}$); 7.56 (d, J=2.1, 1 H, H$_{arom, Cat.}$); 7.87 (s, 1 H, H—C(8)); 8.19 (s, 1 H, H—C(2)). $^{13}$C-NMR (75 MHz, CDCl$_3$): 25.6; 27.4; 41.0; 84.4; 84.7; 87.4; 90.5; 112.8; 115.0; 116.1; 119.8; 120.2; 122.3; 126.6; 127.6; 128.6; 128.8; 130.2; 130.8; 138.7; 140.4; 143.9; 148.3; 149.5; 152.2; 155.1; 162.5. HR-MS (MALDI): calcd. for C$_{35}$H$_{32}$ClN$_6$O$_6$ ([M+H]$^+$): 667.2072, found 667.2065.

e) N1-{(E)-3-[(3aR,4R,6R,6aR)-5-(6-amino-9H-purin-9-yl)-3,4-dihydroxytetrahydro-furan-2-yl]prop-2-enyl}-5-chloro-2,3-dihydroxy-benzamide

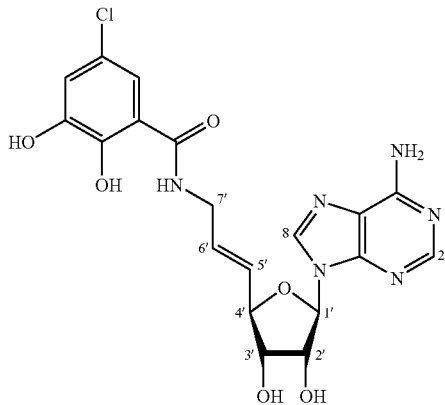

GP8, starting from the protected precursor (70 mg, 0.105 mmol) afforded the desired product as a colorless solid.

Yield: 35 mg (73%). t$_{R, analyt.}$: 13.1 min. IR (KBr): 3396 br, s; 1700s; 1636m; 1542w; 1469w; 1429w; 1326m; 1203s; 1135m; 1050w; 972w; 800w; 725w. $^1$H-NMR (500 MHz, (CD$_3$)$_2$SO): 3.93 (m, 2 H, H—C(7'), H—C(7")); 4.09 (t, J=4.9, 1 H, H—C(4')); 4.35 (m; 1 H, H—C(3')); 4.64 (t, J=5.1, 1 H, H—C(2')); 5.78-5.89 (m, 2 H, H—C(5'), H—C(6')); 5.91 (d, J=5.1, 1 H, H—C(1')); 6.92 (d, J=2.5, 1 H, H$_{arom, Cat.}$); 7.41 (d, J=2.5, 1 H, H$_{arom, Cat.}$); 8.12 (bs, 1 H, OH); 8.23 (s, 1 H, H—C(8)); 8.46 (s, 1 H, H—C(2)); 9.02 (t, J=5.4, 1 H, H—NHCO); 12.62 (bs, 1 H, OH). $^{13}$C-NMR (125 MHz, CD$_3$OD): 40.1; 73.0; 73.9; 84.3; 87.8; 115.7; 116.5; 118.3; 119.1; 121.7; 129.3; 129.4; 141.1; 147.6; 148.8; 148.9; 149.3; 153.4; 168.3. HR-MS (MALDI): calcd. for C$_{19}$H$_{20}$ClN$_6$O$_6$ ([M+H]$^+$): 463.1132, found 463.1133.

EXAMPLE 8

Preparation of N1-{(E)-3-[(3aR,4R,6R,6aR)-5-(6-amino-9H-purin-9-yl)-3,4-dihydroxytetrahydrofuran-2-yl]prop-2-enyl}-5-(4-fluoro-phenyl)-2,3-dihydroxy-benzamide a) Methyl 6-(4-fluoro-phenyl)-2,2-diphenyl-1,3-benzodioxole-4-carboxylate

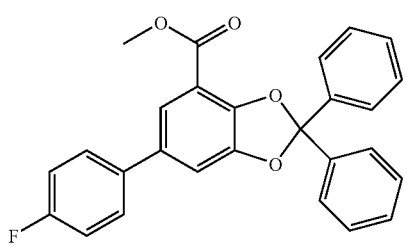

Methyl 6-bromo-2,2-diphenyl-1,3-benzodioxole-4-carboxylate (100 mg, 0.243 mmol, 1 eq.), Pd(PPh$_3$)$_4$ (15 mg, 0.012 mmol, 0.05 eq.), 4-fluorophenylboronic acid (135 mg, 0.972 mmol, 4 eq.) and K$_2$CO$_3$ (202 g, 1.46 mmol, 6 eq.) were reacted according to GP5.

Yield: 80 mg (78%). Colorless solid. Mp.: 125-127° C. IR (KBr): 3061m; 2950m; 1723s (CO); 1634w; 1603m; 1517m; 1472s; 1364m; 1257s; 1215s; 1053s; 947m; 833s; 780m; 698s; 640m. $^1$H-NMR (300 MHz, CDCl$_3$): 3.97 (s, 3 H, CH$_3$); 7.10 (tt, J=8.7, 2.0, 2 H, H$_{arom, p-F-phenyl}$); 7.20 (d, J=2.0, 1 H, H$_{arom, Cat.}$); 7.39-7.42 (m, 6 H, H$_{arom, Ketal}$); 7.45-7.50 (m, 2 H, H$_{arom, p-F-phenyl}$); 7.59 (d, J=2.0, 1 H, H$_{arom, Cat.}$); 7.62-7.65 (m, 4 H, H$_{arom, Ketal}$). $^{13}$C-NMR (75 MHz, CDCl$_3$): 52.2; 111.1; 112.7; 115.6 (d, J=21.2); 118.4; 121.1; 126.3; 128.2; 128.3; 129.2; 134.0; 136.0; 139.4; 147.4; 148.8; 162.2 (d, J=244.7); 164.8. $^{19}$F-NMR (282 MHz, CDCl$_3$): −115.9 (tt, J=9.6, 5.4). HR-MS (MALDI): calcd. for C$_{27}$H$_{19}$FO$_4$ ([M]$^+$): 426.1267, found 426.1258.

b) 6-(4-Fluoro-phenyl)-2,2-diphenyl-1,3-benzodioxole-4-carboxylic acid

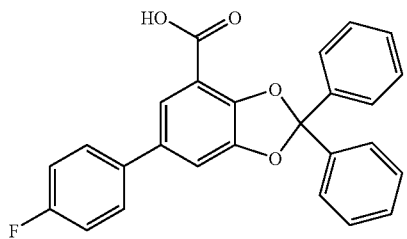

Methyl 6-(4-fluoro-phenyl)-2,2-diphenyl-1,3-benzodioxole-4-carboxylate (250 mg, 0.586 mmol, 1 eq.) and LiOH.H$_2$O (74 mg, 1.76 mmol, 3 eq.) were reacted according to GP3.

Yield: 214 mg (89%). Colorless solid. Mp.: 215-217° C. IR (KBr): 3032m; 2625w; 1687s (CO); 1635w; 1604m; 1519m; 1473s; 1422m; 1355w; 1281s; 1219s; 1179m; 1055s; 1022s; 948m; 918w; 832s; 784m; 756s; 699s; 641m. $^1$H-NMR (300 MHz, CDCl$_3$): 7.10 (t, J=8.7, 2 H, H$_{arom, p-F-phenyl}$); 7.26 (d, J=1.0, 1 H, H$_{arom, Cat.}$); 7.39-7.43 (m, 6 H, H$_{arom, Ketal}$); 7.46-7.51 (m, 2 H, H$_{arom, p-F-phenyl}$); 7.63-7.66 (m, 5 H, H$_{arom, Ketal}$, H$_{arom, Cat.}$). $^{13}$C-NMR (75 MHz, CDCl$_3$): 111.7; 112.0; 115.7 (d, J=21.2); 118.9; 121.6; 126.3; 128.3; 128.4; 129.4; 134.3; 135.9 (d, J=3.1); 139.3; 148.1; 149.0; 162.3 (d, J=245.3); 169.0. $^{19}$F-NMR (282 MHz, CDCl$_3$): −115.7 (tt, J=8.5, 5.4). HR-MS (MALDI): calcd. for C$_{27}$H$_{19}$FO$_4$Na ([M+Na]$^+$): 435.1009, found 435.1000.

c) 6-(4-Fluoro-phenyl)-2,2-diphenyl-benzo[1,3]dioxole-4-carboxylic acid {3-[(3aR,4R,6R,6aR)-6-(6-amino-9H-purin-9-yl)-2,2-dimethyl-tetrahydro-furo[3,4-d][1,3]dioxol-4-yl]-prop-2-enyl}-amide d) N1-{(E)-3-[(3aR,4R,6R,6aR)-5-(6-amino-9H-purin-9-yl)-3,4-dihydroxytetrahydrofuran-2-yl]prop-2-enyl}-5-(4-fluoro-phenyl)-2,3-dihydroxy-benzamide

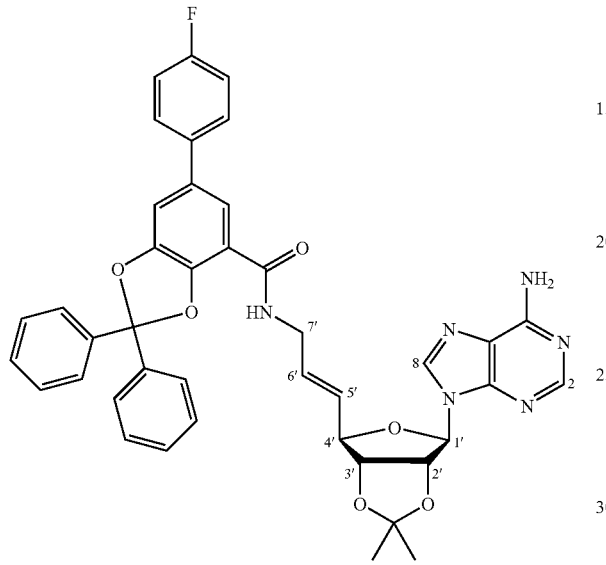

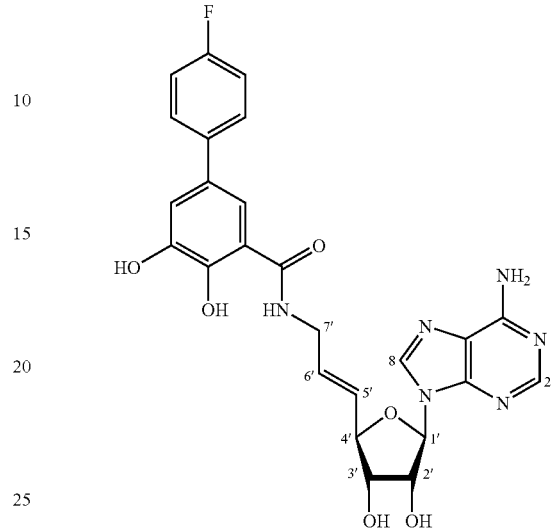

6-(4-Fluoro-phenyl)-2,2-diphenyl-1,3-benzodioxole-4-carboxylic acid (130 mg, 0.315 mmol, 1 eq.), EDC·HCl (91 mg, 0.473 mmol, 1.5 eq.), N-hydroxy-succinimide (48 mg, 0.409 mmol, 1.3 eq.), 9-{(3aR,4R,6R,6aR)-6-[(E)-3-amino-prop-1-enyl]-2,2-dimethylperhydrofuro[3,4-d][1,3]di-oxol-4-yl}-9H-purin-6-amine (90 mg, 0.271 mmol, 0.86 eq.) and Et$_3$N (0.1 mL, 0.68 mmol) were reacted according to GP7.

Yield: 130 mg (66%). Colorless foam. Mp.: 123-125° C. IR (KBr): 3425m; 3175w; 2987w; 1636s; 1598m; 1517m; 1469s; 1373w; 1274m; 1213s; 1158w; 1082m; 1052m; 1016w; 867w; 834w; 777w; 699m. $^1$H-NMR (300 MHz, CDCl$_3$): 1.38 (s, 3 H, CH$_{3-exo}$); 1.62 (s, 3 H, CH$_{3-endo}$); 4.08 (m, 2 H, H—C(7'), H—C(7")); 4.71 (m, 1 H, H—C(4')); 4.95 (dd; J=6.6, 3.6, 1 H, H—C(3')); 5.44 (dd, J=6.6, 2.3, 1 H, H—C(2')); 5.87 (m, 2 H, H—C(5'), H—C(6')); 5.93 (bs, 2 H, NH$_2$); 6.09 (d, J=2.3, 1 H, H—C(1')); 7.10 (tt, J=8.7, 2.1, 2 H, H$_{arom, p-F-phenyl}$); 7.12 (t, J=5.6, 1 H, NHCO); 7.22 (d, J=1.8, 1 H, H—C$_{arom, Cat.}$); 7.37-7.41 (m, 6 H, H$_{arom, Ketal}$); 7.47-7.56 (m, 6 H, H$_{arom, Ketal}$, H$_{arom, p-F-phenyl}$); 7.77 (d, J=1.8, H$_{arom, Cat.}$); 7.87 (s, 1 H, H—C(8)); 8.19 (s, 1 H, H—C(2)). $^{13}$C-NMR (75 MHz, CDCl$_3$): 25.5; 27.3; 40.9; 84.1; 84.5; 87.1; 90.3; 110.6; 114.7; 115.3; 115.6 (d, J=21.2); 118.8; 120.1; 121.0; 126.4; 128.2; 128.4; 128.5; 129.7; 130.7; 135.0; 136.1; 138.7; 139.9; 144.1; 147.8; 149.2; 152.0; 154.8; 162.3 (d, J=244.7); 163.1. $^{19}$F-NMR (282 MHz, CDCl$_3$): −115.9 (tt, J=8.5, 5.4). HR-MS (MALDI): calcd. for C$_{41}$H$_{35}$FN$_6$O$_6$Na ([M+Na]$^+$): 749.2500, found 749.2501.

GP8, starting from the protected precursor (70 mg, 0.096 mmol) afforded the desired product as a colorless solid.

Yield: 28 mg (56%). t$_{R, analyt.}$: 17.8 min. IR (KBr): 3407 br, s; 1700s; 1641m; 1542w; 1479w; 1314w; 1204s; 1137m; 1050w; 835w; 801w; 725w. $^1$H-NMR (500 MHz, CD$_3$OD): 4.07 (m, 2 H, H—C(7'), H—C(7")); 4.24 (t, J=5.3, 1 H, H—C(4')); 4.52 (t, J=5.3, 1 H, H—C(3')); 4.73 (t, J=4.8, 1 H, H—C(2')); 5.96 (bd, J=3.3, 2 H, H—C(5'), H—C(6')); 6.05 (d, J=4.8, 1 H, H—C(1')); 7.13 (t, J=8.8, 2 H, H$_{arom, p-F-phenyl}$); 7.20 (d, J=2.0, 1 H, H—C$_{arom, Cat.}$); 7.51 (d, J=2.0, 1 H, H$_{arom, Cat.}$); 7.58 (dd, J=8.8, 5.4, 2 H, H$_{arom, p-F-phenyl}$); 8.23 (s, 1 H, H—C(8)); 8.37 (s, 1 H, H—C(2)). $^{13}$C-NMR (125 MHz, CD$_3$OD): 41.7; 75.2; 75.6; 86.1; 90.5; 116.4 (d, J=21.3); 117.0; 117.1; 118.2; 129.3; 129.4; 130.3; 131.0; 132.3; 138.1; 143.0; 147.8; 149.0; 152.6; 149.8; 163.6 (d, J=242.5); 171.2. HR-MS (MALDI): calcd. for C$_{25}$H$_{24}$FN$_6$O$_6$ ([M+H]$^+$): 523.1741, found 523.1731.

EXAMPLE 9

Preparation of N1-{(E)-3-[(3aR,4R,6R,6aR)-5-(6-amino-9H-purin-9-yl)-3,4-dihydroxytetrahydrofuran-2-yl]prop-2-enyl}-5-p-tolyl-2,3-dihydroxy-benzamide a) Methyl 2,2-diphenyl-6-p-tolyl-1,3-benzodioxole-4-carboxylate

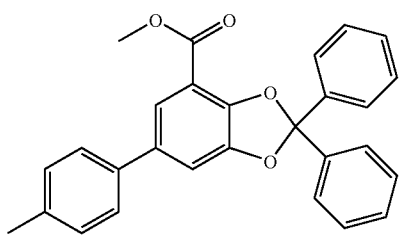

Methyl 6-bromo-2,2-diphenyl-1,3-benzodioxole-4-carboxylate (500 mg, 1.215 mmol, 1 eq.) Pd(PPh$_3$)$_4$ (70 mg, 0.06 mmol, 0.05 eq.), p-tolylboronic acid (330 mg, 2.43 mmol, 2 eq.) and K$_2$CO$_3$ (1 g, 7.29 mmol, 6 eq.) were reacted according to GP5.

Yield: 403 mg (79%). Colorless solid. Mp.: 159-160° C. IR (KBr): 3034w; 2941w; 1719s; 1470s; 1450s; 1429m; 1363w; 1255s; 1209s; 1161m; 1053s; 1028s; 944w; 817m; 775m; 702s; 640m. $^1$H-NMR (300 MHz, CDCl$_3$): 2.38 (s, 3 H, CH$_3$); 3.97 (s, 3 H, OCH$_3$); 7.22 (d, J=7.8, 2 H, H$_{arom, p-tolyl}$); 7.26 (d, J=1.8, 1 H, H$_{arom, Cat.}$); 7.38-7.44 (m, 8 H, H$_{arom, p-tolyl}$, H$_{arom, Ketal}$); 7.62-7.66 (m, 5 H, H$_{arom, Cat.}$, H$_{arom, Ketal}$). $^{13}$C-NMR (75 MHz, CDCl$_3$): 21.2; 52.2; 111.1; 112.7; 118.2; 121.0; 126.3; 126.6; 128.2; 129.2; 129.4; 135.0; 136.9; 137.0; 139.6; 147.3; 148.7; 164.9. HR-MS (MALDI): calcd. for C$_{28}$H$_{22}$O$_4$Na ([M+Na]$^+$): 445.1416, found 445.1406.

b) 2,2-Diphenyl-6-p-tolyl-1,3-benzodioxole-4-carboxylic acid

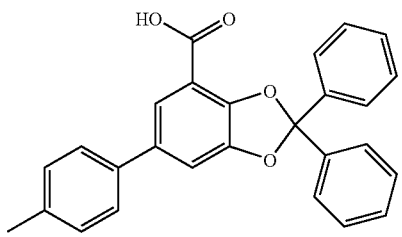

Methyl 2,2-diphenyl-6-p-tolyl-1,3-benzodioxole-4-carboxylate (280 mg, 0.662 mmol, 1 eq.) and LiOH.H$_2$O (84 mg, 2 mmol, 3 eq.) were reacted according to GP3.

Yield: 251 mg (93%). Colorless solid. Mp.: 223-224° C. IR (KBr): 3030m; 2624m; 1684s (CO); 1634m; 1602w; 1473s; 1421m; 1355w; 1282s; 1213s; 1055s; 1023s; 947m; 918w; 871w; 814m; 784m; 758m; 699s; 640m. $^1$H-NMR (300 MHz, CDCl$_3$): 2.39 (s, 3 H, CH$_3$); 7.23 (d, J=7.8, 2 H, H$_{arom, p-tolyl}$); 7.31 (d, J=1.8, 1 H, H$_{arom, Cat.}$); 7.39-7.45 (m, 8 H, H$_{arom, Ketal}$, H$_{arom, p-tolyl}$); 7.64-7.67 (m, 4 H, H$_{arom, Ketal}$); 7.71 (d, J=1.8, 1 H, H$_{arom, Cat.}$) $^{13}$C-NMR (75 MHz, CDCl$_3$): 21.1; 111.8; 112.0; 118.7; 121.5; 126.4; 126.7; 128.4; 129.4; 129.5; 135.3; 136.9; 137.2; 139.5; 148.0; 149.0; 169.4. HR-MS (MALDI): calcd. for C$_{27}$H$_{20}$O$_4$Na ([M+Na]$^+$): 431.1259, found 431.1259.

c) 2,2-diphenyl-6-p-tolyl-benzo[1,3]dioxole-4-carboxylic acid {3-[(3aR,4R,6R, 6aR)-6-(6-amino-9H-purin-9-yl)-2,2-dimethyl-tetrahydro-furo[3,4-d][1,3]dioxol-4-yl]-prop-2-enyl}-amide

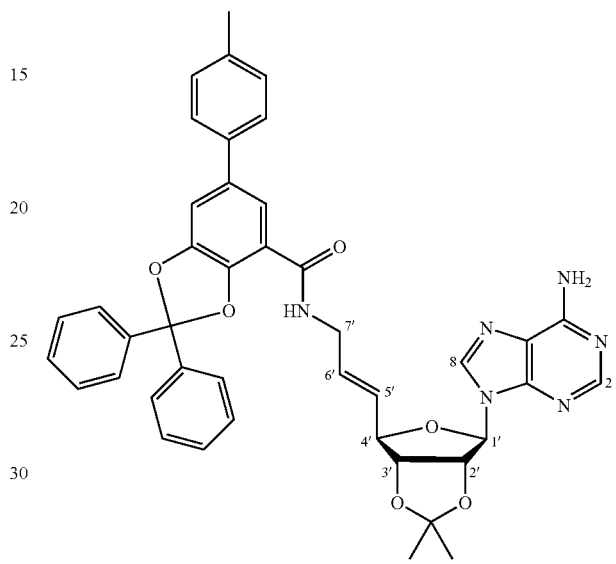

2,2-diphenyl-6-p-tolyl-1,3-benzodioxole-4-carboxylic acid (164 mg, 0.4 mmol, 1 eq.), EDC.HCl (115 mg, 0.6 mmol, 1.5 eq.), N-hydroxy-succinimide (60 mg, 0.52 mmol, 1.3 eq.), 9-{(3aR,4R,6R,6aR)-6-[(E)-3-aminoprop-1-enyl]-2,2-dimethylperhydrofuro[3,4-d][1,3]di-oxol-4-yl}-9H-purin-6-amine (90 mg, 0.271 mmol, 0.68 eq.) and Et$_3$N (0.1 mL, 0.68 mmol) were reacted according to GP7.

Yield: 111 mg (57%). Colorless foam. Mp.: 124-126° C. IR (KBr): 3423m; 3176m; 2986w; 1638s; 1597s; 1531m; 1469s; 1434m; 1373w; 1329w; 1276s; 1207s; 1156w; 1081m; 1052s; 1016m; 970w; 867m; 818m; 777m; 699m; 641m. $^1$H-NMR (300 MHz, CDCl$_3$): 1.38 (s, 3 H, CH$_{3\text{-}exo}$); 1.62 (s, 3 H, CH$_{3\text{-}endo}$); 2.37 (s, 3 H, CH$_3$); 4.09 (m, 2 H, H—C(7'), H—C(7")); 4.71 (m, 1 H, H—C(4')); 4.94 (dd; J=6.5, 3.6, 1 H, H—C(3')); 5.42 (dd, J=6.5, 2.6, 1 H, H—C(2')); 5.86 (m, 2 H, H—C(5'), H—C(6')); 6.06 (bs, 2 H, NH$_2$); 6.09 (d, J=2.6, 1 H, H—C(1')); 7.17 (t, J=5.6, 1 H, NHCO); 7.21 (d, J=8.3, 2 H, H$_{arom, p-tolyl}$); 7.26 (d, J=1.8, 1 H, H$_{arom, Cat.}$); 7.36-7.42 (m, 6 H, H$_{arom, Ketal}$); 7.46 (d, J=8.3, 2 H, H$_{arom, p-tolyl}$); 7.51-7.56 (m, 4 H, H$_{arom, Ketal}$); 7.82 (d, J=1.8, H—C$_{arom, Cat.}$); 7.88 (s, 1 H, H—C(8)); 8.19 (s, 1 H, H—C(2)). $^{13}$C-NMR (75 MHz, CDCl$_3$): 25.2; 25.5; 27.2; 40.8; 84.1; 84.4; 87.1; 90.3; 110.5; 114.7; 115.2; 118.6; 120.0; 120.8; 126.4; 126.6; 128.0; 128.3; 129.4; 129.6; 130.8; 135.9; 136.0; 137.0; 138.8; 140.0; 143.8; 147.7; 149.1; 151.5; 154.6; 163.2. HR-MS (MALDI): calcd. for $C_{42}H_{38}N_6O_6Na$ ([M+Na]$^+$): 745.2751, found 745.2750. Anal. calcd. for $C_{42}H_{38}N_6O_6$: C 69.79, H 5.30, N 11.63. found C 69.61, H 5.56, N 11.93.

d) N1-{(E)-3-[(3aR,4R,6R,6aR)-5-(6-amino-9H-purin-9-yl)-3,4-dihydroxytetrahydro-furan-2-yl]prop-2-enyl}-5-p-tolyl-2,3-dihydroxy-benzamide

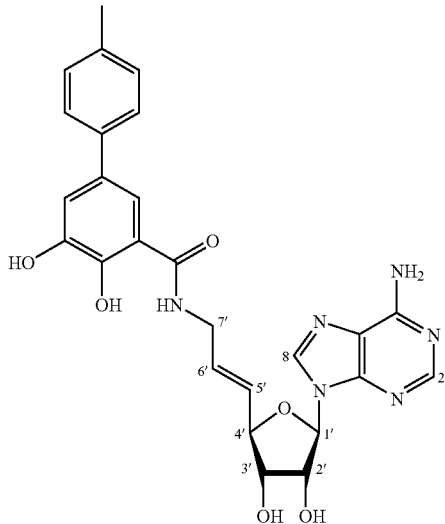

GP8, starting from the protected precursor (70 mg, 0.097 mmol) afforded the desired product as a colorless solid.

Yield: 28 mg (56%). $t_{R,\ analyt.}$: 18.3 min. IR (KBr): 3397 br, s; 1700s; 1640m; 1541w; 1478w; 1430w; 1319w; 1203s; 1137m; 1050w; 973w; 799w; 725w. $^1$H-NMR (500 MHz, $(CD_3)_2SO$): 3.97 (m, 2 H, H—C(7'), H—C(7")); 4.10 (t, J=4.9, 1 H, H—C(4')); 4.37 (t; J=4.9, 1 H, H—C(3')); 4.64 (t, J=5.1, 1 H, H—C(2')); 5.83-5.90 (m, 2 H, H—C(5'), H—C(6')); 5.91 (d, J=5.1, H—C(1')); 7.20 (d, J=1.9, 1 H, $H_{arom,\ Cat.}$); 7.22 (d, J=8.0, 1 H, $H_{arom\ p\text{-}tolyl}$); 7.51 (d, J=8.0, 1 H, $H_{arom,\ p\text{-}tolyl}$); 7.63 (d, J=1.9, 1 H, $H_{arom,\ Cat.}$); 8.12 (bs, 1 H, OH); 8.23 (s, 1 H, H—C(8)); 8.47 (s, 1 H, H—C(2)); 9.16 (t, J=5.5, 1 H, H—NHCO); 12.79 (bs, 1 H, OH). $^{13}$C-NMR (125 MHz, $(CD_3)_2SO$): 20.6; 40.1; 73.0; 73.9; 84.2; 87.7; 114.8; 114.9; 116.8; 119.0; 125.9; 129.3; 129.5; 130.1; 136.0; 136.7; 141.0; 146.5; 148.9; 149.2; 149.4; 153.5; 169.6. HR-MS (MALDI): calcd. for $C_{26}H_{26}N_6O_6Na$ ([M+Na]$^+$): 541.1812, found 541.1810.

EXAMPLE 10

Preparation of N1-{(E)-3-[(3aR,4R,6R,6aR)-5-(6-amino-9H-purin-9-yl)-3,4-dihydroxytetrahydrofuran-2-yl]prop-2-enyl}-5-thiazol-2-yl-2,3-dihydroxy-benzamide a) Methyl 2,2-diphenyl-6-thiazol-2-yl-1,3-benzodioxole-4-carboxylate

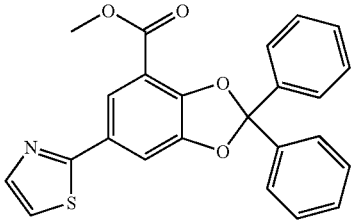

Methyl 6-bromo-2,2-diphenyl-1,3-benzodioxole-4-carboxylate (250 mg, 0.608 mmol, 1 eq.) Pd(PPh$_3$)$_4$ (70 mg, 0.06 mmol, 0.1 eq.), bis(pinacolato)diboron (200 mg, 0.79 mmol, 1.3 eq.) and KOAc (90 mg, 0.912 mmol, 1.5 eq.), then Pd(PPh$_3$)$_4$ (70 mg, 0.06 mmol, 0.1 eq.), 2-bromothiazole (110 mg, 0.67 mmol, 1.1 eq.) and K$_2$CO$_3$ (420 mg, 3.04 mmol, 5 eq.) were used according to GP6 to yield the title product as a colorless solid.

Yield: 166 mg (66%). Mp.: 154-155° C. IR (KBr): 3054w; 2947w; 1712s (CO); 1627w; 1497w; 1468s; 1447s; 1359m; 1321w; 1286m; 1254s; 1212s; 1047s; 1017s; 944w; 929w; 883w; 801m; 781m; 760m; 699s; 641m. $^1$H-NMR (300 MHz, CDCl$_3$): 3.97 (s, 3 H, OCH$_3$); 7.28 (d, J=3.2H. $H_{arom,\ thiazolyl}$); 7.37-7.42 (m, 6 H, $H_{arom,\ Ketal}$); 7.60-7.63 (m, 4 H, $H_{arom,\ Ketal}$); 7.71 (d, J=2.3, 1 H, $H_{arom,\ Cat.}$); 7.81 (d, J=3.2, 2 H, $H_{arom,\ thiazolyl}$); 8.01 (d, J=2.3, 1 H, $H_{arom,\ Cat.}$). $^{13}$C-NMR (75 MHz, CDCl$_3$): 52.5; 110.4; 113.1; 118.9; 119.4; 122.2; 126.6; 127.8; 128.6; 129.7; 139.5; 143.5; 149.4; 149.9; 164.6; 167.4. HR-MS (MALDI): calcd. for $C_{24}H_{18}NO_4S$ ([M+H]$^+$): 416.0957, found 416.0947.

b) 2,2-diphenyl-6-thiazol-2-yl-1,3-benzodioxole-4-carboxylic acid

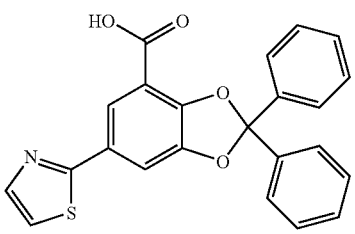

Methyl 2,2-diphenyl-6-thiazol-2-yl-1,3-benzodioxole-4-carboxylate (300 mg, 0.722 mmol, 1 eq.) and LiOH.H$_2$O (91 mg, 2.17 mmol, 3 eq.) were reacted according to GP3.

Yield: 280 mg (96%). Colorless solid. Mp.: 226-227° C. IR (KBr): 3122w; 2924w; 1702m (CO); 1629w; 1477s; 1446s; 1319w; 1266s; 1235m; 1213s; 1133s; 1048m; 1018m; 948w; 909w; 851m; 792m; 762w; 720w; 699m; 641w. $^1$H-NMR (300 MHz, (CD$_3$)$_2$SO): 7.46-7.50 (m, 6 H, $H_{arom,\ Ketal}$); 7.34-7.57 (m, 4 H, $H_{arom,\ Ketal}$); 7.76 (d, J=3.0, 2 H, H$_{arom, thiazolyl}$); 7.78 (d, J=1.8 1 H, H$_{arom, Cat.}$); 7.89 (d, J=3.0, 2 H, H$_{arom, thiazolyl}$); 7.92 (d, J=1.8, 1 H, H$_{arom, Cat.}$). $^{13}$C-NMR (75 MHz, CDCl$_3$): 109.7; 113.8; 118.3; 120.4; 121.3; 125.9; 127.3; 128.7; 129.7; 138.7; 143.7; 148.4; 148.5; 164.4; 165.7. HR-MS (MALDI): calcd. for C$_{23}$H$_{16}$NO$_4$S ([M+H]$^+$): 402.0800, found 402.0794.

c) 2,2-diphenyl-6-thiazol-2-yl-benzo[1,3]dioxole-4-carboxylic acid {3-[(3aR,4R,6R,6aR)-6-(6-amino-9H-purin-9-yl)-2,2-dimethyl-tetrahydro-furo[3,4-d][1,3]dioxol-4-yl]-prop-2-enyl}-amide

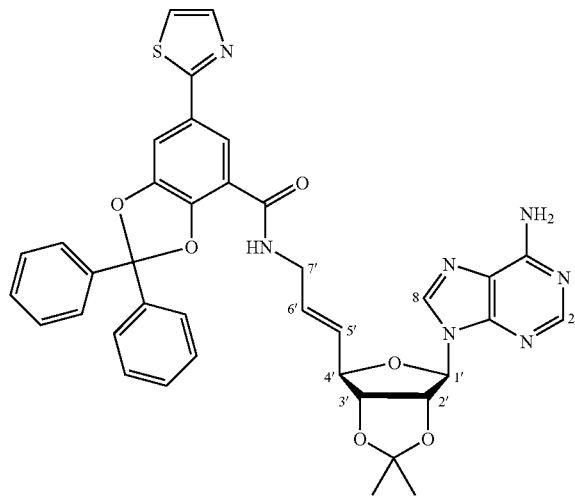

2,2-diphenyl-6-thiazol-2-yl-1,3-benzodioxole-4-carboxylic acid (160 mg, 0.4 mmol, 1 eq.), EDC.HCl (115 mg, 0.6 mmol, 1.5 eq.), N-hydroxy-succinimide (60 mg, 0.52 mmol, 1.3 eq.), 9-{(3aR,4R,6R,6aR)-6-[(E)-3-aminoprop-1-enyl]-2,2-dimethylperhydrofuro[3,4-d][1,3]di-oxol-4-yl}-9H-purin-6-amine (100 mg, 0.3 mmol, 0.75 eq.) and Et$_3$N (0.1 mL, 0.68 mmol) were reacted according to GP7.

Yield: 158 mg (74%). Colorless foam. Mp.: 132° C. IR (KBr): 3424m; 3199w; 2987w; 1639s; 1598m; 1532m; 1471m; 1440m; 1374w; 1329w; 1263m; 1212s; 1156w; 1081m; 1050m; 1015m; 867w; 779w; 700m; 643w. $^1$H-NMR (300 MHz, CDCl$_3$): 1.39 (s, 3 H, CH$_{3\text{-}exo}$); 1.62 (s, 3 H, CH$_{3\text{-}endo}$); 4.08 (m, 2 H, H—C(7'), H—C(7")); 4.76 (m, 1 H, H—C(4')); 4.93 (dd; J=6.2, 3.0, 1 H, H—C(3')); 5.42 (dd, J=6.2, 2.0, 1 H, H—C(2')); 5.82 (m, 2 H, H—C(5'), H—C(6')); 6.10 (d, J=2.0, 1 H, H—C(1')); 6.63 (bs, 2 H, NH$_2$); 7.12 (t, J=5.7, 1 H, NHCO); 7.30 (d, J=3.5, 2 H, H$_{arom, thiazolyl}$); 7.37-7.43 (m, 6 H, H—C$_{arom, Ketal}$); 7.50-7.54 (m, 4 H, H$_{arom, Ketal}$); 7.73 (d, J=1.7, 1 H, H—C$_{arom, Cat.}$); 7.81 (d, J=3.5, 2 H, H$_{arom, thiazolyl}$); 7.92 (s, 1 H, H—C(8)); 8.14 (d, J=1.7, H—C$_{arom, Cat.}$); 8.20 (s, 1 H, H—C(2)). $^{13}$C-NMR (75 MHz, CDCl$_3$): 25.4; 27.1; 40.9; 84.3; 84.4; 87.3; 90.7; 109.7; 114.6; 115.4; 119.0; 119.3; 119.9; 121.9; 126.4; 127.9; 128.4; 128.6; 129.8; 130.8; 138.4; 140.5; 143.3; 145.9; 148.0; 148.9; 149.5; 153.8; 162.6; 167.2. HR-MS (MALDI): calcd. for C$_{38}$H$_{33}$N$_7$O$_6$SNa ([M+Na]$^+$): 738.2111, found 738.2095. Anal. calcd. for C$_{42}$H$_{38}$N$_6$O$_6$: C 63.76, H 4.65, N 13.70, found C 63.55, H 4.70, N 13.68.

d) N1-{(E)-3-[(3aR,4R,6R,6aR)-5-(6-amino-9H-purin-9-yl)-3,4-dihydroxytetrahydro-furan-2-yl]prop-2-enyl}-5-thiazol-2-yl-2,3-dihydroxy-benzamide

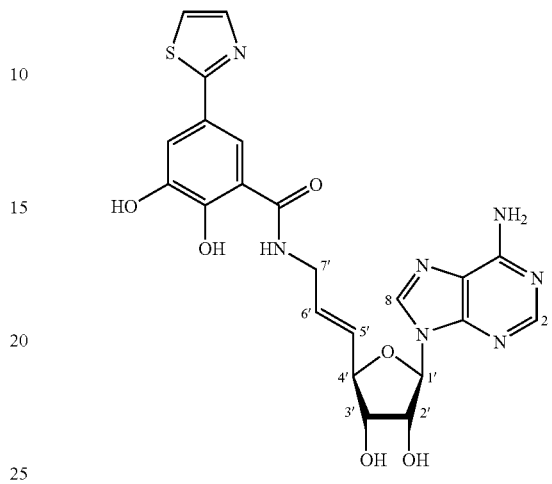

GP8, starting from the protected precursor (80 mg, 0.112 mmol) afforded the desired product as a colorless solid.

Yield: 43 mg (75%). t$_{R, analyt.}$: 13.1 min. IR (KBr): 3402 br, s; 1700s; 1642m; 1597m; 1552w; 1428w; 1318w; 1293w; 1200s; 1136m; 1050w; 837w; 800w; 723m. $^1$H-NMR (500 MHz, (CD$_3$)$_2$SO): 3.97 (m, 2 H, H—C(7'), H—C(7")); 4.10 (t, J=4.9, 1 H, H—C(4')); 4.37 (dd, J=5.0, 4.9, 1 H, H—C(3')); 4.63 (t, J=5.0, 1 H, H—C(2')); 5.82-5.91 (m, 2 H, H—C(5'), H—C(6')); 5.92 (d, J=5.0, H—C(1')); 7.53 (d, J=1.7, 1 H, H$_{arom, Cat.}$); 7.68 (d, J=3.3, 1 H, H$_{arom, thiazolyl}$); 7.83 (d, J=3.3, 1 H, H$_{arom, thiazolyl}$); 7.92 (d, J=1.7, 1 H, H$_{arom, Cat.}$); 8.52 (s, 1 H, H—C(8)); 8.56 (bs, 1 H, OH); 9.27 (t, J=5.7, 1 H, H—NHCO); 9.71 (s, 1 H, H—C(2)); 12.98 (bs, 1 H, OH). $^{13}$C-NMR (125 MHz, (CD$_3$)$_2$SO): 40.1; 73.2; 73.9; 84.3; 87.8; 115.5; 115.8; 115.9; 119.0; 119.6; 123.8; 129.3; 129.6; 141.4; 143.4; 146.8; 148.4; 148.8; 151.5; 152.7; 167.0; 168.9. HR-MS (MALDI): calcd. for C$_{22}$H$_{21}$N$_7$O$_6$SNa ([M+Na]$^+$): 534.1172, found 534.1173.

EXAMPLE 11

Preparation of N1-{(E)-3-[(3aR,4R,6R,6aR)-5-(6-amino-9H-purin-9-yl)-3,4-dihydroxytetrahydrofuran-2-yl]prop-2-enyl}-5-benzothiazol-2-yl-2,3-dihydroxy-benzamide a) Methyl 6-benzothiazol-2-yl-2,2-diphenyl-1,3-benzodioxole-4-carboxylate

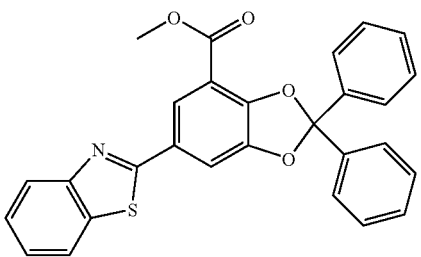

Methyl 6-bromo-2,2-diphenyl-1,3-benzodioxole-4-carboxylate (600 mg, 1.459 mmol, 1 eq.), Pd(PPh$_3$)$_4$ (85 mg, 0.073 mmol, 0.05 eq.), bis(pinacolato)diboron (480 mg, 1.9 mmol, 1.3 eq.) and KOAc (216 mg, 2.2 mmol, 1.5 eq.), then Pd(PPh$_3$)$_4$ (85 mg, 0.073 mmol, 0.05 eq.), 2-bromo-1,3-benzothiazole (375 mg, 1.75 mmol, 1.2 eq.) and K$_2$CO$_3$ (1 g, 7.3 mmol, 5 eq.) were used according to GP6 to yield the title product as a colorless solid.

Yield: 274 mg (41%). Mp.: 184-185° C. IR (KBr): 3055w; 2950w; 1718s; 1635w; 1502w; 1446s; 1368m; 1297m; 1239s; 1212s; 1163m; 1047s; 1015s; 945m; 921m; 874m; 795m; 776s; 759s; 723w; 701s; 640m. $^1$H-NMR (300 MHz, CDCl$_3$): 4.00 (s, 3 H, OCH$_3$); 7.38-7.51 (m, 8 H, H$_{arom, benzothiazole}$, H$_{arom, Ketal}$); 7.62-7.64 (m, 4 H, H$_{arom, Ketal}$); 7.86 (d, J=1.7, 1 H, H$_{arom, Cat.}$); 7.88 (d, J=9.3, 1 H, H$_{arom, benzothiazole}$); 8.04 (d, J=9.3, 1 H, H$_{arom, benzothiazole}$); 8.13 (d, J=1.7, 1 H, H$_{arom, Cat.}$). $^{13}$C-NMR (75 MHz, CDCl$_3$): 52.4; 110.6; 112.8; 119.3; 121.5; 122.9; 123.2; 125.1; 126.3; 127.5; 128.3; 129.4; 134.8; 139.1; 149.1; 150.2; 153.7; 164.1; 166.5. HR-MS (MALDI): calcd. for C$_{28}$H$_{20}$NO$_4$S ([M+H]$^+$): 466.1113, found 466.1113. Anal. calcd. for C$_{28}$H$_{19}$NO$_4$S: C 72.24, H 4.11, N 3.01. found C 72.15, H 4.03, N 3.19.

b) 2,2-diphenyl-6-benzothiazol-2-yl-1,3-benzodioxole-4-carboxylic acid

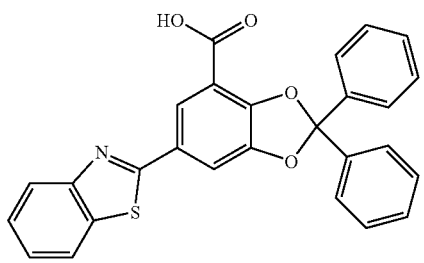

Methyl 2,2-diphenyl-6-benzothiazol-2-yl-1,3-benzodioxole-4-carboxylate (210 mg, 0.451 mmol, 1 eq.) and LiOH.H$_2$O (57 mg, 1.35 mmol, 3 eq.) were reacted according to GP3.

Yield: 201 mg (99%). Colorless solid. Mp.: 227° C. IR (KBr): 3437w; 2965w; 2610w; 1738m; 1688s; 1634w; 1460s; 1427m; 1360w; 1256s; 1237s; 1211s; 1047s; 1048m; 1015m; 999m; 928w; 878w; 788m; 760m; 726w; 699m; 641w. $^1$H-NMR (300 MHz, CDCl$_3$): 7.36-7.44 (m, 7 H, H$_{arom, benzothiazole}$, H$_{arom, Ketal}$); 7.46-7.53 (m, 1 H, H$_{arom, benzothiazole}$); 7.53-7.67 (m, 4 H, H$_{arom, Ketal}$); 7.88 (d,J=1.8, 1 H, H$_{arom, Cat.}$); 7.89 (d, J=8.7, 1 H, H$_{arom, benzothiazole}$); 8.15 (d, J=8.7, 1 H, H$_{arom, benzothiazole}$); 8.28 (d, J=1.8, 1 H, H$_{arom, Cat.}$). $^{13}$C-NMR (75 MHz, CDCl$_3$): 111.4; 112.2; 119.7; 121.5; 123.1; 123.7; 125.2; 126.3; 126.4; 127.5; 128.3; 129.5; 134.6; 138.9; 149.3; 150.9; 153.6; 166.6; 167.8. HR-MS (MALDI): calcd. for C$_{27}$H$_{18}$NO$_4$S ([M+H]$^+$): 452.0957, found 452.0955.

c) 6-Benzothiazol-2-yl-2,2-diphenyl-benzo[1,3]dioxole-4-carboxylic acid {3-[(3aR,4R,6R,6aR)-6-(6-amino-9H-purin-9-yl)-2,2-dimethyl-tetrahydro-furo[3,4-d][1,3]dioxol-4-yl]-prop-2-enyl}-amide

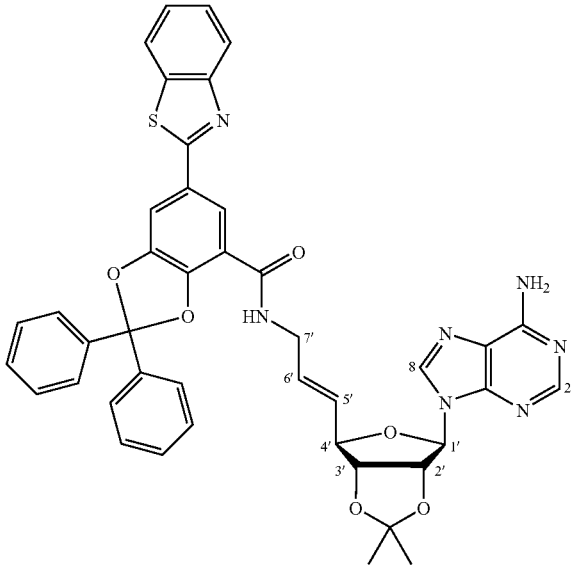

2,2-diphenyl-6-benzothiazol-2-yl-1,3-benzodioxole-4-carboxylic acid (170 mg, 0.38 mmol, 1 eq.), EDC.HCl (110 mg, 0.565 mmol, 1.5 eq.), N-hydroxy-succinimide (57 mg, 0.49 mmol, 1.3 eq.), 9-{(3aR,4R,6R,6aR)-6-[(E)-3-amino-prop-1-enyl]-2,2-dimethylperhydrofuro[3,4-d][1,3]di-oxol-4-yl}-9H-purin-6-amine (100 mg, 0.3 mmol, 0.8 eq.) Et$_3$N (0.1 mL, 0.68 mmol) were reacted according to GP7.

Yield: 151 mg (66%). Colorless foam. Mp.: 138-140° C. IR (KBr): 3424m; 2982w; 1635s; 1596m; 1533m; 1463m; 1436s; 1373w; 1259m; 1208s; 1155w; 1081m; 1048m; 1011m; 867w; 759w; 699w; 641w. $^1$H-NMR (300 MHz, CDCl$_3$): 1.38 (s, 3 H, CH$_{3-exo}$); 1.62 (s, 3 H, CH$_{3-endo}$); 4.07 (m, 2 H, H—C(7'), H—C(7")); 4.72 (m, 1 H, H—C(4')); 4.95 (dd; J=6.3, 3.6, 1 H, H—C(3')); 5.44 (dd, J=6.3, 2.3, 1 H, H—C(2')); 5.85 (m, 2 H, H—C(5'), H—C(6')); 6.09 (d, J=2.3, 1 H, H—C(1')); 6.17 (bs, 2 H, NH$_2$); 7.13 (t, J=5.7, 1 H, NHCO); 7.34-7.49 (m, 8 H, H$_{arom, Ketal}$, H$_{arom, benzoth.}$); 7.49-7.55 (m, 4 H, H$_{arom, Ketal}$); 7.87 (s, 1 H, H—C(8)); 7.88 (d, J=7.8, 2 H, H$_{arom, benzoth.}$); 7.91 (d, J=1.9, 1 H, H$_{arom, Cat.}$); 7.81 (d, J=7.8, 2 H, H$_{arom, benzoth.}$); 8.20 (s, 1 H, H—C(2)); 8.22 (d, J=1.9, H$_{arom, Cat.}$). $^{13}$C-NMR (75 MHz, CDCl$_3$): 25.4; 27.2; 40.9; 84.1; 84.4; 87.2; 90.3; 110.1; 114.6; 115.4; 119.5; 120.0; 121.5; 122.9; 123.2; 125.1; 126.2; 126.4; 128.3; 128.4; 128.6; 129.8; 130.5; 135.0; 138.3; 140.0; 146.7; 148.1; 149.1; 151.5; 153.7; 154.7; 162.4; 166.7. HR-MS (MALDI): calcd. for C$_{42}$H$_{35}$N$_7$O$_6$SNa ([M+Na]$^+$): 788.2267, found 788.2266.

d) N1-{(E)-3-[(3aR,4R,6R,6aR)-5-(6-amino-9H-purin-9-yl)-3,4-dihydroxytetrahydrofuran-2-yl]prop-2-enyl}-5-benzothiazol-2-yl-2,3-dihydroxybenzamide

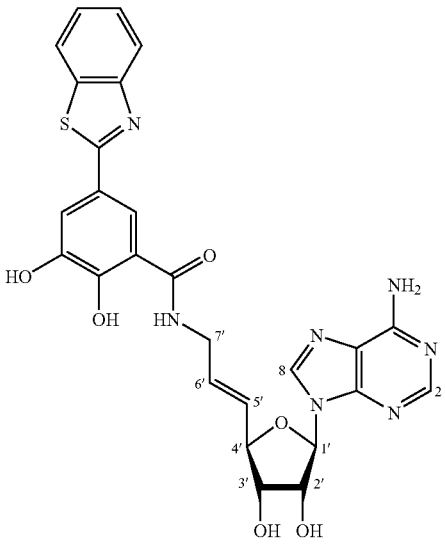

GP8, starting from the protected precursor (83 mg, 0.108 mmol) afforded the desired product as a yellowish solid.

Yield: 38 mg (64%). $t_{R, \, analyt.}$: 17.7 min. IR (KBr): 3377 br, s; 1685s; 1645m; 1544w; 1436m; 1303m; 1202s; 1137m; 834w; 800w; 759w; 724w. $^1$H-NMR (500 MHz, (CD$_3$)$_2$SO): 4.01 (m, 2 H, H—C(7'), H—C(7'')); 4.13 (t, J=4.9, 1 H, H—C(4')); 4.39 (dd; J=6.7, 4.9, 1 H, H—C(3')); 4.66 (t, J=5.0, 1 H, H—C(2')); 5.80-5.96 (m, 2 H, H—C(5'), H—C(6')); 5.93 (d, J=5.0, H—C(1')); 7.43 (t, J=8.0, 1 H, H$_{arom, benzoth.}$); 7.53 (t, J=8.0, 1 H, H$_{arom, benzoth.}$); 7.68 (d, J=2.0, 1 H, H$_{arom, Cat.}$); 8.00 (d, J=8.0, 1 H, H$_{arom, benzoth.}$); 8.09 (d, J=2.0, 1 H, H$_{arom, Cat.}$); 8.12 (d, J=8.0, 1 H, H$_{arom, benzoth.}$); 8.27 (s, 1 H, H—C(8)); 9.37 (t, J=5.3, 1 H, H—NHCO); 9.86 (s, 1 H, H—C(2)); 13.19 (bs, 1 H, OH). $^{13}$C-NMR (125 MHz, (CD$_3$)$_2$SO): 40.1; 73.0; 73.9; 84.2; 87.7; 115.4; 115.5; 116.4; 119.1; 122.3; 122.4; 123.3; 125.2; 126.6; 129.4; 129.5; 134.4; 141.0; 147.0; 149.0; 149.1; 152.6; 153.3; 153.5; 167.0; 168.7. HR-MS (MALDI): calcd. for C$_{26}$H$_{23}$N$_7$O$_6$SNa ([M+Na]$^+$): 584.1328, found 584.1330.

EXAMPLE 12

Preparation of N1-{(E)-3-[(3aR,4R,6R,6aR)-5-(6-amino-9H-purin-9-yl)-3,4-dihydroxytetrahydrofuran-2-yl]prop-2-enyl}-5-pyridin-4-yl-2,3-dihydroxybenzamide a) Methyl 2,2-diphenyl-6-pyridin-4-yl-1,3-benzodioxole-4-carboxylate

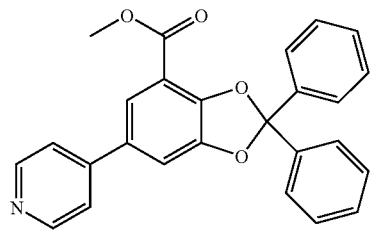

Methyl 6-bromo-2,2-diphenyl-1,3-benzodioxole-4-carboxylate (400 mg, 0.973 mmol, 1 eq.), Pd(PPh$_3$)$_4$ (100 mg, 0.087 mmol, 0.09 eq.), bis(pinacolato)diboron (320 mg, 1.26 mmol, 1.3 eq.) and KOAc (150 mg, 1.5 mmol, 1.5 eq.), then Pd(PPh$_3$)$_4$ (112 mg, 0.097 mmol, 0.1 eq.), 2-bromo-pyridine hydrochloride (265 mg, 1.36 mmol, 1.4 eq.) and K$_2$CO$_3$ (680 mg, 4.9 mmol, 5 eq.) were used according to GP6 to yield the title product as a colorless solid.

Yield: 264 mg (67%). Mp.: 151-152° C. IR (KBr): 3030w; 2954w; 1718s; 1635w; 1594m; 1475s; 1439s; 1418m; 1325m; 1291m; 1269s; 1225s; 1180m; 1054s; 1038m; 1018m; 947w; 927w; 886w; 815m; 782m; 753m; 703m; 693m; 641m. $^1$H-NMR (300 MHz, CDCl$_3$): 3.98 (s, 3 H, OCH$_3$); 7.31 (d, J=1.8, 1 H, H$_{arom, Cat.}$); 7.39-7.41 (m, 6 H, H$_{arom, Ketal}$); 7.48 (dd, J=4.7, 1.8, 1 H, H$_{arom, pyridyl}$); 7.61-7.64 (m, 4 H, H$_{arom, Ketal}$); 7.75 (d, J=1.7, 1 H, H$_{arom, Cat.}$); 8.63 (dd, J=4.7, 1.8, 1 H, H$_{arom pyridyl}$). $^{13}$C-NMR (75 MHz, CDCl$_3$): 52.6; 110.9; 113.4; 119.4; 121.6; 122.3; 126.6; 128.6; 129.8; 131.7; 139.5; 148.0; 149.4; 149.7; 149.8 164.9. HR-MS (MALDI): calcd. for C$_{26}$H$_{20}$NO$_4$ ([M+H]$^+$): 410.1392, found 410.1383.

b) 2,2-diphenyl-6-pyridin-4-yl-1,3-benzodioxole-4-carboxylic acid

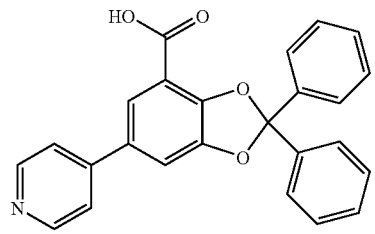

Methyl 2,2-diphenyl-6-pyridin-4-yl-1,3-benzodioxole-4-carboxylate (250 mg, 0.61 mmol, 1 eq.) and LiOH.H$_2$O (80 mg, 1.84 mmol, 3 eq.) were reacted according to GP3.

Yield: 220 mg (92%). Grayish solid. Mp.: 266° C. (dec.). IR (KBr): 3446br, w; 3061w; 2447br, w; 1696m; 1632w; 1603m; 1469s; 1440m; 1373w; 1326m; 1273s; 1213s; 1182m; 1054s; 1015m; 949w; 92$^1$w; 906w; 832m; 789w; 777w; 765m; 701m; 640w. $^1$H-NMR (300 MHz, (CD$_3$)$_2$SO): 7.46-7.48 (m, 6 H, H$_{arom, Ketal}$); 7.52-7.58 (m, 4 H, H$_{arom, Ketal}$); 7.67 (d, J=4.4, 2 H, H$_{arom pyridyl}$); 7.73 (m, 2 H, H$_{arom, Cat.}$); 8.59 (d, J=4.4, 2 H, H$_{arom, pyridyl}$). $^{13}$C-NMR (75 MHz, CDCl$_3$): 110.7; 113.9; 117.9; 120.8; 121.6; 125.8; 128.6; 129.6; 131.1; 138.7; 145.6; 147.8; 148.5; 150.0; 164.6. HR-MS (MALDI): calcd. for C$_{25}$H$_{18}$NO$_4$ ([M+H]$^+$): 396.1236, found 396.1234.

c) 2,2-Diphenyl-6-pyridin-4-yl-benzo[1,3]dioxole-4-carboxylic acid {3-[(3aR,4R,6R,6aR)-6-(6-amino-9H-purin-9-yl)-2,2-dimethyl-tetrahydro-furo[3,4-d][1,3]dioxol-4-yl]-prop-2-enyl}-amide

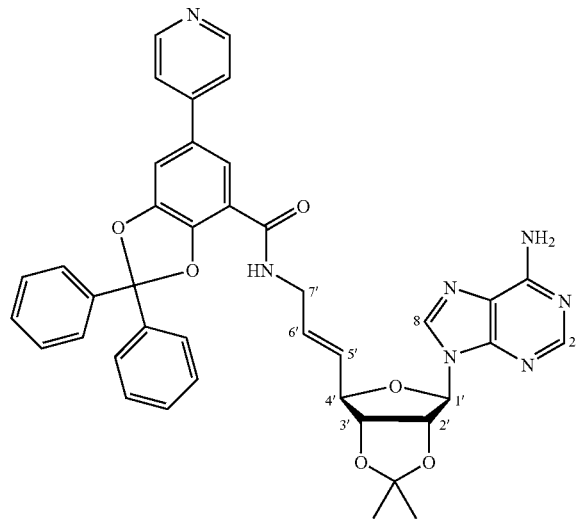

The reaction of 2,2-diphenyl-6-pyridin-4-yl-1,3-benzodioxole-4-carboxylic acid (160 mg, 0.405 mmol, 1 eq.), EDC.HCl (117 mg, 0.608 mmol, 1.5 eq.), N-hydroxysuccinimide (61 mg, 0.527 mmol, 1.3 eq.), 9-{(3aR,4R,6R,6aR)-6-[(E)-3-aminoprop-1-enyl]-2,2-dimethyl-perhydro-furo[3,4-d][1,3]di-oxol-4-yl}-9H-purin-6-amine (100 mg, 0.3 mmol, 0.74 eq.) and Et$_3$N (0.1 mL, 0.68 mmol) was carried out in CH$_2$Cl$_2$/DMF 1:1 according to GP7.

Yield: 95 mg (45%). Yellowish foam. IR (neat, dropcast from CH$_2$Cl$_2$): 3321br, w; 2963m; 1696m; 1645m; 1597m; 1530w; 1468s; 1435w; 1374w; 1261s; 1213s; 1053s; 867w; 799m; 699m; 642w. $^1$H-NMR (300 MHz, CDCl$_3$): 1.37 (s, 3 H, CH$_{3\text{-}exo}$); 1.61 (s, 3 H, CH$_{3\text{-}endo}$); 4.08 (m, 2 H, H—C(7'), H—C(7")); 4.70 (m, 1 H, H—C(4')); 4.96 (dd; J=6.3, 3.9, 1 H, H—C(3')); 5.45 (dd, J=6.3, 2.3, 1 H, H—C(2')); 5.86 (m, 2 H, H—C(5'), H—C(6')); 5.98 (bs, 2 H, NH$_2$); 6.08 (d, J=2.3, 1 H, H—C(1')); 7.16 (t, J=5.7, 1 H, NHCO); 7.31 (d, J=1.7, 1 H, H$_{arom, Cat.}$); 7.36-7.42 (m, 6 H, H$_{arom, Ketal}$); 7.47-7.55 (m, 6 H, H$_{arom, Ketal}$, H$_{arom, pyridyl}$); 7.86 (s, 1 H, H—C(8)); 7.92 (d, J=1.7, 2 H, H$_{arom, Cat.}$); 8.18 (s, 1 H, H—C(2)); 8.61 (d, J=6.3, H$_{arom, pyridyl}$). $^{13}$C-NMR (75 MHz, CDCl$_3$): 25.6; 27.4; 41.1; 84.3; 84.7; 87.4; 90.5; 110.4; 114.9; 116.0; 119.7; 120.4; 121.6; 122.0; 126.2; 126.7; 128.8; 130.2; 130.8; 132.8; 138.8; 140.1; 145.9; 147.6; 148.6; 149.6; 150.2; 153.0; 155.6; 163.1. HR-MS (MALDI): calcd. for C$_{40}$H$_{35}$N$_7$O$_6$Na ([M+Na]$^+$): 732.2547, found 732.2549.

d) N1-{(E)-3-[(3aR,4R,6R,6aR)-5-(6-amino-9H-purin-9-yl)-3,4-dihydroxytetrahydro-furan-2-yl]prop-2-enyl}-5-pyridin-4-yl-2,3-dihydroxy-benzamide

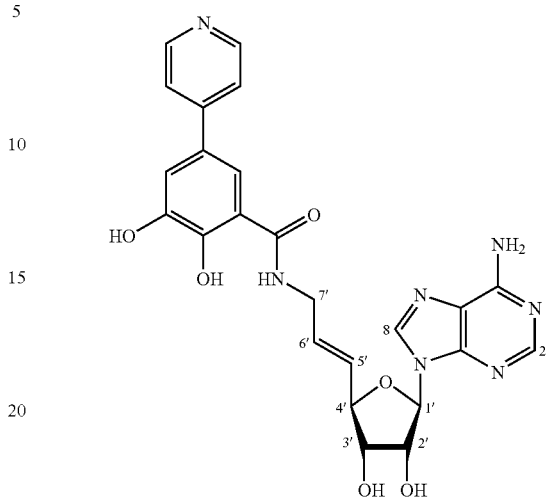

GP8, starting from the protected precursor (35 mg, 0.049 mmol) afforded the desired product as a yellowish solid.

Yield: 15 mg (63%). Mp.: 133-137° C. (dec.). t$_{R, analyt.}$: 10.6 min. IR (KBr): 3384 br, s; 1684s; 1633m; 1474w; 1431m; 1321m; 1202s; 1134m; 832w; 723w. $^1$H-NMR (500 MHz, (CD$_3$)$_2$SO): 4.02 (m, 2 H, H—C(7'), H—C(7")); 4.11 (t, J=4.8, 1 H, H—C(4')); 4.37 (m; 1 H, H—C(3')); 4.67 (t, J=5.1, 1 H, H—C(2')); 5.82-5.94 (m, 2 H, H—C(5'), H—C(6')); 5.91 (d, J=5.1, H—C(1')); 7.52 (d, J=1.8, 1 H, H$_{arom, Cat.}$); 7.85 (bs, 1 H, OH); 8.01 (d, J=1.8, 1 H, H$_{arom, Cat.}$); 8.08 (d, J=5.2, 1 H, H$_{arom, pyridyl}$); 8.17 (s, 1 H, H—C(8)); 8.42 (s, 1 H, H—C(2)); 8.79 (d, J=5.2, 1 H, H$_{arom, pyridyl}$); 9.23 (t, J=5.5, 1 H, H—NHCO); 9.69 (bs, 1 H, OH); 13.35 (bs, 1 H, OH). $^{13}$C-NMR (125 MHz, (CD$_3$)$_2$SO): 40.1; 72.9; 73.9; 84.1; 87.7; 115.2; 117.0; 117.2; 119.1; 121.8; 124.8; 129.1; 129.6; 140.7; 144.9; 147.3; 149.0; 150.3; 152.6; 154.2; 169.2. HR-MS (MALDI): calcd. for C$_{24}$H$_{23}$N$_7$O$_6$Na ([M+Na]$^+$): 528.1608, found 528.1607.

EXAMPLE 13

Preparation of N1-{(E)-3-[(3aR,4R,6R,6aR)-5-(6-amino-9H-purin-9-yl)-3,4-dihydroxytetrahydrofuran-2-yl]prop-2-enyl}-5-(4-methyl-benzyl)-2,3-dihydroxy-benzamide a) Methyl 2,2-diphenyl-6-(4-methyl-benzyl)-1,3-benzodioxole-4-carboxylate

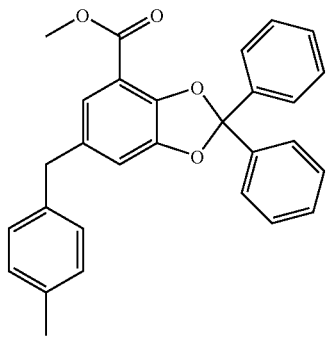

Methyl 6-bromo-2,2-diphenyl-1,3-benzodioxole-4-carboxylate (200 mg, 1.486 mmol, 1 eq.), Pd(PPh$_3$)$_4$ (57 mg, 0.049 mmol, 0.1 eq.), bis(pinacolato)diboron (160 mg, 0.632 mmol, 1.3 eq.) and KOAc (72 mg, 0.73 mmol, 1.5 eq.), then Pd(PPh$_3$)$_4$ (57 mg, 0.049 mmol, 0.1 eq.), 1-bromomethyl-4-methyl-benzene (117 mg, 0.63 mmol, 1.3 eq.) and K$_2$CO$_3$ (336 mg, 2.43 mmol, 5 eq.) were reacted according to GP6 to yield the title product as a colorless, very slowly solidifying oil.

Yield: 197 mg (80%). IR (neat): 3030w; 2950w; 1722s; 1636w; 1603w; 1477s; 1449s; 1381w; 1251s; 1202s; 1047s; 1019m; 948w; 918w; 829w; 782m; 763m; 699m; 642m. $^1$H-NMR (300 MHz, CDCl$_3$): 2.32 (s, 3 H, CH$_3$); 3.85 (s, 2H, CH$_2$); 3.93 (s, 3H, OCH$_3$); 6.83 (d, J=1.8, 1 H, H$_{arom, Cat.}$); 7.06 (d, J=8.6, 2 H, H$_{arom, p-Tol.}$); 7.10 (d, J=8.6, 1 H, H$_{arom, p-Tol.}$); 7.29 (d, J=1.8, 1 H, H$_{arom, Cat.}$); 7.35-7.38 (m, 6 H, H$_{arom, Ketal}$); 7.57-7.60 (m, 4 H, H$_{arom, Ketal}$). $^{13}$C-NMR (75 MHz, CDCl$_3$): 21.0; 41.1; 52.0; 112.2; 113.1; 117.9; 122.3; 126.3; 128.2; 128.7; 129.1; 129.2; 134.9; 135.8; 137.5; 139.8; 146.6; 148.5; 165.2. HR-MS (MALDI): calcd. for C$_{29}$H$_{24}$O$_4$Na ([M+Na]$^+$): 459.1572, found 459.1573.

b) 2,2-diphenyl-6-(4-methyl-benzyl)-1,3-benzodioxole-4-carboxylic acid

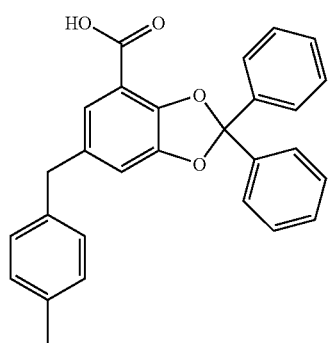

Methyl 2,2-diphenyl-6-(4-methyl-benzyl)-1,3-benzodioxole-4-carboxylate (300 mg, 0.69 mmol, 1 eq.) and LiOH.H$_2$O (87 mg, 2.06 mmol, 3 eq.) were reacted according to GP3.

Yield: 287 mg (99%). Colorless solid. Mp.: 211-213° C. IR (KBr): 3434br, w; 2904w; 2571w; 1685m; 1638w; 1604w; 1479m; 1464w; 1304m; 1252m; 1209s; 1050m; 1027m; 947m; 921w; 828m; 784m; 750w; 797m; 641w. $^1$H-NMR (300 MHz, CDCl$_3$): 2.32 (s, 3 H, CH$_3$); 3.86 (s, 2H, CH$_2$); 6.88 (d, J=1.2, 1 H, H$_{arom, Cat.}$); 7.07 (d, J=8.4, 2 H, H$_{arom, p-Tol.}$); 7.11 (d, J=8.4, 1 H, H$_{arom, p-Tol.}$); 7.34-7.40 (m, 7 H, H$_{arom, Cat.}$) H$_{arom, Ketal}$); 7.58-7.62 (m, 4 H, H$_{arom, Ketal}$). $^{13}$C-NMR (75 MHz, CDCl$_3$): 21.0; 41.1; 111.3; 113.9; 118.4; 122.7; 126.4; 128.3; 128.7; 129.3; 135.2; 135.9; 137.4; 139.6; 147.3; 148.6; 169.7. HR-MS (MALDI): calcd. for C$_{28}$H$_{22}$O$_4$Na ([M+Na]$^+$): 445.1416, found 445.1415.

c) 2,2-Diphenyl-6-(4-methyl-benzyl)-benzo[1,3]dioxole-4-carboxylic acid {3-[(3aR,4R,6R, 6aR)-6-(6-amino-9H-purin-9-yl)-2,2-dimethyl-tetrahydro-furo[3,4-d][1,3]dioxol-4-yl]-prop-2-enyl}-amide

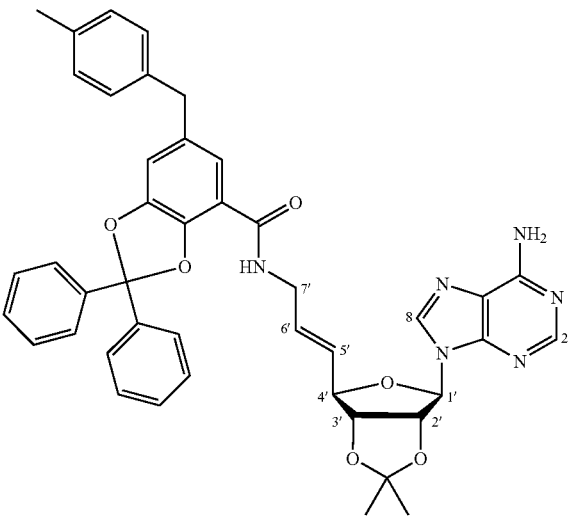

2,2-diphenyl-6-(4-methyl-benzyl)-1,3-benzodioxole-4-carboxylic acid (165 mg, 0.39 mmol, 1 eq.), EDC.HCl (115 mg, 0.59 mmol, 1.5 eq.), N-hydroxy-succinimide (57 mg, 0.49 mmol, 1.3 eq.), 9-{(3aR,4R,6R,6aR)-6-[(E)-3-amino-prop-1-enyl]-2,2-dimethylperhydrofuro[3,4-d][1,3]di-oxol-4-yl}-9H-purin-6-amine (100 mg, 0.3 mmol, 0.77 eq.) and Et$_3$N (0.1 mL, 0.68 mmol) were reacted according to GP7.

Yield: 172 mg (78%). Colorless foam. Mp.: 107-110° C. IR (KBr): 3426m; 3176w; 2986w; 1636s; 1597s; 1529m; 1474s; 1440m; 1374w; 1328m; 1254s; 1207s; 1156w; 1082m; 1049m; 1020m; 868w; 776w; 699m; 642w. $^1$H-NMR (300 MHz, CDCl$_3$): 1.38 (s, 3 H, CH$_{3-exo}$); 1.62 (s, 3 H, CH$_{3-endo}$); 2.29 (s, 3 H, CH$_{3, p-Tol.}$); 3.87 (s, 2H, CH$_{2, benzyl.}$); 4.05 (m, 2 H, H—C(7'), H—C(7'')); 4.71 (m, 1 H, H—C(4')); 4.91 (dd; J=6.4, 3.6, 1 H, H—C(3')); 5.38 (dd, J=6.4, 2.4, 1 H, H—C(2')); 5.83 (m, 2 H, H—C(5'), H—C(6')); 6.09 (d, J=2.4, 1 H, H—C(1')); 6.40 (bs, 2 H, NH$_2$); 6.83 (d, J=1.8, 1 H, H$_{arom, Cat.}$); 7.07 (s, 4 H, H$_{arom, p-tolyl}$); 7.14 (t, J=5.7, 1 H, NHCO); 7.33-7.38 (m, 6H, H$_{arom, Ketal}$); 7.45-7.49 (m, 5 H, H$_{arom, Ketal}$, H$_{arom, Cat.}$); 7.91 (s, 1 H, H—C(8)); 8.16 (s, 1 H, H—C(2)). $^{13}$C-NMR (75 MHz, CDCl$_3$): 21.1; 25.4; 27.2; 40.7; 41.3; 84.2; 84.4; 87.1; 90.4; 112.5; 114.7; 114.8; 118.2; 119.9; 122.1; 126.3; 127.7; 128.3; 128.6; 129.1; 129.5; 131.0; 135.7; 136.0; 137.5; 138.9; 140.5; 143.0; 147.3; 148.9; 149.8; 153.8; 163.4. HR-MS (MALDI): calcd. for C$_{43}$H$_{40}$N$_6$O$_6$Na ([M+Na]$^+$): 759.2907, found 759.2909. Anal. calcd. for C$_{43}$H$_{40}$N$_6$O$_6$: C 70.09, H 5.47, N 11.41. found C 69.89, H 5.60, N 11.33.

d) N1-{(E)-3-[(3aR,4R,6R,6aR)-5-(6-amino-9H-purin-9-yl)-3,4-dihydroxytetrahydrofuran-2-yl]prop-2-enyl}-5-(4-methyl-benzyl)-2,3-dihydroxybenzamide

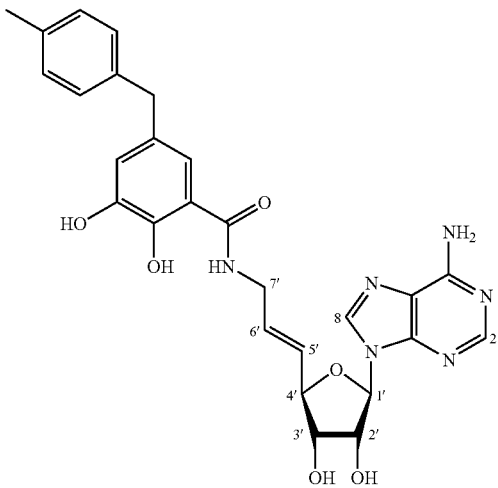

GP8, starting from the protected precursor (90 mg, 0.122 mmol) afforded the desired product as a colorless solid.

Yield: 63 mg (97%). $t_{R,\ analyt.}$: 15.8 min. IR (KBr): 3384 br, s; 1700s; 1640m; 1596m; 1534w; 1513w; 1484w; 1437m; 1324m; 1290w; 1205s; 1133m; 1048w; 972w; 836w; 799w. $^1$H-NMR (500 MHz, CD$_3$OD): 2.25 (s, 3 H, ArCH$_3$); 3.79 (s, 2H, CH$_{2,\ benzyl}$); 4.03 (m, 2 H, H—C(7'), H—C(7")); 4.22 (t, J=5.0, 1 H, H—C(4')); 4.51 (m, 1 H, H—C(3')); 4.73 (t, J=4.9, 1 H, H—C(2')); 5.93 (m, 2 H, H—C(5'), H—C(6')); 6.05 (d, J=4.9, H—C(1')); 6.76 (d, J=2.1, 1 H, H$_{arom,\ Cat.}$); 7.04 (s, 4 H, H$_{arom,\ p\text{-}Tol.}$); 7.14 (d, J=2.1, 1 H, H$_{arom,\ Cat.}$); 8.17 (s, 1 H, H—C(8)); 8.39 (s, 1 H, H—C(2)). $^{13}$C-NMR (75 MHz, CD$_3$OD): 21.1; 41.6; 41.9; 75.3; 75.7; 86.2; 90.7; 116.5; 118.8; 120.6; 120.8; 129.7; 130.1; 130.2; 131.2; 133.6; 136.7; 139.7; 143.5; 147.3; 147.6; 148.5; 150.2; 153.4; 171.3. HR-MS (MALDI): calcd. for $C_{27}H_{28}N_6O_6Na$ ([M+Na]$^+$): 555.1968, found 555.1957.

EXAMPLE 14

Preparation of N1-{(E)-3-[(3aR,4R,6R,6aR)-5-(6-amino-9H-purin-9-yl)-3,4-dihydroxytetrahydrofuran-2-yl]prop-2-enyl}-5-dimethylcarbamoyl-2,3-dihydroxy-benzamide a) 6-Dimethylcarbamoyl-2,2-diphenyl-1,3-benzodioxole-4-carboxylic acid

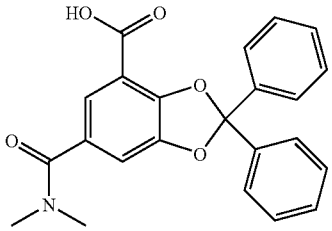

6-Bromo-2,2-diphenyl-1,3-benzodioxole-4-carboxylic acid (200 mg, 0.486 mmol), LiH (10 mg, 0.97 mmol, 2 eq.) and dimethylcarbamoylchloride (0.18 mL, 1.94 mmol, 4 eq.) as the electrophile were reacted according to GP4, Method B. The crude product was purified using flash chromatography (silica gel, hexane/EtOAc/AcOH 67:30:3) to give the title compound as a colorless solid.

Yield: 40 mg (21%). Mp.: 207-208° C. IR (KBr): 3417w; 2935w; 1718s; 1635m; 1607s; 1448s; 1415m; 1247s; 1207s; 1075w; 1041s; 1023s; 949m; 881m; 788m; 765m; 701s; 643m. $^1$H-NMR (300 MHz, CDCl$_3$): 3.06 (bs, 6 H, CH$_3$); 7.20 (d, J=1.5, 1 H, H$_{arom,\ Cat.}$); 7.37-7.41 (m, 6 H, H$_{arom,\ Cat.}$); 7.56 (d, J=1.5, 1 H, H$_{arom,\ Cat.}$); 7.58-7.62 (m, 4 H, H$_{arom,\ Ketal}$). $^{13}$C-NMR (75 MHz, CDCl$_3$): 35.8; 40.0; 111.2; 112.4; 119.3; 122.7; 126.4; 128.4; 129.4; 129.5; 139.1; 148.8; 149.8; 168.5; 170.1. HR-MS (MALDI): calcd. for $C_{23}H_{20}NO_4$ ([M+H]$^+$): 390.1341, found 390.1340.

b) 6-Dimethylcarbamoyl-2,2-diphenyl-benzo[1,3]dioxole-4-carboxylic acid {3-[(3aR,4R,6R,6aR)-6-(6-amino-9H-purin-9-yl)-2,2-dimethyl-tetrahydro-furo[3,4-d][1,3]dioxol-4-yl]-prop-2-enyl}-amide

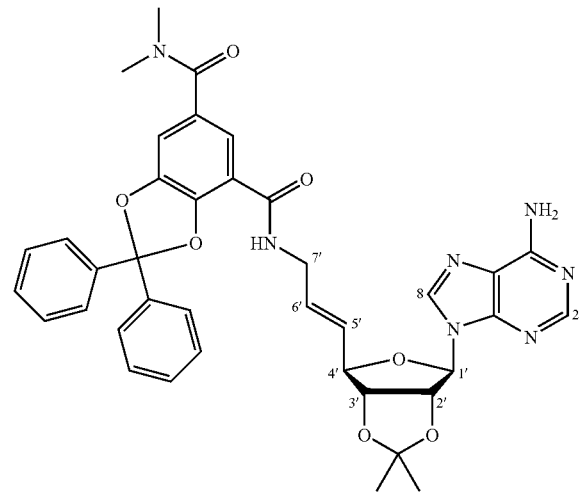

6-Dimethylcarbamol-2,2-diphenyl-1,3-benzodioxole-4-carboxylic acid (120 mg, 0.31 mmol, 1 eq.), EDC.HCl (90 mg, 0.46 mmol, 1.5 eq.), N-hydroxy-succinimide (46 mg, 0.4 mmol, 1.3 eq.), 9-{(3aR,4R,6R,6aR)-6-[(E)-3-amino-prop-1-enyl]-2,2-dimethylperhydrofuro[3,4-d][1,3]di-oxol-4-yl}-9H-purin-6-amine (93 mg, 0.28 mmol, 0.9 eq.) and Et$_3$N (0.1 mL, 0.68 mmol) were reacted according to GP7.

Yield: 160 mg (81%). Colorless foam. IR (KBr): 3425m; 3193w; 2932w; 1639s; 1528m; 1471m; 1449m; 1396w; 1329w; 1263m; 1208s; 1157w; 1082m; 1048m; 1018m; 867w; 781w; 700m; 643w. $^1$H-NMR (300 MHz, CDCl$_3$): 1.38 (s, 3 H, CH$_{3\text{-}exo}$); 1.61 (s, 3 H, CH$_{3\text{-}endo}$); 3.02 (bs, 3 H, N(CH$_3$)$_2$); 3.07 (bs, 3H, N(CH$_3$)$_2$); 4.05 (m, 2 H, H—C(7'), H—C(7")); 4.74 (dd, J=7.2, 3.3, 1 H, H—C(4')); 4.91 (dd; J=6.5, 3.3, 1 H, H—C(3')); 5.43 (dd, J=6.5, 2.0, 1 H, H—C(2')); 5.79 (m, 2 H, H—C(5'), H—C(6')); 6.08 (d, J=2.0, 1 H, H—C(1')); 6.18 (bs, 2 H, NH$_2$); 7.08 (t, J=5.7, 1 H, NHCO); 7.16 (d, J=1.8, 1 H, H$_{arom\ Cat.}$); 7.35-7.42 (m, 6 H, H$_{arom,\ Ketal}$); 7.46-7.51 (m, 4 H, H$_{arom,\ Ketal}$); 7.69 (d, J=1.8, 1 H, H$_{arom,\ Cat.}$); 7.82 (s, 1 H, H—C(8)); 8.17 (s, 1 H, H—C(2)). $^{13}$C-NMR (75 MHz, CDCl$_3$): 25.3; 27.0; 35.5; 39.8; 40.6; 84.4; 84.6; 87.5; 90.7; 111.2; 114.5; 114.6; 119.3; 120.1; 122.2; 126.4; 128.0; 128.5; 129.8; 130.3; 130.8;

138.5; 139.9; 145.6; 147.5; 149.1; 151.6; 154.8; 162.7; 170.3. HR-MS (MALDI): calcd. for $C_{38}H_{38}N_7O_7$ ([M+H]$^+$): 704.2833, found 704.2834.

c) N1-{(E)-3-[(3aR,4R,6R,6aR)-5-(6-amino-9H-purin-9-yl)-3,4-dihydroxytetrahydro-furan-2-yl]prop-2-enyl}-5-dimethylcarbamoyl-2,3-dihydroxy-benzamide

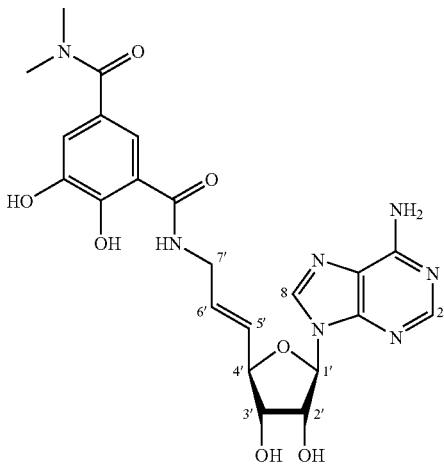

GP8, starting from the protected precursor (90 mg, 0.128 mmol) afforded the desired product as a colorless solid.

Yield: 54 mg (86%). $t_{R, analyt.}$: 7.3 min. IR (KBr): 3385 br, s; 1700s; 1605s; 1548w; 1509w; 1478w; 1416w; 1326w; 1296m; 1253w; 1202s; 1137m; 1048w; 972w; 838w; 801w; 725w. $^1$H-NMR (500 MHz, CD$_3$OD): 2.96 (bs, 6 H, N(CH$_3$)$_2$); 3.95 (m, 2 H, H—C(7'), H—C(7")); 4.14 (t, J=4.9, 1 H, H—C(4')); 4.42 (t, J=4.9, 1 H, H—C(3')); 4.66 (t, J=4.8, 1 H, H—C(2')); 5.83 (m, 2 H, H—C(5'), H—C(6')); 5.96 (d, J=4.8, H—C(1')); 6.92 (d, J=2.0, 1 H, H$_{arom, Cat.}$); 7.29 (d, J=2.0, 1 H, H$_{arom, Cat.}$); 8.15 (s, 1 H, H—C(8)); 8.31 (s, 1 H, H—C(2)). $^{13}$C-NMR (125 MHz, CD$_3$OD): 34.4; 38.8; 40.1; 73.7; 74.2; 84.8; 89.3; 115.1; 116.7; 116.8; 119.3; 126.0; 128.7; 129.4; 142.4; 145.4; 146.1; 148.6; 150.3; 151.5; 169.0; 171.8. HR-MS (MALDI): calcd. for $C_{22}H_{26}N_7O_7$ ([M+H]$^+$): 500.1894, found 500.1894.

EXAMPLE 15

Preparation of N1-{(E)-3-[(3aR,4R,6R,6aR)-5-(6-amino-9H-purin-9-yl)-3,4-dihydroxytetrahydrofuran-2-yl]prop-2-enyl}-5-((E)-2-dimethylcarbamoyl-vinyl)-2,3-dihydroxy-benzamide a) Methyl 6-((E)-2-dimethylcarbamoyl-vinyl)-2,2-diphenyl-1,3-benzodioxole-4-carboxylate

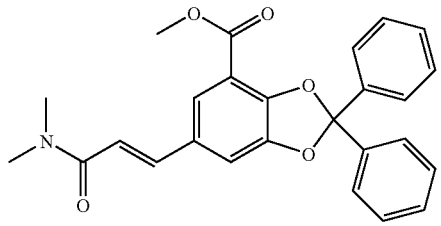

A solution of methyl 6-bromo-2,2-diphenyl-1,3-benzodioxole-4-carboxylate (130 mg, 0.32 mmol), N,N-dimethylacrylamide (47 mg, 0.47 mmol, 1.5 eq.), P(OPh)$_3$ (980 mg, 3.16 mmol, 10 eq.), Bu$_4$NBr (20 mg, 0.06 mmol, 0.2 eq.), Na$_2$CO$_3$ (40 mg, 0.38 mmol, 1.2 eq.) and Pd(OAc)$_2$ (10 mg, 0.03 mmol, 0.1 eq.) in 10 mL dimethylacetamide was stirred at 140° C. for 72 h. After cooling to r.t. the mixture was partitioned between EtOAc and H$_2$O. The organic layer was washed twice with saturated NaCl solution, dried over MgSO$_4$ and evaporated in vacuo. The crude product was purified using flash chromatography (silica gel, hexane/EtOAc 5:1→3:2) to yield the desired compound as a colorless, slowly solidifying viscous oil.

Yield: 60 mg (44%). IR (KBr): 3059w; 2927w; 1721s; 1652s; 1607m; 1481m; 1447s; 1396m; 1300m; 1256s; 1203s; 1046m; 1017m; 970w; 779w; 699m; 641w. $^1$H-NMR (300 MHz, CDCl$_3$): 3.11 (bs, 6 H, N(CH$_3$)$_2$); 3.96 (s, 3H, OCH$_3$); 6.75 (d, J=15.6, 1H, C(O)CH); 7.20 (d, J=1.8, 1 H, H$_{arom, Cat.}$); 7.36-7.41 (m, 6 H, H$_{arom, Ketal}$); 7.55-7.61 (m, 6 H, H$_{arom, Ketal}$, H$_{arom, Cat.}$, Ar—CH). $^{13}$C-NMR (75 MHz, CDCl$_3$): 36.2; 37.7; 52.5; 110.5; 113.0; 116.8; 119.1; 124.1; 126.6; 128.6; 129.6; 129.7; 139.6; 141.5; 149.2; 149.5; 164.9; 166.7. HR-MS (MALDI): calcd. for $C_{26}H_{23}NO_5Na$ ([M+Na]$^+$): 452.1474, found 452.1473.

b) 6-((E)-2-Dimethylcarbamoyl-vinyl)-2,2-diphenyl-1,3-benzodioxole-4-carboxylic acid

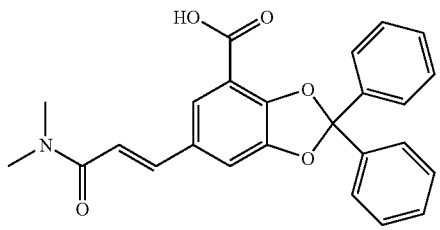

Methyl 6-((E)-2-dimethylcarbamoyl-vinyl)-2,2-diphenyl-1,3-benzodioxole-4-carboxylate (170 mg, 0.4 mmol, 1 eq.) and LiOH.H$_2$O (50 mg, 1.19 mmol, 3 eq.) were reacted according to GP3.

Yield: 126 mg (77%). Mp.: 230-231° C. IR (KBr): 3431w; 3058w; 1710s; 1653m; 1596m; 1467m; 1445m; 1404w; 1249s; 1212m; 1176m; 1050m; 1027w; 975w; 843w; 784w; 697w; 641w. $^1$H-NMR (300 MHz, CDCl$_3$): 3.07 (s, 3 H, N(CH$_3$)$_2$); 3.16 (s, 3 H, N(CH$_3$)$_2$); 6.75 (d, J=15.3, 1H, C(O)CH); 7.24 (d, J=1.5, 1 H, H$_{arom, Cat.}$); 7.35-7.40 (m, 6 H, H$_{arom, Ketal}$); 7.59-7.62 (m, 5 H, H$_{arom, Ketal}$, Ar—CH); 7.67 (d, J=1.5, 1 H, H$_{arom, Cat.}$). $^{13}$C-NMR (75 MHz, CDCl$_3$): 36.1; 37.5; 110.6; 112.3; 116.4; 119.2; 124.6; 126.3; 128.4; 129.4; 129.5; 139.2; 141.5; 149.1; 149.8; 166.8; 167.8. HR-MS (MALDI): calcd. for $C_{25}H_{22}NO_5$ ([M+H]$^+$): 416.1498, found 416.1498.

c) 6-((E)-2-Dimethylcarbamoyl-vinyl)-2,2-diphenyl-benzo[1,3]dioxole-4-carboxylic acid {3-[(3aR,4R,6R,6aR)-6-(6-amino-9H-purin-9-yl)-2,2-dimethyl-tetrahydro-furo[3,4-d][1,3]dioxol-4-yl]-prop-2-enyl}-amide

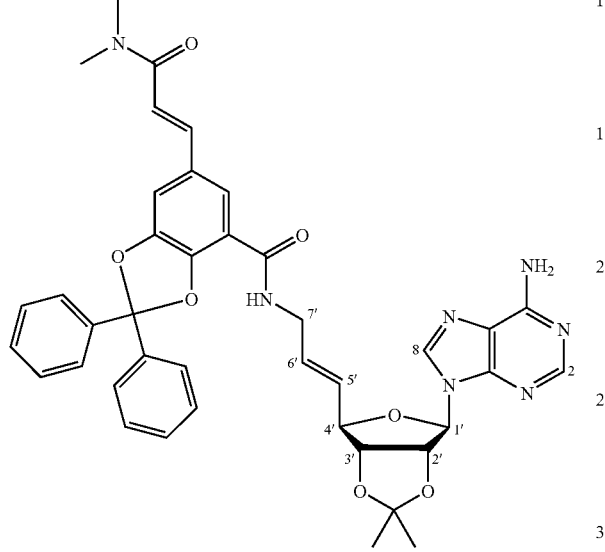

6-((E)-2-Dimethylcarbamoyl-vinyl)-2,2-diphenyl-1,3-benzodioxole-4-carboxylic acid (90 mg, 0.22 mmol, 1 eq.), EDC.HCl (63 mg, 0.33 mmol, 1.5 eq.), N-hydroxy-succinimide (33 mg, 0.28 mmol, 1.3 eq.), 9-{(3aR,4R,6R,6aR)-6-[(E)-3-aminoprop-1-enyl]-2,2-dimethylperhydro-furo[3,4-d][1,3]di-oxol-4-yl}-9H-purin-6-amine (72 mg, 0.22 mmol, 1 eq.) and Et$_3$N (0.1 mL, 0.68 mmol) were reacted according to GP7.

Yield: 63 mg (40%). Colorless foam. IR (KBr): 3424m; 2931w; 1653s; 1598s; 1528m; 1474m; 1437m; 1374w; 1259m; 1207m; 1154w; 1081m; 1049m; 1019m; 973w; 867w; 776w; 699w; 642w. $^1$H-NMR (300 MHz, CDCl$_3$): 1.37 (s, 3 H, CH$_{3\text{-}exo}$); 1.61 (s, 3 H, CH$_{3\text{-}endo}$); 3.05 (s, 3 H, N(CH$_3$)$_2$); 3.14 (s, 3 H, N(CH$_3$)$_2$); 4.05 (m, 2 H, H—C(7'), H—C(7")); 4.69 (m, 1 H, H—C(4')); 4.96 (dd; J=6.6, 3.9, 1 H, H—C(3')); 5.46 (dd, J=6.6, 2.1, 1 H, H—C(2')); 5.70 (bs, 2 H, NH$_2$); 5.84 (m, 1 H, H—C(5'), H—C(6')); 6.08 (d, J=2.1, 1 H, H—C(1')); 6.82 (d, J=15.5, 1 H, C(O)CH); 7.07 (t, J=6.0, 1 H, NHCO); 7.17 (d, J=1.7, 1 H, H$_{arom,\ Cat.}$); 7.35-7.42 (m, 6 H, H$_{arom,\ Ketal}$); 7.47-7.52 (m, 4 H, H$_{arom,\ Ketal}$); 7.60 (d, J=15.5, 1 H, Ar—CH); 7.80 (d, J=1.7, 1 H, H$_{arom,\ Cat.}$); 7.84 (s, 1 H, H—C(8)); 8.19 (s, 1 H, H—C(2)). $^{13}$C-NMR (75 MHz, CDCl$_3$): 25.4; 27.1; 35.9; 37.4; 40.7; 84.1; 84.5; 87.2; 90.3; 110.6; 114.6; 115.4; 117.0; 119.2; 120.2; 122.8; 126.4; 128.5; 129.8; 130.3; 130.5; 138.5; 138.6; 139.8; 141.2; 145.6; 147.9; 149.4; 153.0; 155.3; 162.9; 166.5. HR-MS (MALDI): calcd. for C$_{40}$H$_{40}$N$_7$O$_7$ ([M+H]$^+$): 730.2989, found 730.2993.

d) N1-{(E)-3-[(3aR,4R,6R,6aR)-5-(6-amino-9H-purin-9-yl)-3,4-dihydroxytetrahydro-furan-2-yl]prop-2-enyl}-5-((E)-2-dimethylcarbamoyl-vinyl)-2,3-dihydroxy-benzamide

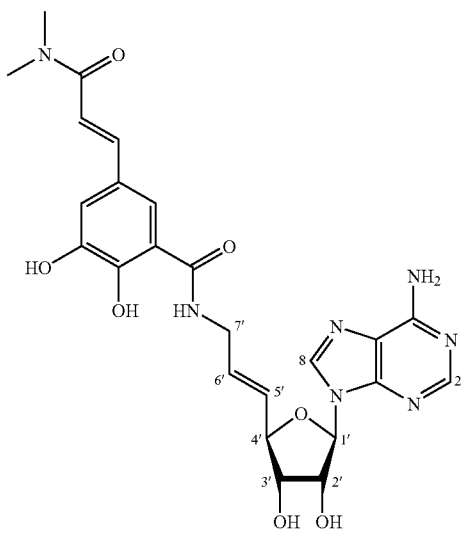

GP8, starting from the protected precursor (35 mg, 0.048 mmol) afforded the desired product as a colorless solid.

Yield: 12 mg (48%). $t_{R,analyt.}$: 9.7 min. IR (KBr): 3373 br, s; 1696s; 1642s; 1591s; 1499w; 1419w; 1307w; 1264w; 1201m; 1138w; 1052w; 977w; 840w; 800w; 723w; 642w. $^1$H-NMR (500 MHz, ): 3.05 (s, 3 H, N(CH$_3$)$_2$); 3.22 (s, 3 H, N(CH$_3$)$_2$); 4.07 (m, 2 H, H—C(7'), H—C(7")); 4.24 (t, J=5.0, 1 H, H—C(4')); 4.53 (m, 1 H, H—C(3')); 4.74 (t, J=4.8, 1 H, H—C(2')); 5.95 (m, 2 H, H—C(5'), H—C(6')); 6.06 (d, J=4.8, H—C(1')); 6.96 (d, J=15.4, 1 H, C(O)CH); 7.25 (d, J=1.8, 1 H, H$_{arom,\ Cat.}$); 7.46 (d, J=15.4, 1 H, Ar—CH); 7.53 (d, J=1.8, 1 H, H$_{arom,\ Cat.}$); 8.26 (s, 1 H, H—C(8)); 8.40 (s, 1 H, H—C(2)). $^{13}$C-NMR (125 MHz,): 36.3; 37.9; 41.7; 75.3; 75.8; 86.2; 90.7; 116.5; 116.6; 117.9; 199.9; 120.8; 127.5; 130.4; 131.0; 143.5; 143.6; 147.5; 148.0; 150.2; 152.4; 153.3; 169.3; 171.0. HR-MS (MALDI): calcd. for C$_{24}$H$_{27}$N$_7$O$_7$Na ([M+Na]$^+$): 548.1864, found 548.1859.

EXAMPLE 16

Preparation of N1-{(E)-3-[(3aR,4R,6R,6aR)-5-(6-amino-9H-purin-9-yl)-3,4-dihydroxytetrahydrofuran-2-yl]prop-2-enyl}-5-trifluoromethyl-2,3-dihydroxy-benzamide a) 2-Methoxymethoxy-5-trifluoromethyl-phenol

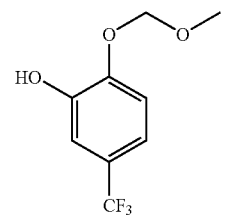

To a solution of 1-methoxymethoxy-4-trifluoromethyl-benzene (4.6 g, 22.31 mmol) in 60 mL dry THF cooled to −78° C., BuLi (21 mL of a 1.6 m sol. in hexane, 1.5 eq.) was added drop-wise via a syringe and the mixture was stirred at low temperature for 2 h, then the cooling bath was removed and the mixture was allowed to gradually warm to 0° C. during 30 min. After cooling again to −78° C., B(OCH$_3$)$_3$ (3.95 g, 38 mmol, 1.7 eq.) was added to the reaction and the stirring was continued for another 1.5 h at −78° C., then the solution was allowed to warm to −10° C. during 20 min. Re-cooling to −78° C. was followed by addition of H$_2$O$_2$ (5.82 mL of a 30% solution in H$_2$O, 2 eq.) and NaOH$_{aq}$ (5.8 mL of a 5 m aqueous solution, 1.3 eq.). This solution was stirred 16 h at r.t., then saturated NH$_4$Cl-solution was added and the mixture was extracted twice with 30 mL EtOAc. The pooled organic fractions were washed with saturated NaCl solution, dried over MgSO$_4$ and evaporated in vacuo. The crude product was purified using flash chromatography (silica gel, hexane/EtOAc 4:1) to yield the desired product as a yellowish oil.

Yield: 3.5 g (70%). IR (neat): 3426br, m; 2962m; 1709w; 1622m; 1516s; 1464m; 1330s; 1290s; 1162s; 1123s; 1085s; 982s; 914s; 879m; 816m; 762w; 658w; 618w. $^1$H-NMR (300 MHz, CDCl$_3$): 3.52 (s, 3 H, OCH$_3$); 5.26 (s, 2H, OCH$_2$O); 5.97 (s, 1H, OH); 7.10-7.20 (m, 3 H, H$_{arom}$). $^{13}$C-NMR (75 MHz, CDCl$_3$): 56.6; 95.5; 112.4 (d, J=3.6); 114.7; 117.5 (d, J=3.6); 120.3 (q, J=260); 125.0 (q, J=32.8); 146.1; 146.7. $^{19}$F-NMR (282 MHz, CDCl$_3$): −62.4 (s). HR-MS (EI+): calcd. for C$_9$H$_9$F$_3$O$_3$ ([M]$^+$): 222.0504, found 222.0501.

b) 3-Bromo-5-trifluoromethyl-benzene-1,2-diol

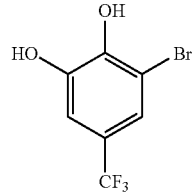

To a solution of 4-trifluoromethyl-benzene-1,2-diol (870 mg, 4.8 mmol) in 20 mL CCl$_4$, Br$_2$ (770 mg, 4.8 mmol, 1 eq.) was added and the mixture was stirred at 60° C. for 10 h. The solvent was then removed in vacuo and the crude product was purified by flash chromatography (silica gel, hexane/EtOAc 4:1→3:2) to yield the desired product as a yellowish oil.

Yield: 910 mg (74%). $^1$H-NMR (300 MHz, CDCl$_3$): 5.68 (bs, 1H, OH); 5.81 (bs, 1H, OH); 7.14 (dd, J=2.3, 0.6, 1 H, H$_{arom}$); 7.32 (dd, J=2.3, 0.6, 1 H, H$_{arom}$).

c) 1,2-Bis-benzyloxy-3-bromo-5-trifluoromethyl-benzene

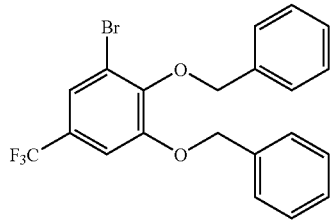

To a solution of 3-bromo-5-trifluoromethyl-benzene-1,2-diol (510 mg, 1.98 mmol) in 10 mL acetone, K$_2$CO$_3$ (2.74 g, 19.84 mmol, 10 eq.) and benzyl bromide (1.02 g, 5.95 mmol, 3 eq.) were added and the solution was refluxed for 4 h. After cooling to r.t., H$_2$O and EtOAc were added to the mixture and the phases were separated The organic fraction was washed with saturated NaCl solution, dried over MgSO$_4$ and evaporated in vacuo. The crude product was purified using flash chromatography (silica gel, hexane/EtOAc 10:1) to yield the title compound as a colorless solid.

Yield: 750 mg (87%). Mp.: 79-80° C. IR (KBr): 3032w; 2935w; 2884w; 1576w; 1499w; 1485w; 1455w; 1424m; 1382w; 1335s; 1290m; 1230m; 1164s; 1120s; 1011m; 957m; 919w; 859w; 751m; 698m. $^1$H-NMR (300 MHz, CDCl$_3$): 5.09 (s, 2 H, OCH$_2$Ar); 5.15 (s, 2 H, OCH$_2$Ar); 5.97 (s, 1H, OH); 7.18 (d, J=1.5, 1 H, H$_{arom, Cat.}$); 7.32-7.47 (m, 11 H, H$_{arom, Cat.}$, H$_{arom, Benzyl.}$). $^{13}$C-NMR (75 MHz, CDCl$_3$): 71.5; 75.0; 110.3 (d, J=3.9); 118.4; 122.5 (d, J=3.9); 123.1 (q, J=271); 127.0 (q, J=33.6); 127.6; 128.2; 128.3; 128.4; 128.5; 128.6; 135.5; 136.3; 148.4; 152.8. $^{19}$F-NMR (282 MHz, CDCl$_3$): −62.6 (s). HR-MS (MALDI): calcd. for C$_{21}$H$_{16}$BrF$_3$O$_2$Na ([M+Na]$^+$): 459.0183, found 459.0169.

d) Methyl 2,3-bis-benzyloxy-5-trifluoromethyl-benzoate

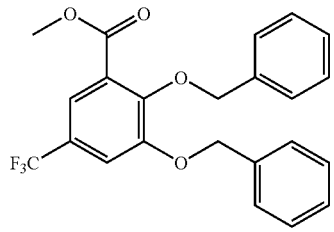

To a solution of 1,2-bis-benzyloxy-3-bromo-5-trifluoromethyl-benzene (750 mg, 1.76 mmol) in 10 mL dry THF cooled to −90° C., BuLi (3.3 mL of a 1.6 m solution in hexane, 5.28 mmol, 3 eq.) was slowly added via a syringe and the yellow solution was stirred at low temperature for 15 min. Methyl chloroformate (1.66 g, 17.6 mmol, 10 eq.) was then added to the solution and the reaction mixture was allowed to warm to r.t. where the stirring was continued for 1 h. The mixture was then poured into a separatory funnel containing H$_2$O and EtOAc and the phases were separated. The organic phase was washed with brine, dried over MgSO$_4$ and evaporated in vacuo. The crude product was purified using flash chromatography (silica gel, hexane/EtOAc 10:1) to yield the desired compound as a colorless solid.

Yield: 383 mg (52%). Mp.: 78-79° C. IR (KBr): 3033w; 2950w; 1733s; 1610w; 1486w; 1430m; 1363s; 1299m; 1250s; 1199m; 1151m; 1121s; 1045s; 956w; 935w; 909w; 867w; 750w; 698m. $^1$H-NMR (300 MHz, CDCl$_3$): 3.87 (s, 3H, OCH$_3$); 5.14 (s, 2 H, OCH$_2$Ar); 5.17 (s, 2 H, OCH$_2$Ar); 7.30-7.45 (m, 11 H, H$_{arom, Cat.}$, H$_{arom, Benzyl.}$); 7.65 (dd, J=1.8, 1.2, 1 H, H$_{arom, Cat.}$). $^{13}$C-NMR (75 MHz, CDCl$_3$): 52.5; 71.6; 75.8; 113.9 (d, J=3.3); 118.0; 119.9 (d, J=3.3); 123.4 (q, J=270); 126.0 (q, J=33.6); 127.0; 127.6; 128.1; 128.3; 128.4; 128.5; 128.6; 135.5; 136.6; 150.7; 153.0; 165.4. $^{19}$F-NMR (282 MHz, CDCl$_3$): −62.7 (s). HR-MS (MALDI): calcd. for C$_{23}$H$_{19}$F$_3$O$_2$Na ([M+Na]$^+$): 439.1133, found 439.1132. Anal. calcd. for Q$_3$H$_{19}$O$_4$F$_3$: C, 66.34, H 4.60. found C 66.16, H 4.78.

e) Methyl 2,3-dihydroxy-5-trifluoromethyl-benzoate

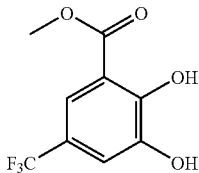

To a solution of methyl 2,3-bis-benzyloxy-5-trifluoromethyl-benzoate (280 mg, 0.67 mmol) in 10 mL MeOH, Pd/C (10%, 30 mg) was added and the mixture was stirred 16 h under a $H_2$ atmosphere. The reaction mixture was then filtered through Celite and evaporated in vacuo to yield the title compound as a greyish solid.

Yield: 148 mg (99%). IR (KBr): 3462m; 3132w; 2961w; 1676m; 1494m; 1447m; 1338s; 1245s; 1199m; 1120s; 1014w; 936w; 887w; 793m; 679m. $^1$H-NMR (300 MHz, CD$_3$OD): 3.97 (s, 3H, OCH$_3$); 7.17 (s, 1 H, H$_{arom, Cat}$); 7.58 (s, 1 H, H$_{arom, Cat}$). $^{13}$C-NMR (75 MHz, CD$_3$OD): 53.2; 113.6; 116.9; 118.0; 121.8 (q, J=32.8); 125.3 (q, J=268); 148.6; 154.6; 170.9. $^{19}$F-NMR (282 MHz, CD$_3$OD): −62.0 (s). HR-MS (MALDI): calcd. for $C_8H_3F_3O_3$ ([M−CH$_3$OH]$^+$): 204.0034, found 204.0024.

f) Methyl 2,2-Bis-(4-methoxy-phenyl)-6-trifluoromethyl-1,3-benzodioxole-4-carboxylate

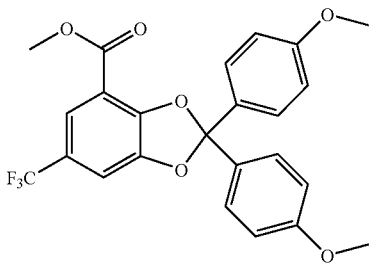

4,4'-Dimethoxybenzophenone (213 mg, 0.88 mmol, 1.5 eq.), oxalyl chloride (900 mg, 7.1 mmol, 8 eq.) and methyl 2,3-dihydroxy-5-trifluoromethyl-benzoate (130 mg, 0.59 mmol, 1 eq.) were reacted according to GP2.2. The crude product was purified using flash chromato-graphy (silica gel, hexane/Et$_2$O 10:1) to yield the title compound as a yellowish, very viscous oil.

Yield: 170 mg (63%). IR (neat): 3003w; 2956w; 2839w; 1727s; 1642w; 1612w; 1585w; 1514s; 1486m; 1445s; 1324s; 1268s; 1234s; 1175s; 1123m; 1042s; 1005m; 935w; 832m; 783w; 674w. $^1$H-NMR (300 MHz, CDCl$_3$): 3.81 (s, 6H, ArOCH$_3$); 3.95 (s, 3H, C(O)OCH$_3$); 6.90 (dd, J=6.7, 2.3, 4 H, H$_{arom, Ketal}$); 7.74 (d, J=1.5, 1 H, H$_{arom, Cat}$). $^{13}$C-NMR (75 MHz, CDCl$_3$): 52.4; 55.4; 108.6 (d, J=3.1); 112.3; 113.7; 120.2; 120.8 (d, J=4.3); 123.5 (q, J=270); 123.6 (q, J=33.4); 128.0; 131.0; 148.9; 150.7; 160.4; 163.8. $^{19}$F-NMR (282 MHz, CDCl$_3$): −61.8 (s). HR-MS (MALDI): calcd. for $C_{24}H_{20}F_3O_6$ ([M+H]$^+$): 461.1212, found 461.1202. Anal. calcd. for $C_{24}H_{19}O_6F_3$: C, 62.61, H 4.16. found C 62.52, H 4.26.

g) 2,2-Bis-(4-methoxy-phenyl)-6-trifluoromethyl-1,3-benzodioxole-4-carboxylic acid

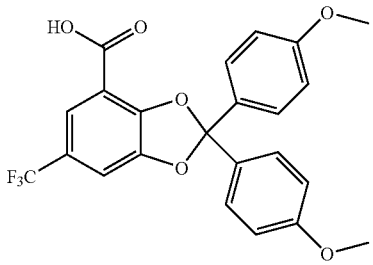

Methyl 2,2-bis-(4-methoxy-phenyl)-6-trifluoromethyl-1,3-benzodioxole-4-carboxylate (60 mg, 0.13 mmol, 1 eq.) and LiOH.H$_2$O (28 mg, 0.65 mmol, 5 eq.) were reacted according to GP3.

Yield: 53 mg (91%). Mp.:. IR (KBr): 3441br, w; 2936w; 2837w; 1687w; 1611s; 1513s; 1442m; 1364m; 1312s; 1253s; 1175s; 1121m; 1031s; 1005m; 952w; 931w; 831m; 676w. $^1$H-NMR (300 MHz, CDCl$_3$): 3.79 (s, 6H, ArOCH$_3$); 6.94 (dd, J=6.9, 2.1, 4 H, H$_{arom, Ketal}$); 7.30 (d, J=1.5, 1 H, H$_{arom, Cat}$); 7.46 (dd, J=6.9, 2.1, 4 H, H$_{arom, Ketal}$); 7.70 (d, J=1.5, 1 H, H$_{arom, Cat}$.) $^{19}$F-NMR (282 MHz, CDCl$_3$): −63.7 (s). HR-MS (MALDI): calcd. for $C_{24}H_{20}F_3O_6$ ([M+H]$^+$): 447.1055, found 447.1059.

h) 2,2-Bis-(4-methoxy-phenyl)-6-trifluoromethyl-benzo[1,3]dioxole-4-carboxylic acid {3-[(3aR,4R,6R,6aR)-6-(6-amino-9H-purin-9-yl)-2,2-dimethyl-tetrahydro-furo[3,4-d][1,3]dioxol-4-yl]-prop-2-enyl}-amide

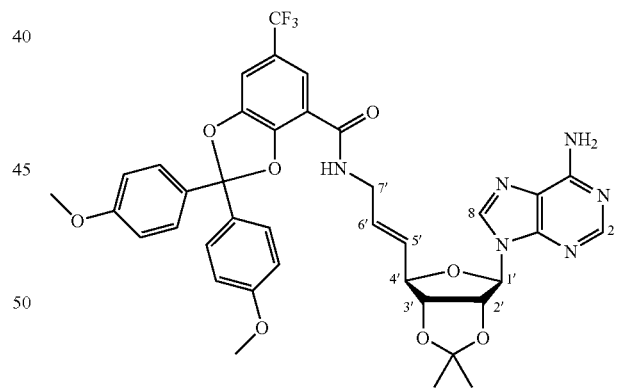

2,2-Bis-(4-methoxy-phenyl)-6-trifluoromethyl-1,3-benzodioxole-4-carboxylic acid (90 mg, 0.2 mmol, 1 eq.), EDC.HCl (58 mg, 0.3 mmol, 1.5 eq.), N-hydroxy-succinimide (31 mg, 0.26 mmol, 1.3 eq.), 9-{(3aR,4R,6R,6aR)-6-[(E)-3-aminoprop-1-enyl]-2,2-dimethylperhydrofuro[3,4-d][1,3]di-oxol-4-yl}-9H-purin-6-amine (70 mg, 0.2 mmol, 1 eq.) and Et$_3$N (0.1 mL, 0.68 mmol) were reacted according to GP7.

Yield: 119 mg (77%). Colorless foam. Mp.: 114-118° C. IR (KBr): 3426m; 3178w; 2935w; 2837w; 1640s; 1607s; 1514m; 1443w; 1375w; 1317s; 1254s; 1210m; 1175s; 1121m; 1025m; 1004w; 867w; 732m. $^1$H-NMR (300 MHz, CDCl$_3$): 1.38 (s, 3 H, CH$_{3-exo}$); 1.62 (s, 3 H, CH$_{3-endo}$); 3.81

(s, 6 H, OCH₃); 4.04 (m, 2 H, H—C(7'), H—C(7")); 4.68 (m, 1 H, H—C(4')); 4.95 (dd; J=6.6, 3.6, 1 H, H—C(3')); 5.45 (dd, J=6.6, 2.1, 1 H, H—C(2')); 5.81 (m, 4 H, H—C(5'), H—C(6'), NH₂); 6.08 (d, J=2.1, 1 H, H—C(1')); 6.88-6.92 (m, 4 H, H$_{arom, Ketal}$); 7.09 (t, J=5.7, 1 H, NHCO); 7.19 (d, J=2.1, 1 H, H$_{arom, Cat.}$); 7.36-7.42 (m, 4H, H$_{arom, Ketal}$); 7.85 (s, 1 H, H—C(8)); 7.91 (d, J=2.1, 1 H, H$_{arom, Cat.}$); 8.22 (s, 1 H, H—C(2)). ¹³C-NMR (75 MHz, CDCl₃): 25.4; 27.2; 40.9; 55.4; 84.1; 84.5; 87.1; 90.2; 108.3; 113.7; 114.6; 115.1; 120.1; 120.6; 120.7; 123.54 (q, J=270); 124.6 (q, J=33.5); 128.1; 128.5; 130.1; 130.3; 139.8; 147.2; 147.9; 149.2; 152.3; 155.1; 160.7; 162.0. ¹⁹F-NMR (282 MHz, CDCl₃): –61.7 (s). HR-MS (MALDI): calcd. for C₃₈H₃₆F₃N₆O₈ ([M+H]⁺): 761.2547, found 759.2535.

i) N1-{(E)-3-[(3aR,4R,6R,6aR)-5-(6-amino-9H-purin-9-yl)-3,4-dihydroxytetrahydrofuran-2-yl]prop-2-enyl}-5-trifluoromethyl-2,3-dihydroxybenzamide

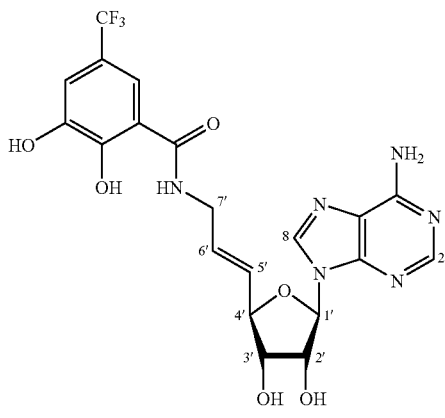

GP8, starting from the protected precursor (75 mg, 0.1 mmol) afforded the desired product as a colorless solid.

Yield: 48 mg (99%). t$_{R, analyt.}$: 14.7 min. IR (KBr): 3409 br, s; 1670s; 1649m; 1607m; 1545w; 1398w; 1327m; 1194m; 1124m; 1049w; 801w; 725w. ¹H-NMR (500 MHz, ): 4.06 (m, 2 H, H—C(7'), H—C(7")); 4.24 (t, J=5.1, 1 H, H—C(4')); 4.52 (m, 1 H, H—C(3')); 4.71 (t, J=4.8, 1 H, H—C(2')); 5.95 (m, 2 H, H—C(5'), H—C(6')); 6.06 (d, J=4.8, H—C(1')); 7.15 (d, J=1.2, 1 H, H$_{arom, Cat.}$); 7.64 (d, J=1.2, 1 H, H$_{arom, Cat.}$); 8.29 (s, 1 H, H—C(8)); 8.39 (s, 1 H, H—C(2)). ¹³C-NMR (125 MHz, ):41.8; 75.3; 75.6; 86.1; 90.6; 115.5 (q, J=2.5); 116.4 (q, J=5.0); 116.9; 120.8; 121.9 (q, J=32.5); 125.7 (q, J=269); 130.5; 130.9; 143.4; 147.8; 148.3; 150.3; 153.3; 153.6; 170.1. ¹⁹F-NMR (282 MHz, CDCl₃): –61.6 (s). HR-MS (MALDI): calcd. for C₂₀H₂₀F₃N₆O₆ ([M+H]⁺): 497.1396, found 497.1401.

EXAMPLE 17

Preparation of N1-{(E)-3-[(3aR,4R,6R,6aR)-5-(6-amino-9H-purin-9-yl)-3,4-dihydroxytetrahydrofuran-2-yl]prop-2-enyl}-5-isopropyl-2,3-dihydroxy-benzamide a)
4-Isopropenyl-2-methoxy-1-methoxymethoxy-benzene

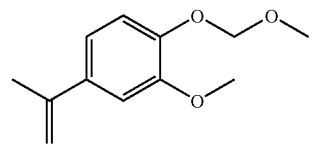

A suspension of methyltriphenylphosphonium bromide (1.1 g, 3.09 mmol, 1.3 eq.) in 5 mL dry THF cooled to –80° C. was slowly treated with BuLi (1.94 mL of a 1.6 m solution in hexane, 1.3 eq.). To this yellow suspension a solution of 1-(3-methoxy-4-methoxymethoxy-phenyl)-etha-none (500 mg, 2.38 mmol, 1 eq.) in 5 mL dry THF was added and the reaction mixture was allowed to warm to r.t. where stirring was continued for 12 h. The suspension was filtered and the solvent was evaporated in vacuo. The crude product was purified using flash chromatography (silica gel, hexane/EtOAc 6:1) to yield the desired product as a colorless oil.

Yield: 424 mg (86%). IR (neat): 3085w; 2952m; 2827w; 1627w; 1602w; 1580m; 1513s; 1463m; 1413m; 1300m; 1248s; 1224m; 1157s; 1139s; 1077s; 997s; 922m; 885m; 817w; 765w. ¹H-NMR (300 MHz, CDCl₃): 2.14 (s, 3 H, CH₃); 3.52 (s, 3 H, Ar—OCH₃); 3.91 (s, 3 H, OCH₃); 5.03 (qu, J=1.5, 1 H, CH₂); 5.23 (s, 2 H, OCH₂O); 5.29 (qu, J=1.5, 1 H, CH₂); 6.98-7.03 (m, 2 H, H$_{arom}$); 7.11 (d, J=8.4; 1 H, H$_{arom}$). ¹³C-NMR (75 MHz, CDCl₃): 21.9; 55.8; 56.2; 95.4; 109.2; 111.4; 115.9; 118.1; 135.9; 142.9; 146.0; 149.3. HR-MS (EI+): calcd. for C₁₂H₁₆O₃ ([M]⁺): 208.1099, found 208.1097.

b)
4-Isopropyl-2-methoxy-1-methoxymethoxy-benzene

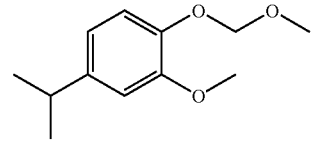

To a solution of 4-isopropenyl-2-methoxy-1-methoxymethoxy-benzene (3.5 g, 16.81 mmol) in 20 mL MeOH, Pd/C (10%, 350 mg) was added and the mixture was stirred 16 h under a H₂ atmosphere. The reaction mixture was then filtered through Celite and evaporated in vacuo and briefly dried under vacuum to yield the title compound as a colorless oil.

Yield: 3.31 g (94%). IR (neat): 2959s; 2827w; 1592w; 1516s; 1464s; 1419m; 1297w; 1266s; 1228s; 1198m; 1156s; 1079s; 1037w; 1004s; 923m; 852w; 815w; 763w; 653w. ¹H-NMR (300 MHz, CDCl₃): 1.24 (d, J=7.0, 6 H, CH₃); 2.86 (sep, J=7.0, 1 H, CH); 3.52 (s, 3 H, Ar—OCH₃); 3.88 (s, 3 H, OCH₃); 5.20 (s, 2 H, OCH₂O); 6.73-6.78 (m, 2 H, H$_{arom}$); 7.07 (d, J=8.1; 1 H, H$_{arom}$). ¹³C-NMR (75 MHz, CDCl₃): 24.1; 33.8; 55.8; 56.1; 95.6; 110.3; 116.5; 118.2; 143.5; 144.4; 149.5. HR-MS (EI+): calcd. for C₁₂H₁₈O₃ ([M]⁺): 210.1256, found 210.1246.

c) Methyl 5-Isopropyl-3-methoxy-2-methoxymethoxy-benzoate

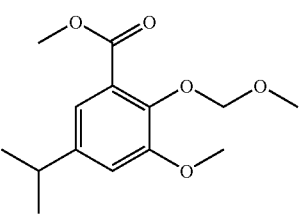

To a solution of 4-isopropyl-2-methoxy-1-methoxymethoxy-benzene (2.0 g, 9.51 mmol) in 35 mL dry THF cooled to 0° C., BuLi (9 mL of a 1.6 m solution in hexane, 1.5 eq.) was added dropwise via a syringe and the reaction mixture was stirred 2.5 h at 0° C. This solution was then slowly added to a solution of methyl chloroformate (9 g, 95.1 mmol, 10 eq.) in 10 mL dry THF at 0° C. The mixture was stirred 12 h at r.t. Saturated $KHCO_3$ solution and EtOAc were then added to the solution and the phases were separated. The organic layer was washed twice with saturated NaCl solution, dried over $MgSO_4$ and evaporated in vacuo. The crude product was purified using flash chromatography (silica gel, hexane EtOAc 9:1→6:1) to yield the title compound as a yellowish oil.

Yield: 1.3 g (51%). IR (neat): 2960m; 2841w; 1769m; 1729s; 1586w; 1487m; 1464m; 1439m; 1339m; 1263s; 1207s; 1157m; 1063s; 961s; 860w; 797w; 656w. $^1$H-NMR (300 MHz, $CDCl_3$): 1.24 (d, J=6.9, 6 H, $CH_3$); 2.88 (sep, J=6.9, 1 H, CH); 3.57 (s, 3 H, Ar—$OCH_3$); 3.86 (s, 3 H, $OCH_3$); 3.90 (s, 3 H, C(O)$OCH_3$); 5.10 (s, 2 H, $OCH_2O$); 6.91 (d, J=2.1, 1 H, $H_{arom}$); 7.18 (d, J=2.1; 1 H, $H_{arom}$). $^{13}$C-NMR (75 MHz, $CDCl_3$): 24.0; 34.0; 52.2; 56.2; 75.4; 99.4; 114.4; 119.8; 126.0; 143.3; 144.9; 152.8; 166.8. HR-MS (EI+): calcd. for $C_{14}H_{20}O_5$ ([M]$^+$): 268.1311, found 268.1300.

d) 2,3-Dihydroxy-5-isopropyl-benzoic acid

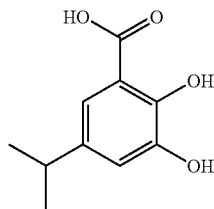

To a solution of methyl 5-Isopropyl-3-methoxy-2-methoxymethoxy-benzoate in 5 mL dry $CH_2Cl_2$ cooled to −80° C., $BBr_3$ (3.4 mL of a 1 m solution in $CH_2Cl_2$) was added dropwise via a syringe. The mixture was then stirred 30 min. at −70° C., then the cooling bath was removed and the stirring continued at r.t. for 1 h. The reaction was the quenched by addition of $H_2O$ and the resulting mixture was extracted twice with 30 mL $CH_2Cl_2$. The combined organic fractions were dried over $MgSO_4$ and evaporated in vacuo to yield a brown solid. This material was redissolved in 1 mL AcOH to which 2.5 mL HBr (33% in AcOH) was added The mixture was stirred at 120° C. for 5 h, then $H_2O$ was slowly added and the mixture was extracted with EtOAc. The organic layer was washed twice with saturated NaCl solution, dried over MgSO4 and evaporated in vacuo to yield the desired product as a brown solid.

Yield: 45 mg (41%). Mp.: 151-152° C. IR (KBr): 3311m; 2958s; 1675s; 1613w; 1483s; 1384w; 1276s; 1161s; 986w; 872w; 796w; 778w; 728w; 703w. $^1$H-NMR (300 MHz, $CDCl_3$): 1.22 (d, J=7.1, 6 H, $CH_3$); 2.84 (sep, J=7.1, 1 H, CH); 5.64 (bs, 1 H, OH); 7.09 (d, J=2.4, 1 H, $H_{arom}$); 7.30 (d, J=2.4; 1 H, $H_{arom}$); 10.29 (s, 1 H, OH). $^{13}$C-NMR (75 MHz, $CDCl_3$): 23.9; 33.5; 110.8; 118.7; 119.7; 140.5; 144.8; 147.4; 174.8. HR-MS (EI+): calcd. for $C_{10}H_{10}O_3$ ([M−$H_2O$]$^+$): 278.0630, found 278.0623.

e) Methyl 2,3-dihydroxy-5-isopropyl-benzoate

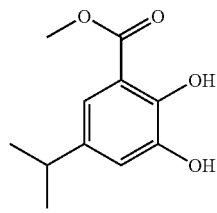

2,3-Dihydroxy-5-isopropyl-benzoic acid (140 mg, 0.71 mmol, 1 eq.) and $SOCl_2$ (430 mg, 3.6 mmol, 5 eq.) were reacted according to GP1.

Yield: 125 mg (83%). Grayish solid. Mp.: 66-67° C. IR (KBr): 3425s; 2955m; 1688s; 1485s; 1438s; 1338s; 1276s; 1231m; 1159m; 1112w; 1018m; 964w; 893w; 785m; 693w; 641w. $^1$H-NMR (300 MHz, $CDCl_3$): 1.21 (d, J=6.9, 6 H, $CH_3$); 2.82 (sep, J=6.9, 1 H, CH); 3.95 (s, 3 H, $OCH_3$); 5.61 (s, 1 H, OH); 7.02 (d, J=2.0, 1 H, $H_{arom}$); 7.21 (d, J=2.0, 1 H, $H_{arom}$); 10.69 (s, 1 H, OH). $^{13}$C-NMR (75 MHz, $CDCl_3$): 23.9; 33.5; 52.3; 111.8; 117.7; 118.4; 140.1; 144.7; 146.9; 170.8. HR-MS (EI+): calcd. for $C_{11}H_{14}O_4$ ([M]$^+$): 210.0892, found 210.0892.

f) Methyl 6-isopropyl-2,2-diphenyl-1,3-benzodioxole-4-carboxylate

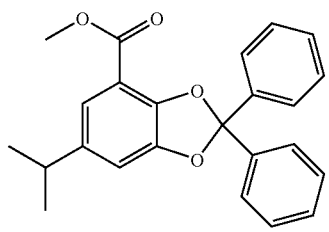

Methyl 2,3-dihydroxy-5-isopropyl-benzoate (85 mg, 0.4 mmol, 1 eq.) and dichlorodiphenyl-methane (125 mg, 0.53 mmol, 1.3 eq.) were reacted according to GP2, Method B.

Yield: 112 mg (74%). Colorless solid. Mp.: 108-110° C. IR (KBr): 2959w; 1714s; 1478s; 1447s; 1385w; 1285m; 1045m; 1017m; 915w; 868w; 807m; 782m; 701s; 641m. $^1$H-NMR (300 MHz, $CDCl_3$): 1.21 (d, J=6.8, 6 H, $CH_3$); 2.85 (sep, J=6.8, 1 H, CH); 3.94 (s, 3 H, $OCH_3$); 6.92 (d, J=1.9, 1 H, $H_{arom, Cat}$); 7.26 (d, J=1.9, 1 H, $H_{arom}$); 7.35-7.41 (m, 6 H, $H_{arom, Ketal}$); 7.60-7.65 (m, 4 H, $H_{arom, Ketal}$). $^{13}$C-NMR (75 MHz, $CDCl_3$): 24.0; 33.9; 52.0; 111.0; 112.1; 117.7; 119.9; 126.4; 128.2; 129.2; 140.0; 142.5; 146.3; 148.3; 165.4. HR-MS (MALDI): calcd. for $C_{24}H_{22}O_4Na$ ([M+Na]$^+$): 397.1416, found 397.1414.

g) 6-Isopropyl-2,2-diphenyl-1,3-benzodioxole-4-carboxylic acid

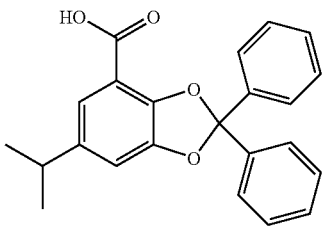

Methyl 6-isopropyl-2,2-diphenyl-1,3-benzodioxole-4-carboxylate (100 mg, 0.267 mmol, 1 eq.) and LiOH.H$_2$O (45 mg, 1.07 mmol, 4 eq.) were reacted according to GP3.

Yield: 91 mg (95%). Colorless solid. IR (KBr): 2958m; 2630w; 1683s; 1478s; 1450s; 1254s; 1207s; 1044m; 1023m; 947w; 864w; 760w; 697m; 641w. $^1$H-NMR (300 MHz, CDCl$_3$): 1.21 (d, J=6.9, 6 H, CH$_3$); 2.86 (sep, J=6.9, 1 H, CH); 6.97 (d, J=1.8, 1 H, H$_{arom, Cat.}$); 7.31 (d, J=1.8, 1 H, H$_{arom}$); 7.35-7.42 (m, 6 H, H$_{arom, Ketal}$); 7.61-7.64 (m, 4 H, H$_{arom, Ketal}$). $^{13}$C-NMR 75 MHz, CDCl$_3$): 24.0; 33.8; 111.2; 111.9; 118.2; 120.3; 126.4; 128.3; 129.3; 139.8; 142.7; 146.9; 148.4; 169.6. HR-MS (MALDI): calcd. for C$_{23}$H$_{20}$O$_4$Na ([M+Na]$^+$): 383.1259, found 383.1250.

h) 2,2-Diphenyl-6-isopropyl-benzo[1,3]dioxole-4-carboxylic acid {3-[(3aR,4R,6R,6aR)-6-(6-amino-9H-purin-9-yl)-2,2-dimethyl-tetrahydro-furo[3,4-d][1,3]dioxol-4-yl]-prop-2-enyl}-amide

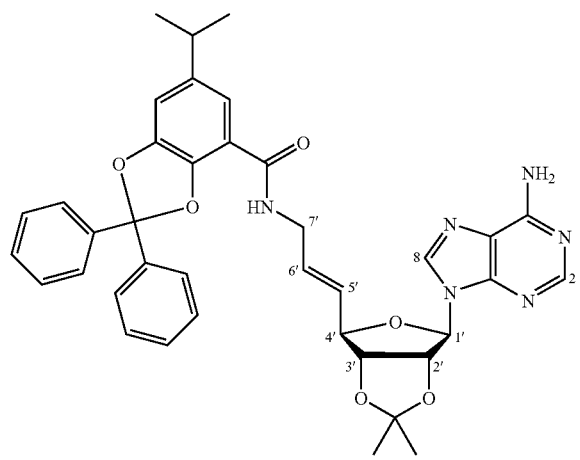

6-Isopropyl-2,2-diphenyl-1,3-benzodioxole-4-carboxylic acid (80 mg, 0.22 mmol, 1 eq.), EDC.HCl (64 mg, 0.33 mmol, 1.5 eq.), N-hydroxy-succinimide (34 mg, 0.29 mmol, 1.3 eq.), 9-{(3aR,4R,6R,6aR)-6-[(E)-3-aminoprop-1-enyl]-2,2-dimethylperhydrofuro[3,4-d][1,3]di-oxol-4-yl}-9H-purin-6-amine (81 mg, 0.24 mmol, 1.1 eq.) and Et$_3$N (0.1 mL, 0.68 mmol) were reacted according to GP7.

Yield: 89 mg (57%). Colorless foam. IR (KBr): 3424m; 3179w; 2960w; 1645s; 1598s; 1530m; 1475s; 1449m; 1330w; 1255s; 1208s; 1156w; 1081m; 1047m; 1018m; 949w; 867w; 779w; 699w; 642w. $^1$H-NMR (300 MHz, CDCl$_3$): 1.21 (d, J=6.9, 6 H, CH$_3$); 1.37 (s, 3 H, CH$_{3-exo}$); 1.62 (s, 3 H, CH$_{3-endo}$); 2.88 (sep, J=6.9, 1 H, CH); 4.05 (m, 2 H, H—C(7'), H—C(7")); 4.68 (m, 1 H, H—C(4")); 4.93 (dd; J=6.6, 3.9, 1 H, H—C(3')); 5.44 (dd, J=6.6, 2.4, 1 H, H—C(2')); 5.79 (bs, 2 H, NH$_2$); 5.86 (m, 2 H, H—C(5'), H—C(6')); 6.08 (d, J=2.4, 1 H, H—C(1')); 6.92 (d, J=1.5, 1 H, H$_{arom, Cat.}$); 7.14 (t, J=5.4, 1 H, NHCO); 7.35-7.39 (m, 6 H, H$_{arom, Ketal}$); 7.43 (d, J=1.5, 1 H, H$_{arom, Cat.}$); 7.48-7.53 (m, 4 H, H$_{arom, Ketal}$); 7.86 (s, 1 H, H—C(8)); 8.23 (s, 1 H, H—C(2)). $^{13}$C-NMR (75 MHz, CDCl$_3$): 24.1; 25.5; 27.2; 34.1; 40.7; 84.0; 84.4; 87.0; 90.1; 110.3; 114.7; 118.0; 119.7; 120.1; 126.3; 128.0; 128.3; 128.4; 129.5; 130.8; 139.1; 139.8; 142.7; 143.4; 147.1; 149.3; 152.5; 155.0; 163.5. HR-MS (MALDI): calcd. for C$_{38}$H$_{39}$N$_6$O$_6$ ([M+H]$^+$): 675.2931, found 675.2947.

i) N1-{(E)-3-[(3aR,4R,6R,6aR)-5-(6-amino-9H-purin-9-yl)-3,4-dihydroxytetrahydrofuran-2-yl]prop-2-enyl}-5-isopropyl-2,3-dihydroxy-benzamide

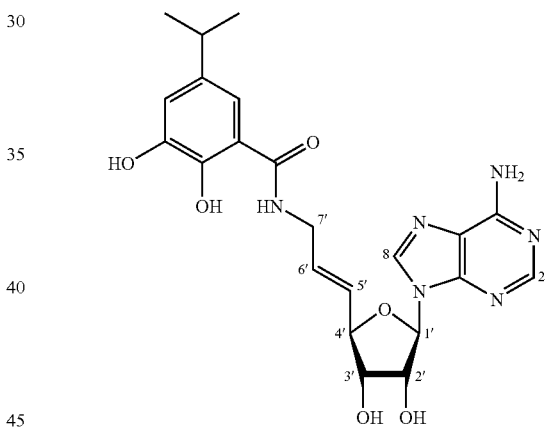

GP8, starting from the protected precursor (50 mg, 0.074 mmol) afforded the desired product as a grayish solid.

Yield: 29 mg (85%). t$_{R, analyt.}$: 12.2 min. IR (KBr): 3378br, s; 2962m; 1700s; 1641m; 1594m; 1542m; 1484w; 1430w; 1323w; 1201s; 1137m; 1049w; 970w; 836w; 800w; 724w; 642w. $^1$H-NMR (500 MHz, CD$_3$OD): 1.21 (d, J=6.8, 6 H, CH$_3$); 2.79 (sep, J=6.8, 1 H, CH); 4.03 (m, 2 H, H—C(7'), H—C(7")); 4.23 (t, J=4.9, 1 H, H—C(4+)); 4.51 (m, 1 H, H—C(3')); 4.73 (t, J=4.8, 1 H, H—C(2')); 5.94 (m, 2 H, H—C(5'), H—C(6')); 6.03 (d, J=4.8, H—C(1')); 6.85 (d, J=2.0, 1 H, H$_{arom, Cat.}$); 7.12 (d, J=2.0, 1 H, H$_{arom, Cat.}$); 8.22 (s, 1 H, H—C(8)); 8.37 (s, 1 H, H—C(2)). $^{13}$C-NMR (125 MHz, CD$_3$OD): 24.5; 35.0; 41.6; 75.2; 75.6; 86.1; 90.6; 116.2; 116.3; 118.2; 120.8; 130.2; 131.2; 140.7; 143.2; 147.1; 148.2; 148.7; 150.3; 154.1; 171.5. HR-MS (MALDI): calcd. for C$_{22}$H$_{27}$N$_6$O$_6$ ([M+H]$^+$): 471.1992, found 471.1981.

EXAMPLE 18

Preparation of N1-{(E)-3-[(3aR,4R,6R,6aR)-5-(6-amino-9H-purin-9-yl)-3,4-dihydroxytetrahydrofuran-2-yl prop-2-enyl}-5-(toluene-4-sulfonyl)-2,3-dihydroxy-benzamide a) Methyl 2,3-dimethoxy-5-(toluene-4-sulfonyl)-benzoate

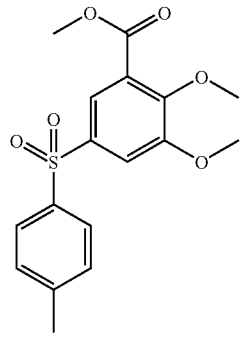

To a solution of methyl 5-iodo-2,3-dimethoxy-benzoate (2.25 g, 7.0 mmol) in 20 mL DMF, sodium p-toluenesulfinate hydrate (2.21 g, 11.26 mmol, 1.6 eq.) and CuI (2.22 g, 11.6 mmol, 1.66 eq.) were added and light green solution was stirred at 110° C. for 14 h. H$_2$O and EtOAc were then added to the mixture and the phases were separated. The organic layer was washed with saturated NaCl solution, dried over MgSO$_4$ and evaporated under reduced pressure. The crude product was purified using flash chromatography (silica gel, hexane/EtOAc 8:2→3:2) to yield the desired product as a colorless solid.

Yield: 1.41 g (58%). Mp.: 114° C. IR (KBr): 3081w; 2945w; 1731s; 1594w; 1482m; 1426w; 1317s; 1273s; 1146s; 1104m; 994w; 872w; 811w; 713w; 665m; 585m; 535w. $^1$H-NMR (300 MHz, CDCl$_3$): 2.40 (s, 3 H, ArCH$_3$); 3.90 (s, 3 H, ArOCH$_3$); 3.92 (s, 3 H, ArOCH$_3$); 3.92 (s, 3 H, C(O)OCH$_3$); 7.31 (d, J=8.1, 2 H, H$_{arom, p\text{-}Tol.}$); 7.54 (d, J=2.1, 1 H, H$_{arom, Cat.}$); 7.82 (d, J=8.1, 2 H, H$_{arom, p\text{-}Tol.}$); 7.87 (d, J=2.1; 1 H, H$_{arom, Cat.}$). $^{13}$C-NMR (75 MHz, CDCl$_3$): 21.7; 52.6; 56.5; 61.7; 113.4; 122.0; 126.4; 127.5; 129.9; 136.8; 138.2; 144.2; 152.7; 153.8; 164.9. HR-MS (MALDI): calcd. for C$_{17}$H$_{18}$O$_6$SNa ([M+Na]$^+$): 373.0722, found 373.0714. Anal. calcd. for C$_{17}$H$_{18}$O$_6$S: C 58.27, H 5.18. found C 58.38, H 5.36.

b) 2,3-Dihydroxy-5-(toluene-4-sulfonyl)-benzoic acid

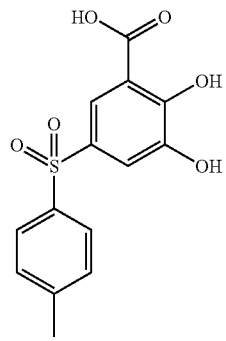

Methyl 2,3-dimethoxy-5-(toluene-4-sulfonyl)-benzoate (1.3 g, 4.036 mmol) was dissolved in 5 mL AcOH to which HBr (15 mL of a 33% solution in AcOH) and Bu$_4$NBr (1.1 g, 3.4 mmol, 0.85 eq.) were added. The reaction mixture was stirred at 140° C. for 20 h, then H$_2$O was slowly added and the mixture was extracted with EtOAc. The organic layer was washed twice with saturated NaCl solution, dried over MgSO$_4$ and evaporated in vacuo. The crude product was purified using flash chromatography (silica gel, hexane/EtOAc/AcOH 3:2:0.2→1:3:0.2) to yield the desired product as an orange solid.

Yield: 560 mg (45%). Mp.: 223-225° C. (dec.). IR (KBr): 3165br, m; 1692m; 1597w; 1467m; 1403w; 1282s; 1214w; 1141s; 1094m; 967w; 893w; 799w; 743w; 709m; 665m. $^1$H-NMR (300 MHz, DMSO-d$_6$): 2.35 (s, 3 H, ArCH$_3$); 4.42 (bs, 1 H, OH); 7.28 (d, J=2.1, 1 H, H$_{arom, Cat.}$); 7.39 (d, J=8.1, 2 H, H$_{arom, p\text{-}Tol.}$); 7.75 (m, 3 H, H$_{arom, Cat.}$, H$_{arom, p\text{-}Tol.}$); 9.86 (bs, 1 H, OH). $^{13}$C-NMR (75 MHz, DMSO-d$_6$): 21.0; 114.7; 115.6; 120.0; 126.8; 128.7; 130.0; 138.9; 143.6; 147.1; 156.4; 170.5. HR-MS (MALDI): calcd. for C$_{14}$H12O$_6$SNa ([M+Na]$^+$): 331.0252, found 331.0246.

c) Methyl 2,3-dihydroxy-5-(toluene-4-sulfonyl)-benzoate

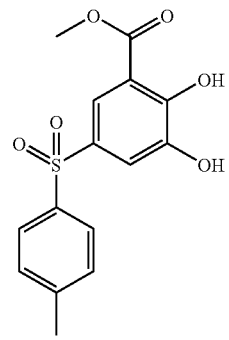

2,3-Dihydroxy-5-(toluene-4-sulfonyl)-benzoic acid (410 mg, 1.33 mmol, 1 eq.) and SOCl$_2$ (790 mg, 6.65 mmol, 5 eq.) were reacted according to GP1.

Yield: 321 mg (75%). Orange solid. Mp.: 168-170° C. (dec.). IR (KBr): 3362br, m; 2956w; 1695s; 1596m; 1494m; 1447m; 1284s; 1243s; 1146s; 1094m; 1018m; 937w; 883m; 810m; 736w; 700w; 666s. $^1$H-NMR (300 MHz, CDCl$_3$): 2.39 (s, 3 H, ArCH$_3$); 4.00 (s, 3 H, OCH$_3$); 5.91 (bs, 1 H, OH); 7.29 (d, J=7.8, 2 H, H$_{arom, p\text{-}Tol.}$); 7.55 (d, J=1.2, 1 H, H$_{arom, Cat.}$); 7.83 (d, J=7.8, 2 H, H$_{arom, p\text{-}Tol.}$); 8.05 (d, J=1.2, 1 H, H$_{arom, Cat.}$); 11.43 (bs, 1 H, OH). $^{13}$C-NMR (75 MHz, CDCl$_3$): 21.7; 53.1; 112.2; 117.8; 120.9; 127.4; 129.8; 132.8; 138.5; 144.1; 145.6; 152.5; 169.6. HR-MS (MALDI): calcd. for C$_{15}$H14O$_6$SNa ([M+Na]$^+$): 345.0409, found 345.0402.

d) Methyl 2,2-bis-(4-methoxy-phenyl)-6-(toluene-4-sulfonyl)-1,3-benzodioxole-4-carboxylate

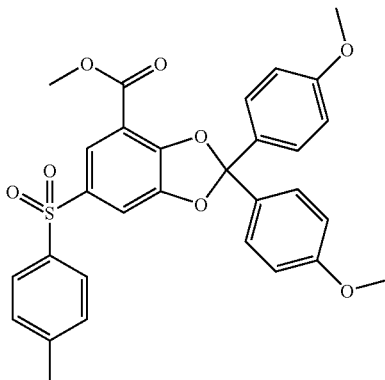

4,4'-Dimethoxybenzophenone (225 mg, 0.93 mmol, 1.5 eq.), oxalyl chloride (944 mg, 7.44 mmol, 8 eq.) and methyl 2,3-dihydroxy-5-(toluene-4-sulfonyl)-benzoate (200 mg, 0.62 mmol, 1 eq.) were reacted according to GP2.2. The crude product was purified using flash chromatography (silica gel, hexane/EtOAc 20:1→9:1) to yield the title compound as a colorless solid.

Yield: 260 mg (77%). Mp.: 79-82° C. IR (KBr): 2951w; 2832w; 1727m; 1610m; 1512m; 1464s; 1320m; 1285m; 1248s; 1210m; 1175s; 1150s; 1090m; 1042m; 1004w; 885w; 832w; 739w; 663w; 616w. $^1$H-NMR (300 MHz, CDCl$_3$): 2.39 (s, 3 H, ArCH$_3$); 3.80 (s, 6 H, ArOCH$_3$); 3.93 (s, 3 H, C(O)OCH$_3$); 6.88 (dt, J=8.7, 2.5, 4 H, H$_{arom, Ketal}$); 7.29 (d, J=8.1, 2 H, H$_{arom, p-Tol}$); 7.43 (m, 5 H, H$_{arom, Cat.}$, H$_{arom, Ketal}$); 7.81 (d, J=8.7, 2 H, H$_{arom, p-Tol}$); 8.09 (d, J=1.8, 1 H, H$_{arom, Cat.}$). $^{13}$C-NMR (75 MHz, CDCl$_3$): 21.7; 52.5; 55.4; 110.1; 112.5; 113.6; 120.9; 124.0; 127.5; 127.9; 129.9; 130.7; 134.9; 138.4; 144.1; 149.2; 151.9; 160.4; 163.4. HR-MS (MALDI): calcd. for C$_{30}$H$_{27}$O$_8$S ([M+H]$^+$): 547.1427, found 547.1428. Anal. calcd. for C$_{30}$H$_{26}$O$_8$S: C 65.65, H 4.87. found C 65.92, H 4.79.

e) 2,2-Bis-(4-methoxy-phenyl)-6-(toluene-4-sulfonyl)-1,3-benzodioxole-4-carboxylic acid

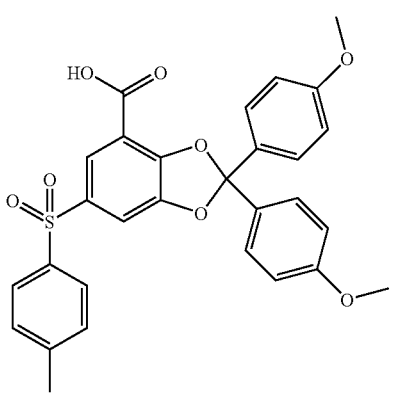

Methyl 2,2-bis-(4-methoxy-phenyl)-6-(toluene-4-sulfonyl)-1,3-benzodioxole-4-carboxylate (205 mg, 0.375 mmol, 1 eq.) and LiOH.H$_2$O (79 mg, 1.88 mmol, 5 eq.) were reacted following GP3.

Yield: 197 mg (99%). Colorless solid. IR (KBr): 3423br, w, 2961w; 2837w; 1649w; 1611m; 1514m; 1443m; 1313s; 1254s; 1175s; 1119m; 1030s; 931w; 903w; 832m; 675w. $^1$H-NMR )300 MHz, CD$_3$OD): 2.32 (s, 3 H, ArCH$_3$); 3.73 (s, 6 H, ArOCH$_3$); 6.85 (d, J=8.7, 4 H, H$_{arom, Ketal}$); 7.27 (d, J=8.1, 2 H, H$_{arom, p-Tol}$); 7.38 (d, J=8.7, 4 H, H$_{arom, Ketal}$); 7.43 (d, J=1.8, 1 H, H$_{arom, Cat.}$); 7.74 (d, J=8.1, 2 H, H$_{arom, p-Tol}$); 8.03 (d, J=1.8, 1 H, H$_{arom, Cat.}$). $^{13}$C-NMR (75 MHz, CD$_3$OD): 21.5; 55.8; 110.1; 114.0; 114.5; 125.4; 128.1; 128.4; 129.1; 130.8; 131.0; 132.0; 133.2; 135.9; 139.1; 145.7; 150.5; 162.0. HR-MS (MALDI): calcd. for C$_{29}$H$_{25}$O$_8$S ([M+H]$^+$): 533.1270, found 533.1274.

f) 2,2-Bis-(4-methoxy-phenyl)-6-(toluene-4-sulfonyl)-benzo[1,3]dioxole-4-carboxylic acid {3-[(3aR, 4R,6R,6aR)-6-(6-amino-9H-purin-9-yl)-2,2-dimethyl-tetrahydro-furo[3,4-d][1,3]dioxol-4-yl]-prop-2-enyl}-amide

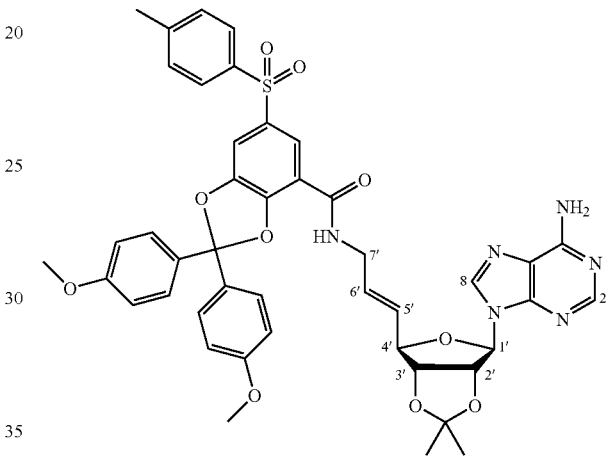

2,2-Bis-(4-methoxy-phenyl)-6-(toluene-4-sulfonyl)-1,3-benzodioxole-4-carboxylic acid (160 mg, 0.3 mmol, 1 eq.), EDC.HCl (86 mg, 0.45 mmol, 1.5 eq.), N-hydroxy-succinimide (46 mg, 0.39 mmol, 1.3 eq.), 9-{(3aR,4R,6R,6aR)-6-[(E)-3-aminoprop-1-enyl]-2,2-dimethylperhydro-furo[3,4-d][1,3]di-oxol-4-yl}-9H-purin-6-amine (100 mg, 0.31 mmol, 1 eq.) and Et$_3$N (0.1 mL, 0.68 mmol) were reacted according to GP7.

Yield: 146 mg (62%). Colorless foam. Mp.: 124-128° C. IR (KBr): 3424m; 2930w; 1640s; 1638s; 1607s; 1514s; 1458s; 1374w; 1315m; 1249s; 1209m; 1175s; 1184s; 1090s; 1004m; 833m; 664m; 616w. $^1$H-NMR (300 MHz, CDCl$_3$): 1.38 (s, 3 H, CH$_{3-exo}$); 1.61 (s, 3 H, CH$_{3-endo}$); 2.38 (s, 3 H, ArCH$_3$); 3.80 (s, 6 H, OCH$_3$); 4.01 (m, 2 H, H—C(7'), H—C(7'')); 4.69 (m, 1 H, H—C(4')); 4.94 (dd; J=6.5, 3.6, 1 H, H—C(3')); 5.45 (dd, J=6.5, 2.1, 1 H, H—C(2')); 5.77 (m, 2 H, H—C(5'), H—C(6')); 5.83 (bs, 2 H, NH$_2$); 6.09 (d, J=2.1, 1 H, H—C(1')); 6.88 (dt, J=8.7, 1.8, 4 H, H$_{arom, Ketal}$); 6.99 (t, J=5.7, 1 H, NHCO); 7.27 (d, J=7.8, 2 H, H$_{arom, p-Tol}$); 7.31-7.38 (m, 4 H, H$_{arom, Ketal}$); 7.48 (d, J=1.8, 1 H, H$_{arom, Cat.}$); 7.83 (d, J=7.8, 2 H, H$_{arom, p-Tol}$); 7.84 (s, 1 H, H—C(8)); 8.21 (s, 1 H, H—C(2)); 8.22 (d, J=1.8, 1 H, H$_{arom, Cat.}$). $^{13}$C-NMR 75 MHz, CDCl$_3$): 21.7; 25.4; 27.2; 40.9; 55.4; 84.2; 84.5; 87.2; 90.3; 109.8; 113.7; 114.5; 115.4; 120.1; 121.2; 124.0; 127.7; 128.1; 128.5; 129.8; 130.2; 136.1; 138.2; 139.8; 144.1; 148.1; 148.3; 149.2; 152.4; 155.0; 160.7; 161.6. HR-MS (MALDI): calcd. for C$_{44}$H$_{43}$N$_6$O$_{10}$S ([M+H]$^+$): 847.2761, found 847.2747. Anal. calcd. for C$_{44}$H$_{42}$N$_6$O$_{10}$S: C 62.40, H 5.00, N 9.92. found C 62.16, H 5.21, N 9.81.

g) N1-{(E)-3-[(3aR,4R,6R,6aR)-5-(6-amino-9H-purin-9-yl)-3,4-dihydroxytetrahydrofuran-2-yl]prop-2-enyl}-5-(toluene-4-sulfonyl)-2,3-dihydroxy-benzamide

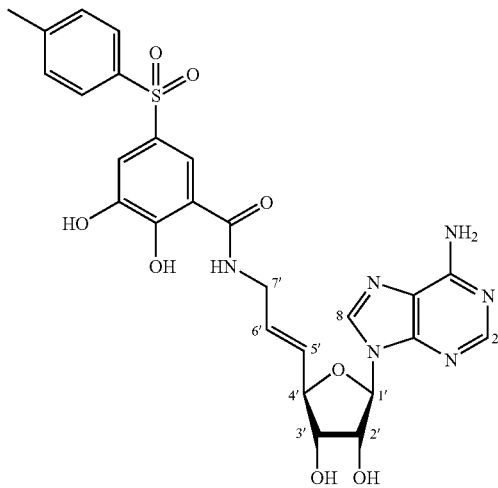

GP8, starting from the protected precursor (90 mg, 0.106 mmol) afforded the desired product as a colorless solid.

Yield: 61 mg (98%). $t_{R, \, analyt.}$: 13.9 min. IR (KBr): 3375br, s; 1695s; 1639m; 1597m; 1548w; 1467w; 1430w; 1286m; 1201s; 1144s; 1098w; 1051w; 973w; 799w; 723w; 666m. $^1$H-NMR (500 MHz, CD$_3$OD): 2.37 (s, 3 H, CH$_3$); 4.05 (m, 2 H, H—C(7'), H—C(7")); 4.23 (t, J=4.9, 1 H, H—C(4')); 4.51 (t, J=4.9, 1 H, H—C(3')); 4.72 (t, J=4.8, 1 H, H—C(2')); 5.94 (m, 2 H, H—C(5'), H—C(6')); 6.05 (d, J=4.8, H—C(1')); 7.33 (d, J=8.2, $H_{arom, \, p\text{-}Tol.}$); 7.35 (d, J=2.2, 1 H, $H_{arom, \, Cat.}$); 7.78 (d, J=8.2, $H_{arom, p\text{-}Tol.}$); 7.95 (d, J=2.2, 1 H, $H_{arom, \, Cat.}$); 8.25 (s, 1 H, H—C(8)); 8.38 (s, 1 H, H—C(2)). $^{13}$C-NMR (125 MHz, CD$_3$OD): 21.51; 41.8; 75.3; 75.6; 86.1; 90.7; 117.0; 117.2; 119.5; 120.8; 128.5; 130.5; 130.8; 131.1; 133.0; 140.5; 143.5; 145.7; 147.7; 148.6; 150.2; 153.5; 154.7; 169.8. HR-MS (MALDI): calcd. for C$_{26}$H$_{27}$N$_6$O$_6$S ([M+H]$^+$): 583.1611, found 583.1600.

EXAMPLE 19

Preparation of N1-{(E)-3-[(3aR,4R,6R,6aR)-5-(6-amino-9H-purin-9-yl)-3,4-dihydroxy-tetrahydrofuran-2-yl]prop-2-enyl}-5-(4-methyl-benzoyl)-2,3-dihydroxy-benzamide a) (3-[1,3]Dioxan-2-yl-4,5-dimethoxy-phenyl)-p-tolyl-methanol

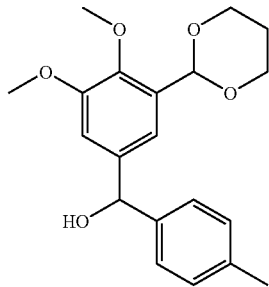

To a solution of 2-(5-Bromo-2,3-dimethoxy-phenyl)-[1,3]dioxane (2 g, 6.6 mmol) in 13 mL dry THF cooled to −78° C., t-BuLi (1.5M solution in pentane, 2.5 eq.) was added dropwise via a syringe and the resulting dark red suspension was stirred 30 min. at −78° C. p-Tolualdehyde (1.2 g, 10 mmol, 1.5 eq.) was added dropwise to the mixture and the resulting clear solution was stirred 30 min at −78° C., then 30 min at 0° C. H$_2$O (25 mL) was slowly added and the resulting solution was extracted with EtOAc (3×25 mL). The pooled organic fractions were dried over MgSO$_4$ and evaporated in vacuo. The crude product was purified using flash chromatography (silica gel, hexane/EtOAc 3:2) to yield the desired compound as a colorless solid.

(Takamitsu Hosoya, Eiji Takashiro, Takashi Matsumoto, Keisuke Suzuki, *J. Am. Chem. Soc.* 1994, 116, 1004-1015).

Yield: 2.13 g (94%). Mp.: 83-84° C. IR (KBr): 3464br, s; 2964m; 2851m; 1596w; 1490s; 1380s; 1317s; 1241s; 1140s; 1079s; 999s; 896m; 824w; 772m. $^1$H-NMR (300 MHz, CDCl$_3$): 1.43 (bd, J=13.8, 1 H, CH$_2$); 2.23 (m, 1 H, CH$_2$); 2.32 (s, 3 H, Ar—CH$_3$); 3.80 (s, 3 H, OCH$_3$); 3.83 (s, 3 H, OCH$_3$); 4.01 (tt, J=12.0, 2.7, 2 H, OCH$_2$); 4.24 (m, 2 H, OCH$_2$); 5.76 (bs, 1 H, O—CH(Ar)—O); 5.83 (s, 1 H, Ar—CH(OH)—Ar); 6.91 (d, J=1.8, 2 H, $H_{arom}$); 7.12 (d, J=8.1; 1 H, $H_{arom, \, p\text{-}Tol.}$); 7.25 (m, 3 H, $H_{arom}$, $H_{arom, \, p\text{-}Tol.}$). $^{13}$C-NMR (75 MHz, CDCl$_3$): 21.2; 25.9; 55.9; 61.4; 67.5; 75.9; 97.2; 110.8; 116.6; 126.4; 129.0; 132.1; 136.9; 140.1; 140.5; 145.8; 152.4. HR-MS (MALDI): calcd. for C$_{20}$H$_{24}$O$_5$Na ([M+Na]$^+$): 367.1521, found 367.1513. Anal. calcd. for C$_{20}$H$_{24}$O$_5$: C 69.75, H 7.02. found C 69.81, H 7.15.

b) 2,3-Dimethoxy-5-(4-methyl-benzoyl)-benzoic acid

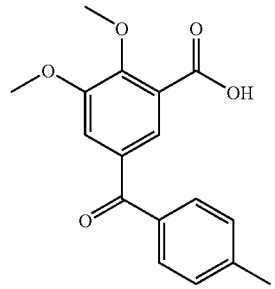

To a solution of (3-[1,3]Dioxan-2-yl-4,5-dimethoxy-phenyl)-p-tolyl-methanol (2.13 g, 6.18 mmol) in 75 mL THF, 56 mL 8N H$_2$SO$_4$ was added and the resulting solution was stirred 2 h at 50° C. After addition of 50 mL saturated NaCl-solution the mixture was extracted with EtOAc (3×50 mL). The pooled organic fractions were washed with saturated NaHCO$_3$-solution (50 mL), then saturated NaCl-solution (50 mL) before being dried over MgSO$_4$ and evaporated under reduced pressure to yield the desired product as a colorless oil. This crude product (2 g) was added to a mixture of 45 mL t-BuOH, 24 mL of a 1.25M K$_2$HPO$_4$-solution and 37 mL of a IM KMnO$_4$-solution and stirred 45 min. at 60° C. The mixture was partitioned between 100 mL saturated NaCl-solution and 100 mL CHCl$_3$ and the aqueous phase was extracted with CHCl$_3$ (3×100 mL). The pooled organic fractions were extracted with 2N NaOH-solution (3×100 mL), then the combined aqueous fractions were acidified with conc. HCl and extracted with CHCl₃ (4×100 mL). The organic fractions were pooled, dried over MgSO₄ and evaporated in vacuo to yield the title compound as a colorless solid.

Yield: 1.54 g (83%). Mp.: 135-136° C. IR (KBr): 2945br, s; 2620m; 1684s; 1598s; 1487s; 1442s; 1405s; 1339s; 1277s; 1129s; 1069s; 995s; 909m; 847m; 753s. ¹H-NMR (300 MHz, CDCl₃): 2.45 (s, 3 H, Ar—CH₃); 4.01 (s, 3 H, OCH₃); 4.19 (s, 3 H, OCH₃); 7.30 (d, J=8.1, 2 H, $H_{arom., p-Tol.}$); 7.69 (d, J=8.1; 1 H, $H_{arom., p-Tol.}$); 7.72 (d, J=2.1; 1 H, $H_{arom}$); 8.06 (d, J=2.1; 1 H, $H_{arom}$) ¹³C-NMR (75 MHz, CDCl₃): 21.8; 56.4; 62.4; 117.4; 121.7; 126.3; 129.1; 130.0; 133.9; 134.0; 143.6; 151.5; 152.5; 165.6; 194.3. HR-MS (MALDI): calcd. for $C_{17}H_{17}O_5$ ([M+H]⁺): 301.1076, found 301.1072.

c) 2,3-Dihydroxy-5-(4-methyl-benzoyl)-benzoic acid

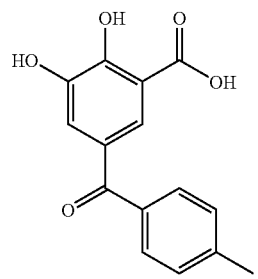

2,3-Dimethoxy-5-(4-methyl-benzoyl)-benzoic acid (300 mg, 1 mmol) was treated with a mixture of 6 mL 48% HBr and 3 mL AcOH and the mixture was stirred 14 h at 140° C. After cooling to r.t., the product was precipitated by addition of H₂O (60 mL). The precipitate was collected by filtration, washed with 60 mL H₂O and dried under reduced pressure.

Yield: 264 mg (97%). Mp.: 95-97° C. (dec.). IR (KBr): 3417br, s; 2566m; 1680s; 1609s; 1566w; 1432s; 1295s; 1253s; 1179s; 1123m; 862m; 801m; 753s. ¹H-NMR (300 MHz, CD₃OD): 2.44 (s, 3 H, Ar—CH₃); 7.33 (d, J=8.1,2 H, $H_{arom, p-Tol.}$); 7.47 (d, J=2.2; 1 H, $H_{arom}$); 7.62 (d, J=8.1; 1 H, $H_{arom, p-Tol.}$); 7.79 (d, J=2.2; 1 H, $H_{arom}$). ¹³C-NMR (75 MHz, CD₃OD): 21.6; 113.4; 121.5; 125.5; 129.4; 129.9; 130.7; 136.1; 144.3; 147.2; 155.8; 173.1; 196.5. HR-MS (MALDI): calcd. for $C_{15}H_{11}O_5$ ([M+H]⁻): 271.0607, found 271.0610.

d) 2,3-Dihydroxy-5-(4-methyl-benzoyl)-benzoic acid 2,5-dioxo-pyrrolidin-1-yl ester

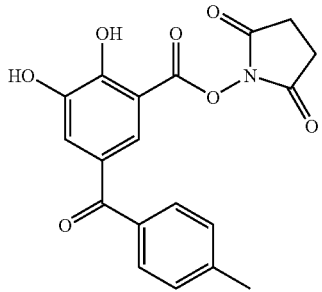

To a solution of 2,3-dihydroxy-5-(4-methyl-benzoyl)-benzoic acid (214 mg, 0.79 mmol) in 10 mL dry THF cooled to 0° C., N-hydroxysuccinimide (136 mg, 1.18 mmol, 1.5 eq.) and N-cyclohexylcarbodiimide, N'-methyl polystyrene HL (Novabiochem) (1.9 eq./g, 832 mg, 2 eq.) were added and the solution was stirred 14 h while the cooling bath slowly warmed up to r.t. The solution was filtered and the filtrate was evaporated under reduced pressure. The crude product was recrystallised from H₂O to yield the desired product as a brownish solid.

Yield: 233 mg (80%). Mp.: 93-95° C. (dec.). IR (KBr): 3341br, s; 2949m; 1738s; 1653m; 1606m; 1482w; 1368m; 1323m; 1203s; 1068s; 914w; 755w; 645w. ¹H-NMR (300 MHz, CD₃OD): 2.42 (s, 3 H, Ar—CH₃); 2.87 (s, 4 H, CH₂—CH₂); 7.33 (d, J=8.0, 2 H, $H_{arom, p-Tol.}$); 7.57 (d, J=1.7; 1 H, $H_{arom}$); 7.65 (d, J=8.0; 1 H, $H_{arom, p-Tol.}$); 7.87 (d, J=1.7; 1 H, $H_{arom}$). ¹³C-NMR (75 MHz, CD₃OD): 21.4; 26.4; 110.3; 121.9; 125.2; 129.8; 130.0; 130.6; 135.7; 144.3; 147.6; 154.6; 163.6; 171.2; 195.6. HR-MS (MALDI): calcd. for $C_{19}H_{16}NO_7$ ([M+H]⁺): 370.0927, found 370.0918.

e) N1-{(E)-3-[(3aR,4R,6R,6aR)-5-(6-amino-9H-purin-9-yl)-3,4-dihydroxytetrahydrofuran-2-yl]prop-2-enyl}-5-(4-methyl-benzoyl)-2,3-dihydroxy-benzamide

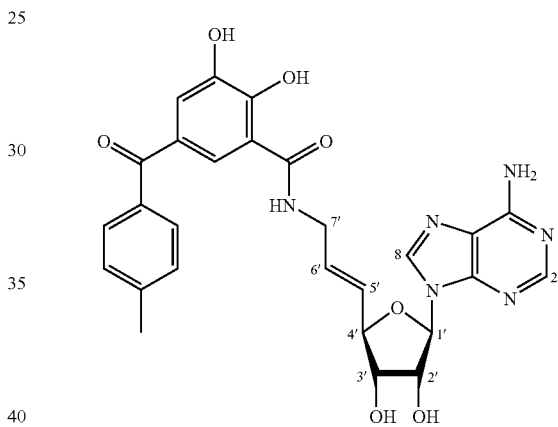

To a solution of 2,3-dihydroxy-5-(4-methyl-benzoyl)-benzoic acid 2,5-dioxo-pyrrolidin-1-yl ester (100 mg, 0.27 mmol) in DMF (4 mL), (2R,3S,4R,5R)-2-((E)-3-Amino-propenyl)-5-(6-amino-purin-9-yl)-tetrahydro-furan-3,4-diol (79 mg, 0.27 mmol, 1 eq.) and Et₃N (113 μL, 0.81 mmol, 3 eq.) were added and the solution was stirred 18 h at r.t. The crude product was purified using HPLC (RP C18, linear gradient of CH₃CN in H₂O with 0.1% TFA, 5→100% in 20 min, flow of 1 mL/min (analytical), UV-detection at 254 nm) to yield the title compound as a colorless solid.

Yield: 54 mg (37%). $t_{R, analyt.}$: 13.6 min. IR (KBr): 3378 br, s; 1642s; 1604s; 1427m; 1296s; 1120m; 1043w; 753w. ¹H-NMR (500 MHz, CD₃OD): 2.32 (s, 3 H, CH₃), 3.94 (m, 2 H, H—C(7'), H—C(7")); 4.13 (t, J=5.0, 1 H, H—C(4')); 4.41 (m, 1 H, H—C(3')); 4.63 (t, J=4.8, 1 H, H—C(2')); 5.83 (m, 2 H, H—C(5'), H—C(6')); 5.95 (d, J=4.8, 1 H, H—C (1')); 7.22 (d, J=8.2, 1 H, $H_{arom, Cat., p-Tol.}$); 7.28 (d, J=2, 1 H, $H_{arom, Cat.}$); 7.54 (d, J=8.2, 1 H, $H_{arom, Cat., p-Tol.}$); 7.70 (d, J=2, 1 H, $H_{arom, Cat.}$); 8.18 (s, 1 H, H—C(8)); 8.28 (s, 1 H, H—C(2)). ¹³C-NMR (125 MHz, (CD₃OD): 21.6; 41.6; 75.2; 75.6; 86.1; 90.6; 116.4; 120.3; 120.7; 122.7; 129.7; 130.1; 130.3; 130.9; 131.1; 136.4; 143.3; 144.5; 147.5; 148.0; 150.2; 153.6; 154.4; 170.4; 197.1. HR-MS (MALDI): calcd. for $C_{27}H_{27}N_6O_7$ ([M+H]⁺): 547.1941, found 547.1934.

| Tablet Formulation (Wet Granulation) | | | |
|---|---|---|---|
| | | mg/tablet | |
| Item | Ingredients | 25 mg | 100 mg |
| 1. | Compound of formula I | 25 | 100 |
| 2. | Lactose Anhydrous DTG | 105 | 30 |
| 3. | Sta-Rx 1500 | 6 | 6 |
| 4. | Microcrystalline Cellulose | 30 | 30 |
| 5. | Magnesium Stearate | 1 | 1 |
| | Total | 167 | 167 |

Manufacturing Procedure
1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

| Capsule Formulation | | | |
|---|---|---|---|
| | | mg/capsule | |
| Item | Ingredients | 25 mg | 100 mg |
| 1. | Compound of formula I | 25 | 100 |
| 2. | Hydrous Lactose | 123 | 148 |
| 3. | Corn Starch | 35 | 40 |
| 4. | Talc | 15 | 10 |
| 5. | Magnesium Stearate | 2 | 2 |
| | Total | 200 | 300 |

Manufacturing Procedure
1. Mix items 1, 2 and 3 in a suitable mixer for 30 minutes.
2. Add items 4 and 5 and mix for 3 minutes.
3. Fill into a suitable capsule.

What is claimed is:
1. A compound of formula I

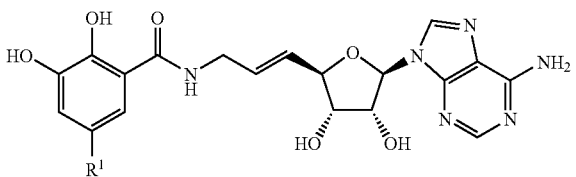

wherein
$R^1$ is H, CN, halogen, —$COR^2$, —$S(O)_xR^2$, $C_{1-12}$-alkyl, $C_{2-12}$-alkenyl, $C_{3-8}$-cycloalkyl, a heterocyclyl group, an aryl group, a heteroaryl group, $C_{3-8}$-cycloalkyl-($C_{1-3}$)-alkyl, a heterocyclyl-($C_{1-3}$)-alkyl group, an aryl-($C_{1-3}$)-alkyl group or a heteroaryl-($C_{1-3}$)-alkyl group; wherein the alkyl, alkenyl, alkoxy, cycloalkyl, heterocyclyl group, aryl group and heteroaryl groups are optionally substituted;
$R^2$ is —$N(R^3)(R^{3'})$, $C_{1-6}$-alkyl, $C_{3-8}$-cycloalkyl, heterocyclyl, aryl, heteroaryl, $C_{3-8}$-cycloalkyl-($C_{1-3}$)-alkyl, a heterocyclyl-($C_{1-3}$)-alkyl group, an aryl-($C_{1-3}$)-alkyl group or a heteroaryl-($C_{1-3}$)-alkyl group, wherein the $C_{1-6}$-alkyl, $C_{3-8}$-cycloalkyl, heterocyclyl, aryl, and heteroaryl are optionally substituted;
$R^3$ and $R^{3'}$ are independently hydrogen or ($C_{1-3}$)-alkyl;
x is 0, 1 or 2;
or an ester thereof which is hydrolyzable under physiological conditions or a pharmaceutically acceptable salt thereof.

2. A compound according to claim 1, wherein $R^1$ is a hydrogen, cyano, halogen, —$COR^2$, —$S(O)_2R^2$, $C_{1-6}$-alkyl, $C_{1-6}$-alkyl substituted with halogen, $C_{2-6}$-alkenyl substituted with $COR^2$, phenyl, phenyl substituted with $C_{1-6}$-alkyl or halogen, benzyl, or benzyl substituted with $C_{1-6}$-alkyl.

3. A compound according to claim 2, wherein $R^2$ is $C_{1-6}$-alkyl or $C_{1-6}$-alkyl substituted with halogen or —$N(R^3)(R^{3'})$ and wherein $R^3$ and $R^{3'}$ are each independently $C_{1-3}$-alkyl.

4. A compound according to claim 3, wherein $R^1$ is hydrogen, cyano, or halogen.

5. A compound according to claim 2, wherein $R^2$ is phenyl, phenyl substituted with $C_{1-6}$-alkyl or halogen, cyclohexyl, or heteroaryl.

6. A compound according to claim 5, wherein $R^1$ is hydrogen, cyano, or halogen.

7. A compound according to claim 5, wherein $R^2$ is pyridinyl, thiazolyl, or benzthiazolyl.

8. A compound according to claim 2, wherein heteroaryl is pyridinyl, thiazolyl, or benzthiazolyl.

9. A compound according to claim 3, wherein $R^1$ is hydrogen, cyano, or halogen.

10. A compound according to claim 9, selected from the group consisting of
N-{3-[5-(6-Amino-purin-9-yl)-3,4-dihydroxy-tetrahydro-furan-2-yl]-allyl}-2,3-dihydroxy-benzamide;
N-{3-[5-(6-Amino-purin-9-yl)-3,4-dihydroxy-tetrahydro-furan-2-yl]-allyl}-5-cyano-2,3-dihydroxy-benzamide;
N-{3-[5-(6-Amino-purin-9-yl)-3,4-dihydroxy-tetrahydro-furan-2-yl]-allyl}-5-bromo-2,3-dihydroxy-benzamide; and
N-{3-[5-(6-Amino-purin-9-yl)-3,4-dihydroxy-tetrahydro-furan-2-yl]-allyl}-5-chloro-2,3-dihydroxy-benzamide.

11. A compound according to claim 1, wherein $R^1$ is $C_{1-6}$-alkyl, $C_{1-6}$-alkyl substituted with halogen, or $C_{2-6}$-alkenyl substituted with $COR^2$.

12. A compound according to claim 11, wherein $R^2$ is —$N(R^3)(R^{3'})$ and wherein $R^3$ and $R^{3'}$ are each independently $C_{1-3}$-alkyl.

13. A compound according to claim 4, selected from the group consisting of
N-{3-[5-(6-Amino-purin-9-yl)-3,4-dihydroxy-tetrahydro-furan-2-yl]-allyl}-2,3-dihydroxy-5-isopropyl-benzamide;
N-{3-[5-(6-Amino-purin-9-yl)-3,4-dihydroxy-tetrahydro-furan-2-yl]-allyl}-5-(2-dimethyl-carbamoyl-vinyl)-2,3-dihydroxy-benzamide; and
N-{3-[5-(6-Amino-purin-9-yl)-3,4-dihydroxy-tetrahydro-furan-2-yl]-allyl}-2,3-dihydroxy-5-trifluoromethyl-benzamide.

14. A compound according to claim 1, wherein $R^1$ is —$COR^2$.

15. A compound according to claim 14, wherein $R^2$ is $C_{1-6}$-alkyl, $C_{1-6}$-alkyl substituted with halogen, or —$N(R^3)(R^{3'})$ and wherein $R^3$ and $R^{3'}$ are each independently $C_{1-3}$-alkyl.

16. A compound according to claim 15, selected from the group consisting of

N-{3-[5-(6-Amino-purin-9-yl)-3,4-dihydroxy-tetrahydro-furan-2-yl]-allyl}-2,3-dihydroxy-5-trifluoroacetyl-benzamide; and N3-{3-[5-(6-Amino-purin-9-yl)-3,4-dihydroxy-tetrahydro-furan-2-yl]-allyl}-4,5-dihydroxy-N1,N1-dimethyl-isophthalamide.

17. A compound according to claim 14, wherein $R^2$ is phenyl, phenyl substituted with $C_{1-6}$-alkyl or halogen, $C_{3-8}$-cycloalkyl, or heteroaryl.

18. A compound according to claim 17, wherein $R^2$ is cyclohexyl.

19. A compound according to claim 17, wherein heteroaryl is pyridinyl, thiazolyl, or benzthiazolyl.

20. A compound according to claim 17, selected from the group consisting of
N-{3-[5-(6-Amino-purin-9-yl)-3,4-dihydroxy-tetrahydro-furan-2-yl]-allyl}-2,3-dihydroxy-5-(4-methyl-benzoyl)-benzamide;
N-{3-[5-(6-Amino-purin-9-yl)-3,4-dihydroxy-tetrahydro-furan-2-yl]-allyl}-5-cyclohexanecarbonyl-2,3-dihydroxy-benzamide; and
N-{3-[5-(6-Amino-purin-9-yl)-3,4-dihydroxy-tetrahydro-furan-2-yl]-allyl}-2,3-dihydroxy-5-(pyridine-4-carbonyl)-benzamide.

21. A compound according to claim 1, wherein $R^1$ is —S(O)$_2$R$^2$.

22. A compound according to claim 21, wherein $R^2$ is $C_{1-6}$-alkyl, $C_{1-6}$-alkyl substituted with halogen, or —N(R$^3$)(R$^{3'}$) and wherein $R^3$ and $R^{3'}$ are each independently $C_{1-3}$-alkyl.

23. A compound according to claim 21, wherein $R^2$ is phenyl, phenyl substituted with $C_{1-6}$-alkyl or halogen, cyclohexyl, or heteroaryl.

24. A compound according to claim 23, wherein heteroaryl is pyridinyl, thiazolyl, or benzthiazolyl.

25. A compound according to claim 21, which is N-3-[5-(6-Amino-purin-9-yl)-3,4-dihydroxy-tetrahydro-furan-2-yl]-allyl}-2,3-dihydroxy-5-(toluene-4-sulfonyl)-benzamide.

26. A compound according to claim 1, wherein $R^1$ is phenyl, phenyl substituted with $C_{1-6}$-alkyl or halogen, pyridinyl, thiazolyl, benzthiazolyl, benzyl, or benzyl substituted with $C_{1-6}$-alkyl.

27. A compound according to claim 26, selected from the group consisting of
4'-Fluoro-4,5-dihydroxy-biphenyl-3-carboxylic acid {3-[5-(6-amino-purin-9-yl)-3,4-dihydroxy-tetrahydro-furan-2-yl]-allyl}-amide;
N-{3-[5-(6-Amino-purin-9-yl)-3,4-dihydroxy-tetrahydro-furan-2-yl]-allyl}-2,3-dihydroxy-5-thiazol-2-yl-benzamide;
N-{3-[5-(6-Amino-purin-9-yl)-3,4-dihydroxy-tetrahydro-furan-2-yl]-allyl}-2,3-dihydroxy-5-pyridin-4-yl-benzamide;
4,5-Dihydroxy-4'-methyl-biphenyl-3-carboxylic acid {3-[5-(6-amino-purin-9-yl)-3,4-dihydroxy-tetrahydro-furan-2-yl]-allyl}-amide;
N-{3-[5-(6-Amino-purin-9-yl)-3,4-dihydroxy-tetrahydro-furan-2-yl]-allyl}-5-benzothiazol-2-yl-2,3-dihydroxy-benzamide; and
N-{3-[5-(6-Amino-purin-9-yl)-3,4-dihydroxy-tetrahydro-furan-2-yl]-allyl}-2,3-dihydroxy-5-(4-methyl-benzyl)-benzamide.

28. A pharmaceutical composition comprising a therapeutically effective amount of one of more compounds of formula I

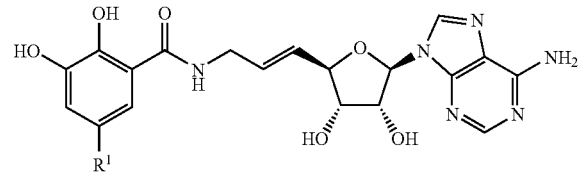

wherein
$R^1$ is H, CN, halogen, —COR$^2$, —S(O)$_x$R$^2$, $C_{1-12}$-alkyl, $C_{2-12}$-alkenyl, $C_{3-8}$-cycloalkyl, a heterocyclyl group, an aryl group, a heteroaryl group, $C_{3-8}$-cycloalkyl-($C_{1-3}$)-alkyl, a heterocyclyl-($C_{1-3}$)-alkyl group, an aryl-($C_{1-3}$)-alkyl group or a heteroaryl-($C_{1-3}$)-alkyl group; wherein the alkyl, alkenyl, alkoxy, cycloalkyl, heterocyclyl group, aryl group and heteroaryl groups are optionally substituted;

$R^2$ is —N(R$^3$)(R$^{3'}$), $C_{1-6}$-alkyl, $C_{3-8}$-cycloalkyl, heterocyclyl, aryl, heteroaryl, $C_{3-8}$-cycloalkyl-($C_{1-3}$)-alkyl, a heterocyclyl-($C_{1-3}$)-alkyl group, an aryl-($C_{1-3}$)-alkyl group or a heteroaryl-($C_{1-3}$)-alkyl group, wherein the $C_{1-6}$-alkyl, $C_{3-8}$-cycloalkyl, heterocyclyl, aryl, heteroaryl are optionally substituted;

$R^3$ and $R^{3'}$ are independently hydrogen or ($C_{1-3}$)-alkyl;

x is 0, 1 or 2;

or an ester thereof which is hydrolyzable under physiological conditions or a pharmaceutically acceptable salt thereof and a pharmaceutically acceptable carrier.

29. A method of treating schizophreniza, comprising administering to an individual a therapeutically effective amount of a compound of formula I

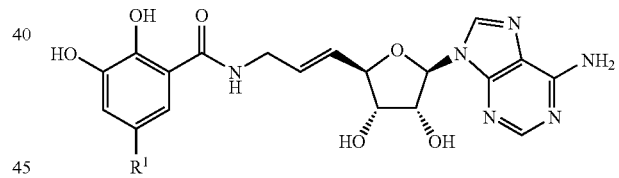

wherein
$R^1$ is H, CN, halogen, —COR$^2$, —S(O)$_x$R$^2$, $C_{1-12}$-alkyl, $C_{2-12}$-alkenyl, $C_{3-8}$-cycloalkyl, a heterocyclyl group, an aryl group, a heteroaryl group, $C_{3-8}$-cycloalkyl-($C_{1-3}$)-alkyl, a heterocyclyl-($C_{1-3}$)-alkyl group, an aryl-($C_{1-3}$)-alkyl group or a heteroaryl-($C_{1-3}$)-alkyl group; wherein the alkyl, alkenyl, alkoxy, cycloalkyl, heterocyclyl group, aryl group and heteroaryl groups are optionally substituted;

$R^2$ is —N(R$^3$)(R$^{3'}$), $C_{1-6}$-alkyl, $C_{3-8}$-cycloalkyl, heterocyclyl, aryl, heteroaryl, $C_{3-8}$-cycloalkyl-($C_{1-3}$)-alkyl, a heterocyclyl-($C_{1-3}$)-alkyl group, an aryl-($C_{1-3}$)-alkyl group or a heteroaryl-($C_{1-3}$)-alkyl group, wherein the $C_{1-6}$-alkyl, $C_{3-8}$-cycloalkyl, heterocyclyl, aryl, heteroaryl are optionally substituted;

$R^3$ and $R^{3'}$ are independently hydrogen or ($C_{1-3}$)-alkyl;

x is 0, 1 or 2;

or an ester thereof which is hydrolyzable under physiological conditions or a pharmaceutically acceptable salt thereof.

30. A method of treating depression, comprising administering to an individual a therapeutically effective amount of a compound of formula I

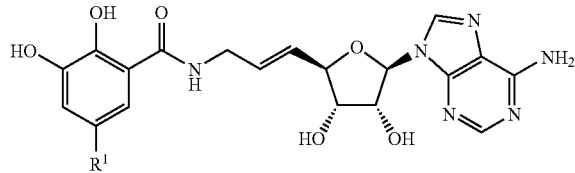

wherein
R$^1$ is H, CN, halogen, —COR$^2$, —S(O)$_x$R$^2$, C$_{1-12}$-alkyl, C$_{2-12}$-alkenyl, C$_{3-8}$-cycloalkyl, a heterocyclyl group, an aryl group, a heteroaryl group, C$_{3-8}$-cycloalkyl-(C$_{1-3}$)-alkyl, a heterocyclyl-(C$_{1-3}$)-alkyl group, an aryl-(C$_{1-3}$)-alkyl group or a heteroaryl-(C$_{1-3}$)-alkyl group; wherein the alkyl, alkenyl, alkoxy, cycloalkyl, heterocyclyl group, aryl group and heteroaryl groups are optionally substituted;
R$^2$ is —N(R$^3$)(R$^{3'}$), C$_{1-6}$-alkyl, C$_{3-8}$-cycloalkyl, heterocyclyl, aryl, heteroaryl, C$_{3-8}$-cycloalkyl-(C$_{1-3}$)-alkyl, a heterocyclyl-(C$_{1-3}$)-alkyl group, an aryl-(C$_{1-3}$)-alkyl group or a heteroaryl-(C$_{1-3}$)-alkyl group, wherein the C$_{1-6}$-alkyl, C$_{3-8}$-cycloalkyl, heterocyclyl, aryl, heteroaryl are optionally substituted;
R$^3$ and R$^{3'}$ are independently hydrogen or (C$_{1-3}$)-alkyl;
x is 0, 1 or 2;
or an ester thereof which is hydrolyzable under physiological conditions or a pharmaceutically acceptable salt thereof.

31. A process for preparing a compound of formula I

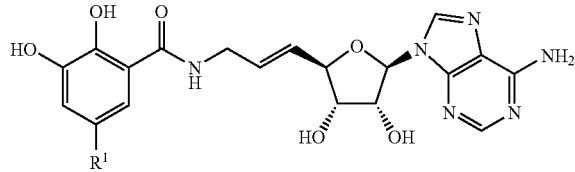

wherein
R$^1$ is H, CN, halogen, —COR$^2$, —S(O)$_x$R$^2$, C$_{1-12}$-alkyl, C$_{2-12}$-alkenyl, C$_{3-8}$-cycloalkyl, a heterocyclyl group, an aryl group, a heteroaryl group, C$_{3-8}$-cycloalkyl-(C$_{1-3}$)-alkyl, a heterocyclyl-(C$_{1-3}$)-alkyl group, an aryl-(C$_{1-3}$)-alkyl group or a heteroaryl-(C$_{1-3}$)-alkyl group; wherein the alkyl, alkenyl, alkoxy, cycloalkyl, heterocyclyl group, aryl group and heteroaryl groups are optionally substituted;
R$^2$ is —N(R$^3$)(R$^{3'}$), C$_{1-6}$-alkyl, C$_{3-8}$-cycloalkyl, heterocyclyl, aryl, heteroaryl, C$_{3-8}$-cycloalkyl-(C$_{1-3}$)-alkyl, a heterocyclyl-(C$_{1-3}$)-alkyl group, an aryl-(C$_{1-3}$)-alkyl group or a heteroaryl-(C$_{1-3}$)-alkyl group, wherein the C$_{1-6}$-alkyl, C$_{3-8}$-cycloalkyl, heterocyclyl, aryl, heteroaryl are optionally substituted;
R$^3$ and R$^{3'}$ are independently hydrogen or (C$_{1-3}$)-alkyl;
x is 0, 1 or 2;
said process comprising
a) reacting 9-{(3aR,4R,6R,6aR)-6-[(E)-3-aminoprop-1-enyl]-2,2-dimethylperhydro-furo[3,4-d][1,3]di-oxol-4-yl}-9H-purin-6-amine of formula II

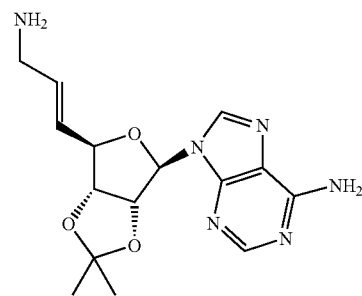

with an optionally protected 2,3-dihydroxy-benzoic acid derivative of formula IIIa or IIIb substituted by R$^1$ in position 5

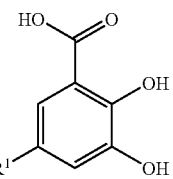

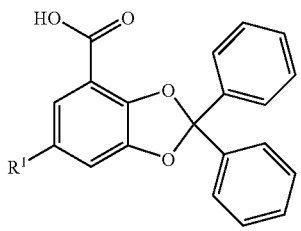

wherein R$^1$ is as defined above in the presence of (3-dimethylamino-propyl)-ethyl-carbodiimide (EDC), triethyl amine and N-hydroxy-succinimide (HOSu) in a solvent; and
b) optionally deprotecting the hydroxy groups with trifluoroacetic acid in an aqueous solution to form a compound of formula I.

* * * * *